(12) United States Patent
Ericsson et al.

(10) Patent No.: US 12,053,458 B2
(45) Date of Patent: Aug. 6, 2024

(54) TREATING SICKLE CELL DISEASE WITH A PYRUVATE KINASE R ACTIVATING COMPOUND

(71) Applicant: Novo Nordisk Health Care AG, Zurich (CH)

(72) Inventors: Anna Ericsson, Shrewsbury, MA (US); Neal Green, Newton, MA (US); Gary Gustafson, Ridgefield, CT (US); David R. Lancia, Jr., Westwood, MA (US); Bingsong Han, Westwood, MA (US); Lorna Mitchell, Cambridge (NZ); David Richard, Littleton, MA (US); Zhongguo Wang, Lexington, MA (US); Tatiana Shelekhin, Watertown, MA (US); Chase C. Smith, Watertown, MA (US); Xiaozhang Zheng, Watertown, MA (US)

(73) Assignee: Novo Nordisk Health Care AG, Zurich (CH)

( * ) Notice: Subject to any disclaimer, the term of this patent is extended or adjusted under 35 U.S.C. 154(b) by 570 days.

(21) Appl. No.: 17/275,741

(22) PCT Filed: Sep. 19, 2019

(86) PCT No.: PCT/US2019/052024
§ 371 (c)(1),
(2) Date: Mar. 12, 2021

(87) PCT Pub. No.: WO2020/061378
PCT Pub. Date: Mar. 26, 2020

(65) Prior Publication Data
US 2022/0031671 A1    Feb. 3, 2022

Related U.S. Application Data

(60) Provisional application No. 62/811,904, filed on Feb. 28, 2019, provisional application No. 62/789,641, filed on Jan. 8, 2019, provisional application No. 62/782,933, filed on Dec. 20, 2018, provisional application No. 62/733,562, filed on Sep. 19, 2018, provisional application No. 62/733,558, filed on Sep. 19, 2018.

(51) Int. Cl.
| | | |
|---|---|---|
| *A61K 31/436* | (2006.01) | |
| *A61K 9/00* | (2006.01) | |
| *A61P 7/06* | (2006.01) | |
| *C07D 487/04* | (2006.01) | |
| *C07D 491/056* | (2006.01) | |

(52) U.S. Cl.
CPC .......... *A61K 31/436* (2013.01); *A61K 9/0053* (2013.01); *A61P 7/06* (2018.01); *C07D 487/04* (2013.01); *C07D 491/056* (2013.01)

(58) Field of Classification Search
CPC .. A61K 31/436; A61K 9/0053; A61K 9/2054; A61P 7/06; C07D 487/04; C07D 491/056
See application file for complete search history.

(56) References Cited

U.S. PATENT DOCUMENTS

| | | |
|---|---|---|
| 4,602,093 A | 7/1986 | Baldwin et al. |
| 4,918,073 A | 4/1990 | Ruger et al. |
| 5,030,631 A | 7/1991 | Bauer |
| 5,037,467 A | 8/1991 | Cho et al. |
| 5,059,605 A | 10/1991 | Clough et al. |
| 5,089,621 A | 2/1992 | Kim et al. |
| 5,091,384 A | 2/1992 | Kim et al. |
| 5,180,719 A | 1/1993 | White et al. |
| 5,250,544 A | 10/1993 | Lavielle et al. |
| 5,336,772 A | 8/1994 | Saiki et al. |
| 5,480,899 A | 1/1996 | Yano et al. |
| 5,672,601 A | 9/1997 | Cignarella |
| 5,714,625 A | 2/1998 | Hada et al. |
| 5,747,502 A | 5/1998 | Hanaoka et al. |
| 5,962,703 A | 10/1999 | Moszner et al. |
| 6,214,879 B1 | 4/2001 | Abraham et al. |
| 6,534,501 B2 | 3/2003 | Abraham et al. |
| 6,710,052 B2 | 3/2004 | Pease et al. |
| 6,878,715 B1 | 4/2005 | Klein et al. |
| 7,138,401 B2 | 11/2006 | Kasibhatla et al. |
| 7,160,885 B2 | 1/2007 | Currie et al. |
| 7,875,603 B2 | 1/2011 | Rathinavelu et al. |
| 8,501,953 B2 | 8/2013 | Salituro et al. |
| 8,552,050 B2 | 10/2013 | Cantley et al. |
| 8,692,001 B2 | 4/2014 | Becker et al. |
| 8,742,119 B2 | 6/2014 | Salituro et al. |

(Continued)

FOREIGN PATENT DOCUMENTS

| | | |
|---|---|---|
| CN | 101812063 A | 8/2010 |
| CN | 102206217 A | 10/2011 |

(Continued)

OTHER PUBLICATIONS

Clinical Trial Study—NCT04000165 "A Dose-Finding Study of AG-348 in Sickle Cell Disease", ClinicalTrials.gov, Jun. 27, 2019, 9 pages.

(Continued)

*Primary Examiner* — Eric Olson
*Assistant Examiner* — Samuel L Galster
(74) *Attorney, Agent, or Firm* — Jianjie Hu

(57) ABSTRACT

Compounds that activate pyruvate kinase R can be used for the treatment of sickle cell disease (SCD). Methods and compositions for the treatment of SCD are provided herein, including a therapeutic compound designated as Compound 1.

12 Claims, 51 Drawing Sheets

(56) References Cited

U.S. PATENT DOCUMENTS

| | | |
|---|---|---|
| 8,785,450 B2 | 7/2014 | Salituro et al. |
| 8,841,305 B2 | 9/2014 | Thomas et al. |
| 8,877,791 B2 | 11/2014 | Cantley et al. |
| 8,889,667 B2 | 11/2014 | Salituro et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,108,921 B2 | 8/2015 | Cianchetta et al. |
| 9,181,231 B2 | 11/2015 | Su |
| 9,221,792 B2 | 12/2015 | Salituro et al. |
| 9,248,199 B2 | 2/2016 | Metcalf |
| 9,328,077 B2 | 5/2016 | Salituro et al. |
| 9,394,257 B2 | 7/2016 | Ho et al. |
| 9,422,279 B2 | 8/2016 | Metcalf et al. |
| 9,458,132 B2 | 10/2016 | Cianchetta et al. |
| 9,458,139 B2 | 10/2016 | Xu et al. |
| 9,604,999 B2 | 3/2017 | Harris et al. |
| 9,708,267 B2 | 7/2017 | Boxer et al. |
| 9,744,145 B1 | 8/2017 | Liu et al. |
| 9,776,960 B2 | 10/2017 | Xu et al. |
| 9,802,900 B2 | 10/2017 | Li et al. |
| 9,957,250 B2 | 5/2018 | Metcalf et al. |
| 9,981,939 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,100,040 B2 | 10/2018 | Li et al. |
| 10,100,043 B2 | 10/2018 | Metcalf et al. |
| 10,208,052 B1 | 2/2019 | Zheng et al. |
| 10,266,551 B2 | 4/2019 | Li et al. |
| 10,315,991 B2 | 6/2019 | Xu et al. |
| 10,377,741 B2 | 8/2019 | Metcalf et al. |
| 10,435,393 B2 | 10/2019 | Xu et al. |
| 10,450,269 B1 | 10/2019 | Xu et al. |
| 10,472,371 B2 | 11/2019 | Zheng et al. |
| 10,493,035 B2 | 12/2019 | Dalziel et al. |
| 10,577,345 B2 | 3/2020 | Li et al. |
| 10,675,274 B2 | 6/2020 | Ericsson et al. |
| 10,683,285 B2 | 6/2020 | Li |
| 10,695,330 B2 | 6/2020 | Li et al. |
| 10,836,771 B2 | 11/2020 | Zheng et al. |
| 11,014,927 B2 | 5/2021 | Ericsson et al. |
| 11,071,725 B2 | 7/2021 | Ericsson et al. |
| 11,396,513 B2 | 7/2022 | Zheng et al. |
| 11,649,242 B2 | 5/2023 | Ericsson et al. |
| 11,844,787 B2 | 12/2023 | Ericsson et al. |
| 11,980,611 B2 | 5/2024 | Ericsson et al. |
| 2004/0077648 A1 | 4/2004 | Timmer et al. |
| 2004/0102458 A1 | 5/2004 | Chiosis et al. |
| 2005/0002861 A1 | 1/2005 | Krause et al. |
| 2005/0049263 A1 | 3/2005 | Kasibhatla et al. |
| 2005/0059663 A1 | 3/2005 | Martin et al. |
| 2005/0181305 A1 | 8/2005 | Shibuya |
| 2005/0256103 A1 | 11/2005 | Suzuki et al. |
| 2006/0074121 A1 | 4/2006 | Chen et al. |
| 2006/0211737 A1 | 9/2006 | Huang et al. |
| 2007/0015752 A1 | 1/2007 | Hangauer, Jr. |
| 2007/0270433 A1 | 11/2007 | Brinkman et al. |
| 2008/0058315 A1 | 3/2008 | Cai et al. |
| 2008/0184495 A1 | 8/2008 | Brun et al. |
| 2008/0253965 A1 | 10/2008 | Chiosis et al. |
| 2008/0269234 A1 | 10/2008 | Gandhi et al. |
| 2009/0042966 A1 | 2/2009 | Coleman et al. |
| 2009/0163545 A1 | 6/2009 | Goldfarb |
| 2009/0291921 A1 | 11/2009 | Jabri et al. |
| 2010/0029575 A1 | 2/2010 | Junien et al. |
| 2010/0120863 A1 | 5/2010 | Biftu et al. |
| 2010/0144594 A1 | 6/2010 | Zoller et al. |
| 2010/0144722 A1 | 6/2010 | Alexander et al. |
| 2010/0152157 A1 | 6/2010 | Puech et al. |
| 2010/0179154 A1 | 7/2010 | Almario Garcia et al. |
| 2010/0216774 A1 | 8/2010 | Bender et al. |
| 2010/0324030 A1 | 12/2010 | Dale et al. |
| 2011/0059089 A1 | 3/2011 | Swagemakers et al. |
| 2011/0085969 A1 | 4/2011 | Rollo et al. |
| 2011/0104054 A1 | 5/2011 | Chiosis et al. |
| 2012/0134979 A1 | 5/2012 | Xia et al. |
| 2012/0252818 A1 | 10/2012 | Chiosis et al. |
| 2013/0109684 A1 | 5/2013 | Blagg et al. |
| 2013/0116430 A1 | 5/2013 | Fujiwara et al. |
| 2013/0155489 A1 | 6/2013 | Kato et al. |
| 2013/0190315 A1 | 7/2013 | Metcalf et al. |
| 2013/0190316 A1 | 7/2013 | Metcalf et al. |
| 2014/0228360 A1 | 8/2014 | Duncan et al. |
| 2014/0242602 A1 | 8/2014 | Chiosis et al. |
| 2015/0246025 A1 | 9/2015 | Desai et al. |
| 2016/0106728 A1 | 4/2016 | Shen et al. |
| 2016/0200681 A1 | 7/2016 | Yu et al. |
| 2017/0121338 A1 | 5/2017 | Zhang et al. |
| 2017/0216434 A1 | 8/2017 | Hines et al. |
| 2017/0217964 A1 | 8/2017 | Li |
| 2018/0215765 A1 | 8/2018 | Di Giorgio et al. |
| 2018/0282369 A1 | 10/2018 | Desai et al. |
| 2019/0218221 A1 | 7/2019 | Zheng et al. |
| 2020/0031839 A1 | 1/2020 | Zheng et al. |
| 2020/0069643 A1 | 3/2020 | Ericsson |
| 2020/0085798 A1 | 3/2020 | Ericsson |
| 2020/0087309 A1 | 3/2020 | Lancia, Jr. |
| 2020/0129485 A1 | 4/2020 | Ericsson et al. |
| 2020/0253939 A1 | 8/2020 | Ericsson et al. |
| 2021/0017184 A1 | 1/2021 | Zheng et al. |
| 2021/0246143 A1 | 8/2021 | Ericsson et al. |
| 2022/0031671 A1 | 2/2022 | Ericsson et al. |
| 2022/0304987 A1 | 9/2022 | Ericsson et al. |
| 2022/0378755 A1 | 12/2022 | Luke et al. |
| 2022/0378756 A1 | 12/2022 | Ericsson et al. |
| 2024/0083901 A1 | 3/2024 | Ericsson et al. |
| 2024/0131011 A1 | 4/2024 | Luke et al. |

FOREIGN PATENT DOCUMENTS

| | | |
|---|---|---|
| CN | 102952139 A | 3/2013 |
| CN | 103570722 A | 2/2014 |
| CN | 104736534 A | 6/2015 |
| CN | 105037367 A | 11/2015 |
| CN | 105085528 A | 11/2015 |
| CN | 105153119 A | 12/2015 |
| CN | 105254628 A | 1/2016 |
| CN | 105294694 A | 2/2016 |
| CN | 105348286 A | 2/2016 |
| CN | 106928222 A | 7/2017 |
| CN | 109912610 A | 6/2019 |
| DE | 102008010661 A1 | 9/2009 |
| EP | 0007529 A1 | 2/1980 |
| EP | 0036711 A2 | 9/1981 |
| EP | 0264883 A2 | 4/1988 |
| EP | 0273534 A2 | 7/1988 |
| EP | 0338372 A2 | 10/1988 |
| EP | 0363212 A2 | 4/1990 |
| EP | 0378255 A2 | 7/1990 |
| EP | 0424850 A1 | 5/1991 |
| EP | 0424851 A1 | 5/1991 |
| EP | 0424852 A1 | 5/1991 |
| EP | 0486022 A2 | 5/1992 |
| EP | 0520277 A2 | 12/1992 |
| EP | 0590415 A2 | 4/1994 |
| EP | 0737670 A1 | 10/1996 |
| EP | 1096310 A2 | 5/2001 |
| EP | 1099692 A1 | 5/2001 |
| EP | 1249233 A1 | 10/2002 |
| EP | 1952800 A2 | 8/2008 |
| EP | 3141542 A1 | 3/2017 |
| EP | 2797416 B1 | 8/2017 |
| EP | 3483164 A1 | 5/2019 |
| IN | 1809/MUM/2013 | 5/2013 |
| IN | 2013/MU01809 | 3/2015 |
| JP | S 61 200544 | 9/1986 |
| JP | 3 13040 B2 | 2/1991 |
| JP | 3 275666 | 12/1991 |
| JP | 04 054181 A | 2/1992 |
| JP | 05125050 A | 5/1993 |
| JP | 05 196976 | 8/1993 |
| JP | 7 164400 | 6/1995 |

(56) References Cited

FOREIGN PATENT DOCUMENTS

| | | |
|---|---|---|
| JP | 1 110376 | 1/1999 |
| JP | 2001261653 A | 9/2001 |
| JP | 2003514673 | 4/2003 |
| JP | 2004175674 A | 6/2004 |
| JP | 2007246885 A | 9/2007 |
| JP | 2007328090 A | 12/2007 |
| JP | 2008031064 A | 2/2008 |
| JP | 2008063256 A | 3/2008 |
| JP | 2009149707 A | 7/2009 |
| JP | 2009212473 A | 9/2009 |
| JP | 2010192782 A | 9/2010 |
| JP | 2011246649 A | 12/2011 |
| JP | 2012188474 A | 10/2012 |
| JP | 2012188475 A | 10/2012 |
| JP | 2013171968 A | 9/2013 |
| KR | 20110096442 A | 8/2011 |
| LB | 11379 | 7/2018 |
| RU | 2517693 C2 | 4/2011 |
| RU | 2472794 C1 | 11/2012 |
| WO | WO 1993/011106 | 6/1993 |
| WO | WO 1993/022298 A1 | 11/1993 |
| WO | WO 1995/019353 A1 | 7/1995 |
| WO | WO 1998/038239 | 9/1998 |
| WO | WO 1998/050364 A1 | 11/1998 |
| WO | WO 1999/001442 A1 | 1/1999 |
| WO | WO 1999/002493 A1 | 1/1999 |
| WO | WO 1999/047489 A1 | 9/1999 |
| WO | WO 1999/047516 A1 | 9/1999 |
| WO | WO 1999/048461 A2 | 9/1999 |
| WO | WO 1999/048490 A1 | 9/1999 |
| WO | WO 1999/065895 A1 | 12/1999 |
| WO | WO 1999/065901 | 12/1999 |
| WO | WO 2000/004023 A1 | 1/2000 |
| WO | WO 2000/021951 A1 | 4/2000 |
| WO | WO 2000/053591 A1 | 9/2000 |
| WO | WO 2001/010842 A2 | 2/2001 |
| WO | WO 2001/032764 | 5/2001 |
| WO | WO 2001/043744 A1 | 6/2001 |
| WO | WO 2001/053288 A2 | 7/2001 |
| WO | WO 2001/057037 A2 | 8/2001 |
| WO | WO 2001/085728 A2 | 11/2001 |
| WO | WO 2002/030358 | 4/2002 |
| WO | WO 2002/034754 A2 | 5/2002 |
| WO | WO 2002/060902 A1 | 8/2002 |
| WO | WO 2002/076989 A1 | 10/2002 |
| WO | WO 2002/095063 A1 | 11/2002 |
| WO | WO 2003/015769 A1 | 2/2003 |
| WO | WO 2003/037860 A2 | 5/2003 |
| WO | WO 2003/063794 | 8/2003 |
| WO | WO 2003/067332 A2 | 8/2003 |
| WO | WO 2003/084948 A1 | 10/2003 |
| WO | WO 2004/002490 A2 | 1/2004 |
| WO | WO 2004/007770 A2 | 1/2004 |
| WO | WO 2004/009600 A1 | 1/2004 |
| WO | WO 2004/013144 A1 | 2/2004 |
| WO | WO 2004/014374 A1 | 2/2004 |
| WO | WO 2004/014382 | 2/2004 |
| WO | WO 2004/024676 A1 | 3/2004 |
| WO | WO 2004/080457 A1 | 9/2004 |
| WO | WO 2004/089470 A2 | 10/2004 |
| WO | WO 2004/089947 A2 | 10/2004 |
| WO | WO 2004/104000 A1 | 12/2004 |
| WO | WO 2005/000098 A2 | 1/2005 |
| WO | WO 2005/002577 A1 | 1/2005 |
| WO | WO 2005/009965 A1 | 2/2005 |
| WO | WO 2005/011653 A2 | 2/2005 |
| WO | WO 2005/011656 A2 | 2/2005 |
| WO | WO 2005/016915 A1 | 2/2005 |
| WO | WO 2005/023761 A2 | 3/2005 |
| WO | WO 2005/049570 | 6/2005 |
| WO | WO 2005/058869 | 6/2005 |
| WO | WO 2005/058870 | 6/2005 |
| WO | WO 2005/058871 | 6/2005 |
| WO | WO 2005/058873 | 6/2005 |
| WO | WO 2005/058874 | 6/2005 |
| WO | WO 2005/084667 A1 | 9/2005 |
| WO | WO 2005/094251 A2 | 10/2005 |
| WO | WO 2005/094834 A1 | 10/2005 |
| WO | WO 2005/103015 A1 | 11/2005 |
| WO | WO 2006/002100 A2 | 1/2006 |
| WO | WO 2006/009886 A1 | 1/2006 |
| WO | WO 2006/018279 A2 | 2/2006 |
| WO | WO 2006/018280 A2 | 2/2006 |
| WO | WO 2006/021448 A1 | 3/2006 |
| WO | WO 2006/023608 A2 | 3/2006 |
| WO | WO 2006/034315 A2 | 3/2006 |
| WO | WO 2006/038172 A1 | 4/2006 |
| WO | WO 2006/060122 A2 | 6/2006 |
| WO | WO 2006/084030 A2 | 8/2006 |
| WO | WO 2006/086445 A2 | 8/2006 |
| WO | WO 2006/099884 A1 | 9/2006 |
| WO | WO 2006/101521 A2 | 9/2006 |
| WO | WO 2006/110390 A1 | 10/2006 |
| WO | WO 2006/123121 A1 | 11/2006 |
| WO | WO 2006/130469 A1 | 12/2006 |
| WO | WO 2006/137485 A1 | 12/2006 |
| WO | WO 2007/006926 A2 | 1/2007 |
| WO | WO 2007/007069 A1 | 1/2007 |
| WO | WO 2007/019344 A1 | 2/2007 |
| WO | WO 2007/027734 A2 | 3/2007 |
| WO | WO 2007/042325 A1 | 4/2007 |
| WO | WO 2007/083119 A2 | 7/2007 |
| WO | WO 2007/087231 A2 | 8/2007 |
| WO | WO 2007/088123 A2 | 8/2007 |
| WO | WO 2007/097931 A2 | 8/2007 |
| WO | WO 2007/098418 A1 | 8/2007 |
| WO | WO 2007/126745 A2 | 11/2007 |
| WO | WO 2007/136603 A2 | 11/2007 |
| WO | WO 2007/138351 A2 | 12/2007 |
| WO | WO 2008/005937 A2 | 1/2008 |
| WO | WO 2008/019139 A2 | 2/2008 |
| WO | WO 2008/032905 A1 | 3/2008 |
| WO | WO 2008/057608 A2 | 5/2008 |
| WO | WO 2008/083027 A1 | 7/2008 |
| WO | WO 2008/094203 A2 | 8/2008 |
| WO | WO 2008/115719 A1 | 9/2008 |
| WO | WO 2008/120003 A1 | 10/2008 |
| WO | WO 2008/135141 A1 | 11/2008 |
| WO | WO 2008/139585 A1 | 11/2008 |
| WO | WO 2009/001126 A1 | 12/2008 |
| WO | WO 2009/004356 A1 | 1/2009 |
| WO | WO 2009/025781 A1 | 2/2009 |
| WO | WO 2009/025784 A1 | 2/2009 |
| WO | WO 2009/063244 A1 | 5/2009 |
| WO | WO 2009/077527 A1 | 6/2009 |
| WO | WO 2009/093032 A1 | 7/2009 |
| WO | WO 2009/112677 | 9/2009 |
| WO | WO 2009/121623 A2 | 10/2009 |
| WO | WO 2009/136889 A1 | 11/2009 |
| WO | WO 2009/153554 A1 | 12/2009 |
| WO | WO 2010/002802 A1 | 1/2010 |
| WO | WO 2010/021717 A2 | 2/2010 |
| WO | WO 2010/028761 A1 | 3/2010 |
| WO | WO 2010/042867 A2 | 4/2010 |
| WO | WO 2010/058318 A1 | 5/2010 |
| WO | WO 2010/092181 A1 | 8/2010 |
| WO | WO 2010/105243 A1 | 9/2010 |
| WO | WO 2010/108268 A1 | 9/2010 |
| WO | WO 2010/115688 A1 | 10/2010 |
| WO | WO 2010/118063 | 10/2010 |
| WO | WO 2010/129596 | 11/2010 |
| WO | WO 2010/132599 A1 | 11/2010 |
| WO | WO 2010/135524 A1 | 11/2010 |
| WO | WO 2010/151797 | 12/2010 |
| WO | WO 2011/002816 | 1/2011 |
| WO | WO 2011/002817 | 1/2011 |
| WO | WO 2011/025690 A1 | 3/2011 |
| WO | WO 2011/037793 A1 | 3/2011 |
| WO | WO 2011/050210 | 4/2011 |
| WO | WO 2011/050211 | 4/2011 |
| WO | WO 2011/060321 A1 | 5/2011 |
| WO | WO 2011/063055 A2 | 5/2011 |
| WO | WO 2011/103256 A1 | 8/2011 |
| WO | WO 2011/116282 A2 | 9/2011 |

(56) References Cited

FOREIGN PATENT DOCUMENTS

| | | |
|---|---|---|
| WO | WO 2011/137089 A1 | 11/2011 |
| WO | WO 2011/146358 A1 | 11/2011 |
| WO | WO 2012/002577 A1 | 1/2012 |
| WO | WO 2012/007861 A1 | 1/2012 |
| WO | WO 2012/007868 A2 | 1/2012 |
| WO | WO 2012/007877 A2 | 1/2012 |
| WO | WO 2012/019426 A1 | 2/2012 |
| WO | WO 2012/019427 A1 | 2/2012 |
| WO | WO 2012/056319 A1 | 5/2012 |
| WO | WO 2012/068096 A2 | 5/2012 |
| WO | WO 2012/071519 A1 | 5/2012 |
| WO | WO 2012/071684 A1 | 6/2012 |
| WO | WO 2012/080729 A2 | 6/2012 |
| WO | WO 2012/083246 | 6/2012 |
| WO | WO 2012/088314 | 6/2012 |
| WO | WO 2012/092426 A1 | 7/2012 |
| WO | WO 2012/092442 | 7/2012 |
| WO | WO 2012/092485 A1 | 7/2012 |
| WO | WO 2012/151440 A1 | 11/2012 |
| WO | WO 2012/151448 A1 | 11/2012 |
| WO | WO 2012/151450 A1 | 11/2012 |
| WO | WO 2012/151451 A1 | 11/2012 |
| WO | WO 2012/151452 A1 | 11/2012 |
| WO | WO 2012/160392 | 11/2012 |
| WO | WO 2012/160447 A1 | 11/2012 |
| WO | WO 2012/174126 | 12/2012 |
| WO | WO 2013/003249 A1 | 1/2013 |
| WO | WO 2013/003250 A1 | 1/2013 |
| WO | WO 2013/021054 A1 | 2/2013 |
| WO | WO 2013/038390 A1 | 3/2013 |
| WO | WO 2013/056153 | 4/2013 |
| WO | WO 2013/102142 A1 | 7/2013 |
| WO | WO 2013/102826 A1 | 7/2013 |
| WO | WO 2013/118805 A1 | 8/2013 |
| WO | WO 2013/126856 A1 | 8/2013 |
| WO | WO 2013/127266 A1 | 9/2013 |
| WO | WO 2013/155223 A1 | 10/2013 |
| WO | WO 2013/177224 A1 | 11/2013 |
| WO | WO 2013/184794 A2 | 12/2013 |
| WO | WO 2014/008458 A2 | 1/2014 |
| WO | WO 2014/014050 A1 | 1/2014 |
| WO | WO 2014/018355 A1 | 1/2014 |
| WO | WO 2014/023814 A1 | 2/2014 |
| WO | WO 2014/044356 A1 | 3/2014 |
| WO | WO 2014/048865 A1 | 4/2014 |
| WO | WO 2014/061031 A1 | 4/2014 |
| WO | WO 2014/062838 A2 | 4/2014 |
| WO | WO 2014/074848 | 5/2014 |
| WO | WO 2014/102817 A1 | 7/2014 |
| WO | WO 2014/118634 A1 | 8/2014 |
| WO | WO 2014/130890 A1 | 8/2014 |
| WO | WO 2014/139144 A1 | 9/2014 |
| WO | WO 2014/139325 A1 | 9/2014 |
| WO | WO 2014/139978 A1 | 9/2014 |
| WO | WO 2014/144715 A1 | 9/2014 |
| WO | WO 2014/150276 A1 | 9/2014 |
| WO | WO 2014/152588 A1 | 9/2014 |
| WO | WO 2014/172638 A2 | 10/2014 |
| WO | WO 2015/030514 A1 | 3/2015 |
| WO | WO 2015/036078 | 3/2015 |
| WO | WO 2015/042397 A1 | 3/2015 |
| WO | WO 2015/048336 A2 | 4/2015 |
| WO | WO 2015/051230 A1 | 4/2015 |
| WO | WO 2015/054555 A1 | 4/2015 |
| WO | WO 2015/078374 A1 | 6/2015 |
| WO | WO 2015/093948 A2 | 6/2015 |
| WO | WO 2015/116061 A1 | 8/2015 |
| WO | WO 2015/130915 A1 | 9/2015 |
| WO | WO 2015/144605 A1 | 10/2015 |
| WO | WO 2015/172732 A1 | 11/2015 |
| WO | WO 2015/183173 A1 | 12/2015 |
| WO | WO 2015/192701 A1 | 12/2015 |
| WO | WO 2016/005576 A1 | 1/2016 |
| WO | WO 2016/005577 A1 | 1/2016 |
| WO | WO 2016/014324 A1 | 1/2016 |
| WO | WO 2016/014522 A1 | 1/2016 |
| WO | WO 2016/021815 | 2/2016 |
| WO | WO 2016/044604 A1 | 3/2016 |
| WO | WO 2016/044629 A1 | 3/2016 |
| WO | WO 2016/044650 A1 | 3/2016 |
| WO | WO 2016/046837 A1 | 3/2016 |
| WO | WO 2016/047592 A1 | 3/2016 |
| WO | WO 2016/168647 A1 | 10/2016 |
| WO | WO 2016/181408 A2 | 11/2016 |
| WO | WO 2016/196816 | 12/2016 |
| WO | WO 2016/201227 A1 | 12/2016 |
| WO | WO 2017/006270 | 1/2017 |
| WO | WO 2017/050791 A1 | 3/2017 |
| WO | WO 2017/050792 A1 | 3/2017 |
| WO | WO 2017/191274 A2 | 11/2017 |
| WO | WO 2017/214002 A1 | 12/2017 |
| WO | WO 2018/049263 A1 | 3/2018 |
| WO | WO 2018/109277 A1 | 6/2018 |
| WO | WO 2018/175474 A1 | 9/2018 |
| WO | WO 2019/035863 A1 | 2/2019 |
| WO | WO 2019/035864 A1 | 2/2019 |
| WO | WO 2019/035865 A1 | 2/2019 |
| WO | WO 2019/099651 A1 | 5/2019 |
| WO | WO 2019/104134 | 5/2019 |
| WO | WO 2019/113359 | 6/2019 |
| WO | WO 2020/061252 | 3/2020 |
| WO | WO 2020/061255 | 3/2020 |
| WO | WO 2020/061261 | 3/2020 |
| WO | WO 2020/061378 | 3/2020 |
| WO | 2020139916 A1 | 7/2020 |
| WO | WO 2020/191022 | 9/2020 |

OTHER PUBLICATIONS

Kalfa, T.A et al., "Phase 1 Single (SAD) and Multiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", Blood, American Society of Hematology, Nov. 13, 2019, pp. 3, vol. 134.
Supplemental European Search Report for EP Application 20 86 4351, Aug. 2, 2023, 10 pages.
Abbady M.A., et al., Synthesis and biological activity of some new 4-(2-pyrazolin-3-yl)-, 4-(2-isoxazolin-e-yl)- and 4-(1,2,5,6-tetrahydro-2-thioxopyrimidin-4-yl)phenyl aminophenyl sulfides and sulfones., *Egyptian Journal of Pharmaceutical Sciences*, vol. 27, No. 1-4, (1986), Abstract Only.
Abraham DJ, Mehanna AS, Wireko FC, et al. "Vanillin, a potential agent for the treatment of sickle cell anemia." *Blood*. 1991;77(6):1334-41.
Adakveo [package insert]. East Hanover, New Jersey, Novartis Pharmaceuticals Corporation (Nov. 2019), 10 pgs.
Agios First Quarter 2020 Financial Results (Apr. 30, 2020), pp. 1-22.
Agrawal RK, Patel RK, Shah V, Nainiwal L, Trivedi B. "Hydroxyurea in sickle cell disease: drug review." *Indian J Hematol Blood Transfus*. Jun. 2014, 30(2):91-96.
Agrawal, R. K. et al., "Hydroxyurea in Sickle Cell Disease: Drug Review", *Indian J. Hematol Blood Transfus*, 30(2), pp. 91-96, (Apr.-Jun. 2014).
Aiuti, A. et al., Progress and prospects: gene therapy clinical trials (part 2), *Gene Ther*, 14(22): 1555-1563 (2007).
Al-Hakim, A.K et al., 14-3-3 cooperates with LKB1 to regulate the activity and localization of QSK and SIK, *Journal of Cell Science* 118 (23), pp. 5661-5673 (Aug. 2005).
Al-Hakim, A.K et al., "Control of AMPK-related kinases by USP9X and atypical Lys29/Lys33-linked polyubiquitin chains", *Biochemical Journal*, 411 (2), pp. 249-260, (Feb. 2008).
Alves-Filho, J.C. & Palsson-Mcdermott, E.M., Pyruvate Kinase M2: A Potential Target for Regulating Inflammation, *Frontiers in Immunology*, 7(145): Article 145 (2016).
Ambrus, J. et al., Studies on the vasoocclusive crisis of sickle cell disease. III. In vitro and in vivo effect of the pyrimido-pyrimidine derivative, RA-233: studies on its mechanism of action, *J Med*, 18(3-4):165-198 (1987).

(56) References Cited

OTHER PUBLICATIONS

Amer, J. et al., Red blood cells, platelets and polymorphonuclear neutrophils of patients with sickle cell disease exhibit oxidative stress that can be ameliorated by antioxidants, *British Journal of Haematology*, 132(1):108-113 (2006).

Andresen, C.A. et al., "Protein Interaction Screening for the Ankyrin Repeats and Suppressor of Cytokine Signaling (SOCS) Box (ASB) Family Identify Asb11 as a Novel Endoplasmic Reticulum Resident Ubiquitin Ligase", *The Journal of Biological Chemistry*, vol. 289, No. 4, pp. 2043-2054, (Jan. 24, 2014).

Ataga KI, Kutlar A, Kanter J, Liles D, Cancado R, Friedrisch J, Guthrie TH, Knight-Madden J, Alvarez OA, Gordeuk VR, Gualandro S, Colella MP, Smith WR, Rollins SA, Stocker JW, Rother RP. "Crizanlizumab for the prevention of pain crises in sickle cell disease." *N Engl J Med*. Feb. 2, 2017, 376(5):429-439.

Atkinson, Peter J., et al., 3,4-Dihydro-2H-benzoxazinones are 5-HT1A receptor antagonists with potent 5-HT reuptake inhibitory activity, *BioOrganic & Medicinal Chemistry Letters*, 15(3), pp. 737-741 (2005).

Austin, Nigel E., et al., "Novel 2,3,4,5-tetrahydro-1H-3-benzazepines with high affinity and selectivity for the dopamine D3 receptor", *BioOrganic & Medicinal Chemistry Letters*, 10(22), pp. 2553-2555, (2000).

Bailey, S.D. et al., "Variation at the NFATC2 Locus Increases the Risk of Thiazolidinedione-Induced Edema in the Diabetes Reduction Assessment with Ramipril and rosiglitazone Medication (DREAM) Study", *Diabetes Care*, vol. 33, No. 10, pp. 2250-2254, (Oct. 2010).

Bakshi N, Sinha CB, Ross D, Khemani K, Loewenstein G, Krishnamurti L. "Proponent or collaborative: Physician perspectives and approaches to disease modifying therapies in sickle cell disease." *PLoS One*. Jul. 20, 2017, 12(7):e0178413.

Balakin, Konstantin V. et al., Comprehensive Computational Assessment of ADME Properties using Mapping Techniques, *Current Drug Discovery Technologies*, 2(2), pp. 99-113 (2005).

Banerjee, S. et al., "Interplay between Polo kinase, LKB1-activated NUAK1 kinase, PP1ß phosphatase complex and the SCFß$^{TrCP}$ E3 ubiquitin ligase", *Biochem. J.* 461, pp. 233-245, (2014).

Banerjee, T. and Kuypers F.A., Reactive oxygen species and phosphatidylserine externalization in murine sickle red cells, *British Journal of Haematology*, 124:391-402 (2004).

Barbier AJ, Bodie S, Connor G, et al. "Safety, tolerability, pharmacokinetics and pharmacodynamics of multiple doses of AG-519, an allosteric activator of pyruvate kinase-R, in healthy subjects." *Blood*. 2016, 128:1264.

Barua, A.K., et al., Chemistry and Industry Communications to the Editor 1376 24 (Oct. 1970).

Bennett, Eric J., et al., "Dynamics of Cullin-RING Ubiquitin Ligase Network Revealed by Systematic Quantitative Proteomics", *Cell* 143, pp. 951-965, (Dec. 10, 2010).

Betz T, Lenz M, Joanny JF, Sykes C. "ATP-dependent mechanics of red blood cells." *Proc Natl Acad Sci USA*. 2009;106(36):15320-5.

Beutler, E. and Gelbart, T., "Estimating the prevalence of pyruvate kinase deficiency from the gene frequency in the general white population", *Blood*, 95(11): 3585-3588 (2000).

Bianchi, P. and Zanella, A., "Hematologically important mutations: red cell pyruvate kinase", (Third update), *Blood Cells Mol Dis.*, 26(1): 47-53 (2000).

Biftu, T et al., "Omarigliptin (MK-3102): A Novel Long-Acting DPP-4 Inhibitor for Once-Weekly Treatment of Type 2 Diabetes", *Journal of Medicinal Chemistry*, 57, pp. 3205-3212, (2014).

Bouwmeester, T. et al., "A physical and functional map of the human TNF-α/NF-κB signal transduction pathway", *Nature Cell Biology*, vol. 6, No. 2, pp. 97-105, (Feb. 2004).

Boxer, M.B. et al., "Evaluation of Substituted N,N$^1$-Diarylsulfonamides as Activators of the Tumor Cell Specific M2 Isoform of Pyruvate Kinase", *J. Med. Chem.*, 53: pp. 1048-1055 (2010).

Brajenovic, M. et al., "Comprehensive Proteomic Analysis of Human Par Protein Complexes Reveals an Interconnected Protein Network", *The Journal of Biological Chemistry*, vol. 275, No. 13, pp. 12804-12811 (Mar. 2004).

Brehme, M. et al., "Charting the molecular network of the drug target Bcr-Abl", *PNAS*, vol. 106, No. 18, pp. 7414-7419, (May 2009).

Bridges, C.R., et al., "USP9X deubiquitylating enzyme maintains RAPTOR protein levels, mTORC1 signalling and proliferation in neural progenitors", *Scientific Reports* 7:391, pp. 1-15, (Mar. 2017).

Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *Blood* (2020) 136 (Supplement 1):19-20, Nov. 4, 2020.

Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *ASH* 2020, Dec. 7, 2020.

Budzikiewicz, Herbert et al., "Vincetene, a benzopyrroloisoquinoline alkaloid, from Cynanchum vincetoxicum (L.) Pers. (Asclepiadaceae)", Liebigs Annalen Der Chemie, (8), pp. 1212-1231 (1979).

Buontempo P, Jubin RG, Buontempo C, Real R, Kazo F, O'Brien S, Adeel F, Abuchowski A. "Pegylated carboxyhemoglobin bovine (SANGUINATE) restores RBCs roundness and reduces pain during a sickle cell vaso-occlusive crisis." *Blood*. 2017, 130:969.

Cabrales, P. et al., "A look inside the mechanistic black box: Are red blood cells the critical effectors of RRx-001 cytotoxicity?", *Med Oncol.*, 33(7):63 (2016).

CAS Registry No. 1208929-16-1, Tert-Butyl 1H,2H,3H,4H,5H,6H-Pyrrolo[3,4-C]Pyrrole-2-Carboxylate Hydrochloride (Mar. 11, 2010).

Castilhos, L. et al., "Altered E-NTPDase/E-ADA activities and CD39 expression in platelets of sickle cell anemia patients", *Biomed Pharmacother.*, 79:241-246 (2016).

Castilhos, L. et al., "Increased oxidative stress alters nucleosides metabolite levels in sickle cell anemia", *Redox Rep.*, 22(6):451-459 (2017).

Castilhos, L. et al., "Sickle cell anemia induces changes in peripheral lymphocytes E- NTPDase/E-ADA activities and cytokines secretion in patients under treatment", *Biomedicine & Pharmacotherapy* 73 (2015), pp. 102-108.

Castro, O., Viability and function of stored sickle erythrocytes, *Transfusion*, 20(6):695-703 (1980).

Cazzola, M., Pyruvate kinase deficiency, Haematologica, 90(1): 1-2 (2005).

Charache, S. et al., Effect of 2,3-Diphosphateglycerate on oxygen affinity of blood in sickle, Cell Anemia, Journal of Clinical Investigation, 49(4):806-812 (1970).

Chaudhary, Neelam & Maddika, Subbareddy, "WWP2-WWP1 Ubiquitin Ligase Complex Coordinated by PPM1G Maintains the Balance Between Cellular p73 and ΔNp73 Levels", Mol. Cell. Biol. (Oct. 2014).

Chen, Yue et al.—Preclinical Pharmacokinetic/Pharmacodynamic Relationships for AG-348, An Investigational Small-Molecule Activator of Pyruvate Kinase, European Hematology Association, Jun. 13, 2015.

Cheung, Yiu-Yin et al., Solution-Phase Parallel Synthesis and SAR of Homopiperazinyl Analogs as Positive Allosteric Modulators of MGlu$_4$, ACS Comb Sci. 13(2), pp. 159-165, (Mar. 2011).

Chiosis et al., Development of a Purine-Scaffold Novel Class of Hsp90 Binders that Inhibit the Proliferation of Cancer Cells and Induce the Degradation of Her2 Tyrosine Kinase, BioOrganic & Medicinal Chemistry, vol. 10, Iss 11, (Nov. 2002), pp. 3555-3564.

Chiou WL, Barve A. "Linear correlation of the fraction of oral dose absorbed of 64 drugs between humans and rats." *Pharm Res*. Nov. 1998, 15(11):1792-5.

Chonat, S. et al., —Improvement in Red Blood Cell Physiology in Children With Sickle Cell Anemia Receiving Voxelotor—Childrens Healthcare of Atlanta (Dec. 2019).

(56) References Cited

OTHER PUBLICATIONS

Choudhury, N.R., et al., "RNA-binding activity of TRIM25 is mediated by its PRY/SPRY domain and is required for ubiquitination", BMC Biology 15:105, pp. 1-20, (2017).
Christensen, R.D. et al., Siblings with Severe Pyruvate Kinase Deficiency and a Complex Genotype, American Journal of Medical Genetics, Part A, (2016), pp. 2449-2452.
Chubukov V, Johnson K, Kosinski PA, et al. "Characterization of metabolic response to AG-348, an allosteric activator of red cell pyruvate kinase, in healthy volunteers and pyruvate kinase deficiency patients." Poster presented at: 58th American Society of Hematology Annual Meeting and Exposition; Dec. 4, 2016; San Diego, California. http://investor.agios.com/staticfiles/e1e9fd70-c84b-4472-bff3-bef0ecf05482 Accessed Jul. 28, 2017.
Chung, J.Y.L. et al., "Evolution of a Manufacturing Route to Omarigliptin, A Long-Acting DPP-4 Inhibitor for the Treatment of Type 2 Diabetes", Organic Process Research & Development, 19, pp. 1760-1768, (2015).
Clinical Trial Study—NCT02604433—U.S. National Library of Medicine, An Efficacy and Safety Study of Luspatercept (ACE-536) Versus Placebo in Adults Who Require Regular Red Blood Cell Transfusions Due to Beta (ß) Thalassemia (BELIEVE), Submitted Date: Nov. 13, 2015, 24 pgs.
Clinicaltrials.gov, NCT03815695, (v1)—U.S. National Library of Medicine, "A SAD/MAD to Assess the Safety, Pharmacokinetics and Pharmacodynamics of FT-4202 in Healthy Volunteers and Sickle Cell Disease Patients" (Jan. 22, 2019).
Clinical Trials Study, NCT03815695, (v2)—U.S. National Library of Medicine, "A SAD/MAD to Assess the Safety, Pharmacokinetics and Pharmacodynamics of FT-4202 in Healthy Volunteers and Sickle Cell Disease Patients," (Mar. 13, 2019) pp. 1-5.
Clinicaltrials.gov, NCT03815695, (v3)—U.S. National Library of Medicine, "A SAD/MAD to Assess the Safety, Pharmacokinetics and Pharmacodynamics of FT-4202 in Healthy Volunteers and Sickle Cell Disease Patients" (Sep. 16, 2019).
Clinical Trial Study—NCT03815695, (v4)—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 19, 2019 (v4), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 23, 2019 (v5), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 9, 2019 (v6), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 10, 2019 (v7), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Nov. 27, 2019 (v8), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 15, 2020 (v9 ), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 16, 2020 (v10), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Feb. 21, 2020 (v11), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Apr. 1, 2020, (v12), 12 pgs.
Clinicaltrials.gov, NCT03815695 (v13), "A SAD/MAD to Assess the Safety, Pharmacokinetics and Pharmacodynamics of FT-4202 in Healthy Volunteers and Sickle Cell Patients," Jun. 15, 2020.
Clinicaltrials.gov, NCT03815695 (v14), "A SAD/MAD to Assess the Safety, Pharmacokinetics and Pharmacodynamics of FT-4202 in Healthy Volunteers and Sickle Cell Patients," Jul. 17, 2020.
Clinicaltrials.gov, NCT03815695 (v15), "A SAD/MAD to Assess the Safety, Pharmacokinetics and Pharmacodynamics of FT-4202 in Healthy Volunteers and Sickle Cell Patients," Aug. 19, 2020.
Clinicaltrials.gov, NCT03815695 (v16), "A SAD/MAD to Assess the Safety, Pharmacokinetics and Pharmacodynamics of FT-4202 in Healthy Volunteers and Sickle Cell Patients," Sep. 1, 2020.
Clinicaltrials.gov, NCT03815695 (v17), "A SAD/MAD to Assess the Safety, Pharmacokinetics and Pharmacodynamics of FT-4202 in Healthy Volunteers and Sickle Cell Patients," Sep. 18, 2020.
Clinicaltrials.gov, NCT03815695 (v18), "A SAD/MAD to Assess the Safety, Pharmacokinetics and Pharmacodynamics of FT-4202 in Healthy Volunteers and Sickle Cell Patients," Oct. 15, 2020.
Clinicaltrials.gov, NCT03815695 (v19), "A SAD/MAD to Assess the Safety, Pharmacokinetics and Pharmacodynamices of FT-4202 in Healthy Volunteers and Sickle Cell Patients," Study Record Versions 19—Dec. 24, 2020.
Clinicaltrials.gov, NCT03815695 (v20), "A SAD/MAD to Assess the Safety, Pharmacokinetics and Pharmacodynamices of FT-4202 in Healthy Volunteers and Sickle Cell Patients," Study Record Versions 20, Jan. 8, 2021.
Clinicaltrials.gov, NCT04624659 (v1), "A Study of FT-4202 in Adults and Adolescents With Sickle Cell Disease," Study Record Version 1—Nov. 5, 2020.
Clinicaltrials.gov, NCT04624659 (v2), "A Study of FT-4202 in Adults and Adolescents With Sickle Cell Disease," Study Record Version 2—Nov. 10, 2020.
Clinicaltrials.gov, NCT04624659 (v3), "A Study of FT-4202 in Adults and Adolescents With Sickle Cell Disease," Study Record Versions 3—Dec. 10, 2020.
Clinicaltrials.gov, NCT04624659 (v4), "A Study of FT-4202 in Adults and Adolescents With Sickle Cell Disease," Study Record Versions 4, Dec. 28, 2020.
Clinicaltrials.gov, NCT04624659 (v5), "A Study of FT-4202 in Adults and Adolescents With Sickle Cell Disease," Study Record Versions 5, Jan. 7, 2021.
Clinicaltrials.gov, NCT04624659 (v6), "A Study of FT-4202 in Adults and Adolescents With Sickle Cell Disease," Study Record Versions 6, Jan. 14, 2021.
ClinicalTrials.gov, NCT04624659 (v7), "A Study of FT-4202 in Adults and Adolescents With Sickle Cell Disease," Study Record Versions 7, Feb. 8, 2021.
Cloutier, P. et al., "R2TP/Prefoldin-like component RUVBL1/RUVBL2 directly interacts with ZNHIT2 to regulate assembly of U5 small nuclear ribonucleoprotein", Nature Communications, pp. 1-14 (May 2017).
Cole, D.C. et al., Conformationally Constrained N1-arylsulfonyltryptamine derivatives as 5-HT6 receptor antagonists, BioOrganic & Medicinal Chemistry Letters, vol. 15, No. 21, (Nov. 1, 2005), pp. 4780-4785.
Cox, J.L., et al., "The SOX2-Interactome in Brain Cancer Cell Identifies the Requirement of MSI2 and USP9X for the Growth of Brain Tumor Cell", PLOS ONE, vol. 8, Issue 5, pp. 1-13, (May 2013).
Croasdell, G., European Hematology Association—20th Annual Congress (Jun. 11-14, 2015—Vienna, Austria) Meeting Report, Drugs of Today (2015), 51(7),1 pp. 441-445.

(56) References Cited

OTHER PUBLICATIONS

Das, A et al., "USP9X counteracts differential ubiquitination of NPHP5 by MARCH7 and BBS11 to regulate ciliogenesis", PLOS Genetics, pp. 1-24, (May 12, 2017).
Davis, Z.H., et al., "Global Mapping of Herpesvirus-Host Protein Complexes Reveals a Transcription Strategy for Late Genes", Molecular Cell 57, pp. 349-360; (Jan. 22, 2015).
De Furia, F. et al., The effects of cyanate in vitro on red blood cell metabolism and function in sickle cell anemia, J Clin Invest., 51(3):566-574 (1972).
De Jong, K. and Kuypers, F., Sulphydryl modifications alter scramblase activity in murine sickle cell disease, British Journal of Haematology, 133(4):427-432 (2006).
De Rosa MC, Carelli Alinovi C, Galtieri A, Russo A, Giardina B. "Allosteric properties of hemoglobin and the plasma membrane of the erythrocyte: New insights in gas transport and metabolic modulation." IUBMB Life. 2008, 60(2):87-93.
Diez, A. et al., Life-threatening nonspherocytic hemolytic anemia in a patient with a null mutation in the PKLR gene and no compensatory PKM gene expression, Blood, 106:1851 (2005).
Diez-Silva M, Dao M, Han J, Lim CT, Suresh S. "Shape and biomechanical characteristics of human red blood cells in health and disease." MRS Bull. May 2010, 35(5):382-8.
Drissi, R. et al., "Quantitative Proteomics Reveals Dynamic Interactions of the Mini chromosome Maintenance Complex (MCM) in the Cellular Response to Etoposide Induced DNA Damage", Molecular & Cellular Proteomics, pp. 2002-2013, (2015).
DROXIA [package insert]. Princeton, New Jersey, Bristol-Myers Squibb Company, (Dec. 2017), 28 pgs.
DROXIA [package insert]. Princeton, New Jersey, Bristol-Myers Squibb Company (Dec. 2019), 25 pgs.
Dupont, S. et al., "FAM/USP9x, a Deubiquitinating Enzyme Essential for TGFß Signaling, Controls Smad4 Monoubiquitination", Cell, 136, pp. 123-135, (Jan. 9, 2009).
Dzandu JK, Johnson RM. "Membrane protein phosphorylation in intact normal and sickle cell erythrocytes." J Biol Chem. Jul. 10, 1980, 255(13):6382-6.
El-Sharief, A.M., et al., Some halogenated sulfonamides with biological interest, Journal of the Indian Chemical Society, vol. 61, No. 6, (1984), pp. 537-543.
Emam, H.A., et al., Heterocyclization of sulfamido chalcones to pyrazoline, cyanopyridone, nicotinonitrile and hydrobenzo [1,2-c] pyrazole derivatives, Journal of the Serbian Chemical Society, vol. 62, No. 7, (1997), Abstract only.
ENDARI [package insert]. Torrance, California: Emmaus Medical, Inc., (Jul. 2017), 8 pgs.
ENDARI [package insert]. Torrance, California, Emmaus Medical, Inc., (Nov. 2019), 10 pgs.
Ernst, A. et al., "A Strategy for Modulation of Enzymes in the Ubiquitin System", Science, 339, pp. 1-15, (Feb. 2013).
Estepp, et al., Phase 1 Single (SAD) and Multiple Ascending Dose (MAD) Study of the Safety, Pharmacokinetics (PK) and Pharmacodynamics (PD) of FT-4202, A PKR-Activator, In Healthy and Sickle Cell Disease Subjects, Abstract, e-Poster, European Hematology Association Open Access Library, Presentation EHA25, (May 14, 2020), 2 pgs.
Estepp, et al., Phase 1 Single (SAD) and Multiple Ascending Dose (MAD) Study of the Safety, Phyarmacokinetics (PK) and Pharmacodynamics (PD) of FT-4202, a PKR Activator, in Healthy and Sickle Cell Disease Subjects, Poster, EP1531, (Jun. 12, 2020), 1 pg.
Estepp, J.H. et al., A clinically meaningful fetal hemoglobin threshold for children with sickle cell anemia during hydroxyurea therapy, Am J Hematol., 92:1333-1339 (2017).
Estepp, Jeremie H., et al., "Phase 1 Single (SAD) and Multiple Ascending Dose (MAD) Study of the Safety, Pharmacokinetics (PK) and Pharmacodynamics (PD) of FT-4202, a PKR Activator, in Healthy Volunteers and Patients with Sickle Cell Disease," Virtual meeting [poster EP1531] presented at the 25th Congress of the European Hematology Association; Jul. 11-21, 2020.

European Hematology Association HemaSphere Abstract Book, 15th Annual Sickle Cell & Thalassaemia & 1st EHA European Sickle Cell Conference, Oct. 26-31, 2020.
Fioravanti, R., et al., Synthesis and Biological Evaluation of N-substituted -3, 5- diphenyl-2-pyrazoline derivatives as cyclooxygenase (COX-2) inhibitors, European Journal of Medicinal Chemistry, vol. 45, No. 12, (Dec. 1, 2010), pp. 6135-6138, XP027526583.
Fitch, R. W et al., Phantasmidine: An Epibatidine Congener from the Ecuadorian Poison Frog Epipedobates anthonyi', Journal of Natural Products (2010), vol. 73, No. 3, pp. 331-337.
Fleischhacker, W., et al., "Heterocyclic fused naphthalene systems from thebaine. 1", Liebigs Annalen Der Chemie, (5), pp. 844-851, (1983).
Fogeron, M.L. et al., "LGALS3BP regulates centriole biogenesis and centrosome hypertrophy in cancer cells", Nature Communications, 4:1531, pp. 1-14; (2013).
Forma Therapeutics, Press Release, "Forma Therapeutics Presents Clinical Proof-of-Concept Data at the 62nd Annual ASH Meeting Supporting the Potential of its Novel Investigational PKR Activator, FT-4202, to Treat Sickle Cell Disease (SCD)" (Dec. 7, 2020).
Forma Therapeutics, Inc., Press Release—"Forma Therapeutics Announces Positive FT-4202 600 mg Multiple Ascending Dose Cohort Data Supporting the Doses Being Evaluated in Phase 2/3 Registrational Trial, Called the Hibiscus Study", Mar. 30, 2021—2 pgs.
Frost, David A., et al., "Naturally occurring compounds related to phenalenone. V. Synthetic approaches to structures based on 8,9-dihydro-8,8,9-trimethylphenaleno [1,2-b] furan-7-one", Journal of the Chemical Society, Perkin Transactions 1: Organic and Bio-Organic Chemistry (1972-1999), pp. 2159-2169.
Gaudet, P. et al., "Phylogenetic-based propagation of functional annotations within the Gene Ontology consortium", vol. 12, No. 5, pp. 449-462; (Aug. 2011).
Giannone, R.J., et al., "The Protein Network Surrounding the Human Telomere Repeat Binding Factors TRF1, TRF2, and POT1", PLOS One, vol. 5, Issue 8, pp. 1-10, (Aug. 2010).
Gizi, A. et al., Assessment of oxidative stress in patients with sickle cell disease: The glutathione system and the oxidant-antioxidant status, Blood Cells Mol Dis., 46(3):220-225 (2011).
Gladwin, M., Adenosine recepter crossroads in sickle cell disease, Nature Medicine, 17(1):38-40, (2011).
Glombitza, S .et al., Adenosine causes cAMP-dependent activation of chick embryo red cell carbonic anhydrase and 2,3-DPG synthesis, American Journal of Physiology, 271(4):973-81 (1996).
Gomez-Bougie, P. et al., "Noxa controls Mule-dependent Mcl-1 ubiquitination through the regulation of the Mcl-1/USP9X interaction", Biochemical and Biophysical Research Communications 413, pp. 460-464, (2011).
Goncharov, T. et al., "OTUB1 modulates c-IAP1 stability to regulate signaling pathways", The EMBO Journal 32, No. 8, pp. 1103-1114, (2013).
Grace RF, Rose C, Layton DM, Yaish HM, Barcellini W, Galactéros F, Morton DH, Ravindranath Y, Kuo KHM, van Beers EJ, Kwiatkowski JL, Silver BA, Merica E, Kung C, Cohen M, Yang H, Hixon J, Kosinski PA, Silver L, Dang L, Yuan Z, Barbier AJ, Glader B. "Effects of AG_348, a pyruvate kinase activator, on anemia and hemolysis in patients with pyruvate kinase deficiency: Data from the DRIVE PK study". Blood. 2016, 128:402.
Grace, et al., Safety and Efficacy of Mitapivat in Pyruvate Kinase Deficiency, N. Engl. J. Med. 381, 10, (Sep. 5, 2019), p. 933-944.
Grasso, D. et al., "Zymophagy, a Novel Selective Autophagy Pathway Mediated by VMP1-USP9x-p62, Prevents Pancreatic Cell Death", The Journal of Biological Chemistry, vol. 286, No. 10, pp. 8308-8324, (Mar. 2011).
Greco, T.M. et al., "Nuclear Import of Histone Deacetylase 5 by Requisite Nuclear Localization Signal Phosphorylation", Molecular & Cellular Proteomics 10: , pp. 1-15, (2011).
Grou, C.P., et al., "Identification of ubiquitin-specific protease 9X (USP9X) as a deubiquitinase acting on the ubiquitin-peroxin 5 (PEX5) thioester conjugate", J. Biol. Chem., pp. 1-24; (Feb. 27, 2012).

(56) References Cited

OTHER PUBLICATIONS

Habata, S. et al., "BAG3-mediated Mcl-1 stabilization contributes to drug resistance via interaction with USP9X in ovarian cancer", International Journal of Oncology 49: pp. 402-410, (2016).
Han, K.J. et al., "Ubiquitin-specific Protease 9x Deubiquitinates and Stabilizes the Spinal Muscular Atrophy Protein—Survival Motor Neuron", J. Biol. Chem., pp. 1-22, (Oct. 2012).
Hanson, D. et al., "Identifying biological pathways that underlie primordial short stature using network analysis", Journal of Molecular Endocrinology, pp. 333-344, (2014).
Harada, R. et al., "Structure of pristimerine, a quinonoid triterpene", Tetrahedron Letters, pp. 603-607, (1962).
Harayama, Takashi et al., "Novel synthesis of naphthobenzazepines from N-bromobenzylnaphthylamines by regioselective C-H activation utilizing the intramolecular coordination of an amine to Pd", Synlett, (8), pp. 1141-1144, (2003).
Hauri, S. et al., "Interaction proteome of human Hippo signaling: modular control of the co-activator YAP1", Molecular Systems Biology, 9: 713, pp. 1-16 (Nov. 2013).
Havugimana, P. et al., "A Census of Human Soluble Protein Complexes", Cell 150, pp. 1068-1081, (Aug. 2012).
Hebbel RP, Eaton JW, Balasingam M, Steinberg MH. "Spontaneous oxygen radical generation by sickle erythrocytes." J Clin Invest. 1982, 70(6):1253-9.
Hein, M.Y., et al., "A Human Interactome in Three Quantitative Dimensions Organized by Stoichiometries and Abundances", Cell 163, pp. 712-723, (Oct. 2015).
Hierso, R. et al., Effects of oxidative stress on red blood cell rheology in sickle cell patients, British Journal of Haematology, 166(4):601-606 (2014).
Homan, C.C. et al., "Mutations in USP9X Are Associated with X-linked Intellectual Disability and Disrupt Neuronal Cell Migration and Growth", The American Journal of Human Genetics 94, pp. 470-478, (Mar. 2014).
Hoppe CC, Inati AC, Brown C, et al. "Initial results from a cohort in a phase 2a study (GBT440-007) evaluating adolescents with sickle cell disease treated with multiple doses of GBT440, a HbS polymerization inhibitor." Blood. 2017:130(Suppl 1): 689.
Husain, M.I., et al., Synthesis of some new N-[4-(acetyl/phenyl-5-arylpyrazolin-3-yl)phenyl]arylsulfonamides as oral hypoglycemic agents, Indian Drugs, vol. 24, No. 4, (1987), Abstract only.
Huttlin, E. L., et al., "The BioPlex Network: A Systematic Exploration of the Human Interactome", Cell 162, pp. 425-440, (Jul. 2015).
Huttlin, E.L., et al., "Architecture of the human interactome defines protein communities and disease networks", Nature, pp. 1-35, (May 2017).
HYDREA [package insert]. Princeton, New Jersey, Bristol-Myers Squibb Company (Jul. 2019), 29 pgs.
Imamura K, Tanaka T. "Multimolecular forms of pyruvate kinase from rat and other mammalian tissues. I Electrophoretic studies." J Biochem. 1972, 71:1043-51.
Imamura K, Tanaka T. "Pyruvate kinase isozymes from rat." Methods Enzymol. 1982, 90:150-65.
International Search Report and Written Opinion for PCT/US2019/051831, dated Dec. 6, 2019 (Dec. 6, 2020).
International Search Report and Written Opinion for PCT/US2020/051645, dated Dec. 7, 2020 (Dec. 7, 2020).
International Search Report and Written Opinion for PCT/US2020/051579, dated Dec. 10, 2020 (Dec. 10, 2020).
International Search Report and Written Opinion for PCT/US2019/052024, dated Dec. 23, 2019 (Dec. 23, 2019).
International Search Report and Written Opinion for PCT/US2018/023405, dated Jun. 5, 2018 (Jun. 5, 2018).
Iwasaki, Tameo et al., "Novel Selective PDE IV Inhibitors as Antiasthmatic Agents. Synthesis and Biological Activities of a Series of 1-Aryl-2,3-bis (hydroxymethyl) naphthalene Lignans", Journal of Medicinal Chemistry (1996), pp. 2696-2704.

Jendralla, H. et al., Synthesis of 1,2,3,4,5,6-Hexahydropyrrolo[3,4-c]pyrrole dihydrobromide and 1,2,3,5-Tetrahydro-2-[(4-Methyl-Phenyl) Sulfonyl]Pyrrolo[3,4-c]Pyrrole, Heterocycles, 41(6): 1291-1298 (1995).
Jin, Y. et al., Effects of gamma irradiation on red cells from donors with sickle cell trait, Transfusion, 37(8):804-808 (1997).
Johansen, L.D., et al., "IKAP localizes to membrane ruffles with filamin A and regulates actin cytoskeleton organization and cell migration", Journal of Cell Science 121, pp. 854-864, (Dec. 2007).
Jones, M.H., et al., "The *Drosophila* developmental gene fat facets has a human homologue in Xp11.4 which escapes X-inactivation and has related sequences on Yq11.2", Human Molecular Genetics, vol. 5, No. 11, pp. 1695-1701, (Aug. 1996).
Jorgensen, Eugene C., et al., "Thyroxine analogs. 20. Substituted 1-and 2-naphthyl ethers of 3,5-diiodotyrosine", Journal of Medicinal Chemistry 14(11), pp. 1023-1026, (1971).
Joshi, B., et al., Indian J. Chem., Sect. B (1983), 22B(2), Abstract only. Chemical Abstract No. 99:105146.
Joshi, P., et al., "The functional interactome landscape of the human histone deacetylase family", Molecular Systems Biology 9, 672, (2013).
Kalai, T. et al., Synthesis of Pyrroline Nitroxide Annulated Carbocycles and Heterocycles, Synthesis No. 6, pp. 831-837 (2000).
Kalfa, et al., FORMA Therapeutics, Inc., Watertown, MA, Power Pointe Presentation, Dated Nov. 6, 2019 , Phase 1 Single and Multiple Ascending Dose Study of the Safety, Tolerability, Pharmacokinetics and Pharmacodynamics of FT-4202, an Allosteric activator of Pyruvate Kinase-R, in Healthy and Sickle Cell Disease Subjects, 15 pgs.
Kalfa, T. A. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", JSCDH-D-20-0053, vol. VII, Pub. Date: Jun. 12, 2020; pp. 83-84.
Kalfa, T. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", 14th Annual Sickle Cell Disease Research and Educational Symposium/43rd National Sickle Cell Disease Scientific Meeting (Sep. 23-25, 2020).
Kalfa, T.A. et al., "616 Phase 1 Single (SAD) and Julotiple Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", (Nov. 2019).
Kaltenbach, L.S., et al., "Huntingtin Interacting Proteins Are Genetic Modifiers of Neurodegeneration", PLOS Genetics, vol. 3, Issue 5, pp. 689-708, (May 2007).
Kasturi, Tirumalai R., et al., "Reactions of tetrahalo-1,2-benzoquinones. III. Reaction of tetrachloro-1,2-benzoquinone withtetralones and naphthols: pathway to the condensates", Journal of the Chemical Society C: Organic, (9), pp. 1257-1259, (1970).
Katzenellenbogen, R.A., et al., "NFX1-123 and Poly(A) Binding Proteins Synergistically Augment Activation of Telomerase In Human Papillomavirus Type 16 E6-Expressing Cells", Journal of Virology, vol. 81, pp. 3786-3796, (Apr. 2007).
Khafagy, M.M., Synthesis of some pyrimidine and pyrazoline derivatives, Al-Azhar Bulletin of Science, vol. 3, No. 1, (1992), Abstract only.
Kharalkar, S.S. et al., Identification of Novel Allosteric Regulators of Human-Erythrocyte Pyruvate Kinase, Chemistry & Biodiversity, vol. 4, pp. 2603-2617 (Feb. 2007).
Kim H, Kosinski P, Kung C, Dang L, Chen Y, Yang H, Chen YS, Kramer J, Liu G. "A fit-for-purpose LC-MS/MS method for the simultaneous quantitation of ATP and 2,3-DPG in human K2EDTA whole blood." J Chromatogr B Analyt Technol Biomed Life Sci. Sep. 1, 2017, 1061-1062:89-96.
Kim J, Lee H, Shin S. "Advances in the measurement of red blood cell deformability: A brief review." J Cell Biotech. 2015;1:63-79.
Kim, M., et al., "Role of Angiomotin-like 2 mono-ubiquitination on YAP inhibition", EMBO reports, vol. 17, No. 1., pp. 64-78, (Nov. 23, 2015).

(56) References Cited

OTHER PUBLICATIONS

Kimura, K., et al., "Diversification of transcriptional modulation: Large-scale identification and characterization of putative alternative promoters of human genes", Genome Research 16, pp. 55-65, (2006).
Kirli, K., et al., "A deep proteomics perspective on CRM1-mediated nuclear export and nucleocytoplasmic partitioning", eLife, pp. 1-28; (2015).
Knauff, E.A.H., et al., "Genome-wide association study in premature ovarian failure patients suggests ADAMTS19 as a possible candidate gene", Human Reproduction, vol. 24, No. 9, pp. 2372-2379, (2009).
Kodama, K. et al., Solvent-induced dual chirality switching in the optical resolution of tropic acid via diastereomeric salt formation with (1R,2S)-2-amino-1,2-diphenylethanol, Tetrahedron 70:7923-7928 (2014).
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Blood (2020) 136 (Supplement1):23-24, Nov. 4, 2020.
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Presented at the $62^{nd}$ American Society of Hematology (ASH) Annual Meeting, Dec. 5, 2020.
Kristensen, A.R., Gsponer, J. and Foster, L.J., "A high-throughput approach for measuring temporal changes in the interactome", Nat Methods, 9(9), pp. 1-12, (2012).
Kuehl, G. et al., In vitro interactions of 51Cr in human red blood cells and hemolysates, Vox Sang., 40(4):260-272 (1981).
Kung C, Hixon J, Kosinski PA, et al. "AG-348 enhances pyruvate kinase activity in red blood cells from patients with pyruvate kinase deficiency." Blood. 2017;130(11):1347-1356.
Kurita, R. et al., Establishment of Immortalized Human Erythroid Progenitor Cell Lines Able to Produce Enucleated Red Blood Cells, PLOS ONE, vol. 8, Iss.3, pp. 1-15 (Mar. 2013).
Kushwaha, D., et al., "USP9X inhibition promotes radiation-induced apoptosis in non-small cell lung cancer cells expressing mid-to-high MCL1", Cancer Biology & Therapy 16:3, pp. 392-401, (Mar. 2015).
Kwasna, D., et al., "Discovery and Characterization of ZUFSP/ZUP1, a Distinct Deubiquitinase Class Important for Genome Stability", Molecular Cell 70, pp. 150-164, (2018).
Le Quesne, P.W. et al., One-Step Preparation of Tetrakis(bromomethyl)ethylene from Pinacolyl Alcohol, J. Org. Chem., 40(1): 142-143 (1975).
Le, Kha et al., Population pharmacokinetics and pharmacodynamics of AG-519, a pyruvate kinase activator for the treatment of pyruvate kinase deficiency, in human healthy volunteers, Agios Pharma—1263 Poster, —58th American Society of Hematology Annual Meeting and Exposition, Dec. 3-6, 2016—San Diego, CA.
Le, Kha et al., Population pharmacokinetics and pharmacodynamics of AG-348 in healthy human volunteers guide dose selection for the treatment of pyruvate kinase deficiency, Agios Pharma—3336 Poster,—57th American Society of Hematology Annual Meeting and Exposition, Dec. 5-8, 2015—Orlando, FL.
Lehrer-Graiwer J, Howard J, Hemmaway CJ, et al. "Long-term dosing in sickle cell disease subjects with GBT440, a novel HbS polymerization inhibitor." Blood, 2016:128(22): 2488.
Lehrer-Graiwer, Josh et al., Long-Term Dosinig in Sickle Cell Disease Subjects with GBT440, a Novel HbS Polymerization Inhibitor, blood, 114, Hemoglobinopathies, Excluding Thalassemia- Clinical Poster II, Dec. 2, 2016.
Lenihan, J.A., Saha, Orthis, and Young p. W., "Proteomic analysis reveals novel ligands and substrates for LNX1 E3 ubiquitin ligase", PLOS ONE, pp. 1-18; (Nov. 2017).
Li, X., et al., "Defining the protein-protein interaction network of the human protein tyrosine phosphatase family", The American Society for Biochemistry and Molecular Biology, Inc., pp. 1-54, (2016).
Litinov RI, Weisel JW. "Role of red blood cells in haemostasis and thrombosis." ISBT Sci Ser. Feb. 2017, 12(1):176-183.
Liu, X.H., et al., European Journal of Cancer, vol. 31A, No. 6, pp. 953-963, (1995).
Llauger et al., "Evaluation of 8-Arylsulfanyl, 8-Arylsulfoxyl, and 8-Arylsulfonyl Adenine Derivatives as Inhibitors of the Heat Shock Protein 90", J. Med. Chem., 48 (8), pp. 2892-2905, (Mar. 25, 2005).
Llauger et al., "Synthesis of 8-arylsulfoxyl/sulfonyl adenines", Tetrahedron Letters, vol. 45, Issue 52, (Dec. 20, 2004), pp. 9549-9552.
Lochmatter, C. et al., Integrative phosphoproteomics links IL-23R signalling with metabolic adaption in lymphocytes, Scientific Reports, 6:24491 (2016).
Lockwood, S. et al., Endothelium-derived nitric oxide production is increased by ATP released from red blood cells incubated with hydroxyurea, Nitric Oxide, 38:1-7 (2014).
Loriga G. et al., Synthesis of 3,6-diazabicyclo [3.1.1]heptanes as novel ligands for the opioid receptors, Bioorganic & Medicinal Chemistry, Pergamon, GB, vol. 14, No. 3, pp. 676-691, (Feb. 1, 2006).
Lu, L., et al., "The HECT Type Ubiquitin Ligase NEDL2 Is Degraded by Anaphase-promoting Complex/Cyclosome (APC/C)-Cdh1, and Its Tight Regulation Maintains the Metaphase to Anaphase Transition", The Journal of Biological Chemistry, vol. 288, No. 50, pp. 35637-35650; (Dec. 2013).
Lucas, et al., "Facile Synthesis of a Library of 9-Alkyl-8-benzyl-9H-purin-6-ylamine Derivatives", J. Comb. Chem., 3 (6), pp. 518-520, (Sep. 21, 2001).
MacDonald, Gregor J., et al., "Design and Synthesis of trans-3-(2-(4-((3-(3-(5-Methyl-1,2,4-oxadiazolyl))-phenyl(carboxamido)cyclohexyl)ethyl)-7-methylsulfonyl-2,3,4,5-tetrahydro-1H-3-benzazepine (SB-414796): A Potent and Selective Dopamine D3 Receptor Antagonist", Journal of Medicinal Chemistry, 46(23), pp. 4952-4964 (2003).
Macdonald, Rosemary, Red cell 2,3-diphosphoglycerate and oxygen affinity, Anaesthesia, vol. 32, pp. 544-553, (1977).
Martinez-Mayorga Karina et al., Ligand/kappa-opioid receptor interactions: Insights from the X-ray crystal structure, European Journal of Medicinal Chemistry, vol. 66, pp. 114-121 (May 30, 2013).
Mathe-Allainmat, Monique et al., "Synthesis of 2-Amido-2, 3-dihydro-1H-phanalene Derivatives as New Conformationally Restricted Ligands for Melatonin Receptors", Journal of Medicinal Chemistry, 39(16), pp. 3089-3095, (1996).
McCluskey A., et al., BioOrganic & Medicinal Chemistry Letters 10 (2000), pp. 1687-1690.
McCluskey A., et al., Bioorganic & Medicinal Chemistry Letters 11 (2001), pp. 2941-2946.
McGarry, E., et al., "The deubiquitinase USP9X maintains DNA replication fork stability and DNA damage checkpoint responses by regulating CLASPIN during S-phase", Cancerres.aacrjournals.org, pp. 1-39; (2016).
Metcalf B, Chuang C, Dufu K, et al. "Discovery of GBT440, an orally bioavailable R-state stabilizer of sickle cell hemoglobin." ACS Med Chem Lett. 2017; 8(3):321-326.
Meza, N.W. et al., In vitro and in vivo expression of human erythrocyte pyruvate kinase in erythroid cells: a gene therapy approach, Hum Gene Ther, 18(6):502-514 (2007).
Middelkoop, E. et al., Studies on sickled erythrocytes provide evidence that the asymmetric distribution of phosphatidylserine in the red cell membrane is maintained by both ATP- dependent translocation and interaction with membrane skeletal proteins, Biochimica et Biophysica Acta, 937:281-288 (1988).
Misra H. Bainbridge J, Berryman J, Abuchowski A, Galvez KM, Uribe LF, Hernandez AL, Sosa NR. "A phase 1b open label, randomized, safety study of SANGUINATE™ in patients with sickle cell anemia." Rev Bras Hematol Hemoter. Jan.-Mar. 2017 39(1):20-7.

(56) References Cited

OTHER PUBLICATIONS

Miwa, S. and Fujii, H., Molecular basis of erythroenzymopathies associated with hereditary hemolytic anemia: tabulation of mutant enzymes, Am J Hematol., 51(2): 122-132 (1996).

Moehrle, H., et al., "1,2,3,4-Tetrahydroquinolines as substrates for Mannich compounds", Chemical Sciences, 53(7), pp. 742-752; (1998).

Moriyama R, Lombardo CR, Workman RF, Low PS. "Regulation of linkages between the erythrocyte membrane and its skeleton by 2,3-diphosphoglycerate." J Biol Chem. May 25, 1993, 268(15):10990-6.

Mouchantaf, R., et al., "The Ubiquitin Ligase Itch Is Auto-ubiquitylated in Vivo and in Vitro but Is Protected from Degradation by Interacting with the Deubiquitylating Enzyme FAM/USP9X", The Journal of Biological Chemistry, vol. 281, No. 50, pp. 38738-38747, (Dec. 2006).

Murn, J. et al., "Control of a neuronal morphology program by an RNA-binding zinc finger protein, Unkempt", Genes & Development 29, pp. 501-512, (2015).

Murray, R.Z., Jolly, L.A., Wood, S.A., "The FAM Deubiquitylating Enzyme Localizes to Multiple Points of Protein Trafficking in Epithelia, where It Associates with E-cadherin and ß-catenin", Molecular Biology of the Cell, vol. 15, pp. 1591-1599; (Apr. 2004).

Muzyamba, M. and Gibson, J., Effect of 1-chloro-2,4-dinitrobenzene on K+ transport in normal and sickle human red blood cells, Journal of Physiology, 547(3):903-911 (2003).

Nagai, H., et al., "Ubiquitine-like Sequence in ASK1 Plays Critical Roles in the Recognition and Stabilization by USP9X and Oxidative Stress-Induced Cell Death", Molecular Cell 36, pp. 805-818, (Dec. 2009).

Nagy, Peter I., et al., "Theoretical and Experimental Study on Ion-Pair Formation and Partitioning of Organic Salts in Octanol/Water and Dichloromethane/Water Sytems", Journal of the American Chemical Society, 122 (28), pp. 6583-6593 (2000).

Nam, Keun-Soo et al., "Synthesis of quinolone antimicrobial agents and their antibacterial activities," 5 Korean J. Med. Chem. (1995), pp. 2-5.

Narayanan, N., Wang, Z., Li, L., and Yang, Y., "Arginine methylation of USP9X promotes its interaction with TDRD3 and its anti-apoptotic activities in breast cancer cells", Cell Discovery 3, pp. 1-17, (2017).

Nathan, J.A., et al., "The Ubiquitin E3 Ligase MARCH7 is Differentially Regulated by the Deubiquitylating Enzymes USP7 and USP9X", Traffic, 9, pp. 1130-1145, (2008).

Neto, E.D. et al., "Shotgun sequencing of the human transcriptome with ORF expressed sequence tags", PNAS, vol. 97, No. 7, pp. 3491-3496, (Mar. 2000).

Noma, T., et al., "Stage- and sex-dependent expressions of Usp9x, an X-linked mouse ortholog of *Drosophila* Fat facets, during gonadal development and oogenesis in mice", Gene Expression Patters 2, pp. 87-91, (2002).

O'Connor, H.F., et al., "Ubiquitin-Activated Interaction Traps (UBAITs) identify E3 ligase binding partners", EMBO reports, vol. 16, No. 12., (2015).

Obach RS. "Prediction of human clearance of twenty-nine drugs from hepatic microsomal intrinsic clearance data: An examination of in vitro half-life approach and nonspecific binding to microsomes." Drug Metab Dispos. Nov. 1999, 27(11):1350-9.

Oksenberg D, Dufu K, Patel MP, Chuang C, Li Z, Xu Q, Silva-Garcia A, Zhou C, Hutchaleelaha A, Patskovska L, Patskovsky Y, Almo SC, Sinha U, Metcalf BW, Archer DR. "GBT440 increases haemoglobin oxygen affinity, reduces sickling and prolongs RBC half-life in a murine model of sickle cell disease." Br J Haematol. Oct. 2016, 175(1):141-53.

Oliviero, G., et al., "The variant Polycomb Repressor Complex 1 component PCGF1 interacts with a pluripotency sub-network that includes DPPA4, a regulator of embryogenesis", pp. 1-11, (2015).

Olsen, J.V., et al., "Global, In Vivo, and Site-Specific Phosphorylation Dynamics in Signaling Networks", Cell 127, pp. 635-648, (Nov. 2006).

Oski, M.D., Frank A., "The Role of Organic Phosphates in Erythrocytes on the Oxygen Dissociation of Hemoglobin," Annals of Clinical Laboratory Science, vol. 1, No. 2 (Nov. 1970), pp. 162-176.

Ould Amar, A.K. et al., Assessment of qualitative functional parameters of stored red blood cells from donors with sickle cell trait (AS) or with heterozygote (AC) status, Transfus Clin Biol., 3(4):225-233 (1996).

Ouyang, W., et al., "ß-catenin is regulated by USP9x and mediates resistance to TRAIL-induced apoptosis in breast cancer", Oncology Reports 35, pp. 717-724, (2016).

OXBRYTA [package insert]. San Francisco, California, Global Blood Therapeutics, Inc. (Nov. 2019), 15 pgs.

OXBRYTA Slide Show—Jan. 2020.

Paemka, L., et al., "Seizures Are Regulated by Ubiquitin-specific Peptidase 9 X- linked (USP9X), a De-Ubiquitinase", PLOS Genetics, 11(3): pp. 1-16, (Mar. 2015).

Palsson-Mcdermott, EM et al., Pyruvate kinase M2 regulates Hif-1a activity and IL-1ß induction and is a critical determinant of the Warburg Effect in LPS-activated macrophages, Cell Metabolism, 21:65-80 (2015).

Papp, S.J., et al., "DNA damage shifts circadian clock time via Hausp-dependent Cry1 stabilization", eLIFE, p.p. 1-19, (2015).

Park, Yoon, Jin, Hyung-seung, and Liu, Yun-Cai, "Regulation of T cell function by the ubiquitin-specific protease USP9X via modulating the Carma 1-Bcl10-Malt1 complex", PNAS, vol. 110, No. 23, pp. 9433-9438, (Jun. 2013).

Pászty C. "Transgenic and gene knock-out mouse models of sickle cell anemia and the thalassemias." Curr Opin Hematol. 1997, 4(2):88-93.

Patel, P., et al., Synthesis of some novel pyrazoline and cyanopyridine derivatives as antimicrobial agents, Il Farmaco, vol. 51, No. 1, (1996), Abstract only.

Pavagadhi, T.H., et al., 3-(3'-phenoxyphenylmethyl)-5-aryl-1-acetylpyrazolines, Journal of the Institution of Chemists (India), vol. 73, No. 3, (2001), Abstract only.

Peddaboina, C. et al., "The downregulation of Mcl-1 via USP9X inhibition sensitizes solid tumors to Bcl-xl inhibition", BMC Cancer, 12:541, pp. 1-12, (2012).

Perez-Mancera, P.A., et al., "The deubiquitinase USP9X suppresses pancreatic ductal adenocarcinoma", Nature, 486(7402): pp. 266-270; (Dec. 2012).

Platt OS. "Hydroxyurea for the treatment of sickle cell anemia." N Engl J Med. 2008;358(13):1362-9.

Poillon W., & Kim, B., 2,3-Diphosphoglycerate and intracellular pH as interdependent determinants of the physiologic solubility of deoxyhemoglobin S, Blood, 76:1028-1036 (1990).

Poillon, W. et al., Antisickling effects of 2,3-Diphosphoglycerate Depletion, Blood, 85(11):3289-3296 (1995).

Poillon, W. et al., Intracellular hemoglobin S polymerization and the clinical severity of sickle cell anemia, Blood, 91:1777-1783 (1998).

Poillon, W. et al., The Effect of 2,3-Diphosphoglycerate on the Solubility of Deoxyhemoglobin S1, Archives of Biochemistry and Biophysics, vol. 249, No. 2, pp. 301-305, (Sep. 1986).

Press Release—"Agios Announces New Data from AG-348 and AG-519 Demonstrating Potential for First Disease-modifying Treatment for Patients with PK Deficiency" Dec. 4, 2016—Globe Newswire.

Press Release—"Agios Presents Updated Data from Drive PK Study Demonstrating AG-348 is Well-Tolerated and Results in Clinically Relevant, Rapid and Sustained Hemoglobin Increases in Patients with Pyruvate Kinase Deficiency" Dec. 10, 2017—Globe Newswire.

PubChem SID: 440235168, modify date Feb. 25, 2021 (Feb. 25, 2021), Version 2, p. 1-7, Structure.

PubChem SID: 440235168, date Feb. 18, 2021 (Feb. 18, 2021), Version 1 of 2, p. 1-7, Structure.

PubChem CID: 135338361, create date: Dec. 15, 2018 (Dec. 15, 2018), p. 1, formula.

PubChem CID: 135338378, create date: Dec. 15, 2018 (Dec. 15, 2018), p. 1, formula.

PubChem CID: 69203074, create date: Nov. 30, 2012 (Nov. 30, 2012), pp. 1-20, compound summary.

(56) References Cited

OTHER PUBLICATIONS

PubChem CID: 69203505, create date: Nov. 30, 2012 (Nov. 30, 2012), pp. 1-20, compound summary.

Rab, et al., AG-348 (Mitapivat), an allosteric activator of red blood cell pyruvate kinase, increases enzymatic activity, protein stability, and ATP levels over a broad range of PKLR genotypes, Haematologica, 105:xxx, (Jan. 23, 2020).

Rab, M.A.E et al., Rapid and reproducible characterization of sickling during automated deoxygenation in sickle cell disease patients, Am. J. Hematol. (2019; 94; pp. 575-584.

Rabai M, Detterich JA, Wenby RB, et al. "Deformability analysis of sickle blood using ektacytometry." Biorheology. 2014;51(2-3):159-70.

Ramdani, G. and Langsley, G., ATP, an Extracellular Signaling Molecule in Red Blood Cells: A Messenger for Malaria?, Biomed Journal, 37(5):284-292 (2014).

Raththagala, M. et al., Hydroxyurea stimulates the release of ATP from rabbit erythrocytes through an increase in calcium and nitric oxide production, European Journal of Pharmacology, 645(1-3):32-38 (2010).

REBLOZYL [package insert]. Cambridge, Massachusetts, Acceleron Pharma, Inc. (2020), 27 pgs.

REBLOZYL [package insert]. Summit, New Jersey, Celgene Corporation (Nov. 2019), 16 pgs.

Rice-Evans C, Omorphos SC, Baysal E. "Cell membranes and oxidative damage." Biochem J. Jul. 1, 1986, 237(1):265-9.

Rosa, M. et al., Allosteric properties of hemoglobin and the plasma membrane of the erythrocyte: New insights in gas transport and metabolic modulation, Life, 60(2):87-93 (2008).

Ross, M.T., et al., "The DNA sequence of the human X chromosome", Nature, 434, pp. 325-337; (Mar. 2005).

Rott, Ruth, et al., "α-Synuclein fate is determined by USP9X-regulated monoubiquitination", PNAS, (2011).

Roy, R., et al., "hnRNPA1 couples nuclear export and translation of specific mRNAs downstream of FGF-2/S6K2 signalling", Nucleic Acids Research, vol. 42, No. 20, p. 12483-12497, (Oct. 2014).

Rush, J., et al., "Immunoaffinity profiling of tyrosine phosphorylation in cancer cells", Nature Biotechnology, vol. 23, No. 1, pp. 94-101, (2005).

Sampson M, Archibong AE, Powell A, et al. "Perturbation of the developmental potential of preimplantation mouse embryos by hydroxyurea." Int J Environ Res Public Health. 2010;7(5):2033-44.

Sato, Y., et al., "Ubiquitin-specific protease 9X in host cells interacts with herpes simplex virus 1 ICP0", J. Vet. Med. Sci. 78(3), pp. 405-410; (2016).

Savio et al., "USP9X Controls EGFR Fate by Deubiquitinating the Endocytic Adaptor Eps15", Current Biology 26, pp. 173-183, (Jan. 2016).

Schwartz, R. et al., Two distinct pathways mediate the formation of intermediate density cells and hyperdense cells from normal density sickle red blood cells, Blood, 92(12):4844-4855 (1998).

Schwickart, M., et al., "Deubiquitinase USP9X stabilizes MCL1 and promotes tumour cell survival", Nature vol. 463, pp. 103-108; (Jan. 2010).

Sega, M. et al., Fluorescence assay of the interaction between hemoglobin and the cytoplasmic domain of erythrocyte membrane band 3, Blood Cells Mol Dis., 55(3):266-271 (2015).

Shen, G., et al., "MicroRNA-26b inhibits epithelial-mesenchymal transition in hepatocellular carcinoma by targeting USP9X," BMC Cancer 14:393, pp. 1-11, (2014).

Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Blood (2020) 136 (Supplement 1):21-22, Nov. 4, 2020.

Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Presented at the 62$^{nd}$ American Society of Hematology (ASH) Annual Meeting, Dec. 5, 2020.

SIKLOS [package insert]. Lannoy, France, Delpharm Lille, (May 2019), 24 pgs.

SIKLOS [package insert]. Paris, France, Addmedica, (Dec. 2017), 25 pgs.

SIKLOS [package insert]. Paris, France, Addmedica, (May 2018), 23 pgs.

Smidrkal, Jan., "Synthesis of fagaronine", Collection of Czechoslovak Chemical Communications, 53(12), pp. 3184-3192, (1988).

Sorathiya, S.D., et al., Preparation and antimicrobial activity of 3-(p-(2',5'-dibromobenzenesulfonamido)phenyl)-5-aryl-1H/acetyl/phenyl-2-pyrazolines, Indian Journal of Chemistry, Section B: Organic, Incl. Medicinal Chemistry, vol. 36B, No. 7, (1997), Abstract only.

Soupene, E. and Kuypers, F., Identification of an erythroid ATP-dependent aminophospholipid transporter, British Journal of Haematology, 133(4): 436-438 (2006).

Space SL, Lane PA, Pickett CK, Weil JV. "Nitric oxide attenuates normal and sickle red blood cell adherence to pulmonary endothelium." Am J Hematol. Apr. 2000, 63(4):200-4.

Spinella, J.F., et al., "Genomic characterization of pediatric T-cell acute lymphoblastic leukemia reveals novel recurrent driver mutations", Oncotarget, vol. 7, No. 40, pp. 65485-65503, (Sep. 2016).

Stasiuk, M. et al., Transformations of erythrocytes shape and its regulation, Postepy Biochem., 55(4):425-33 (2009). English Abstract.

St-Denis, N., et al., "Phenotypic and Interaction Profiling of the Human Phosphatases Identifies Diverse Mitotic Regulators", Cell Reports 17, pp. 2488-2501, (Nov. 2016).

Stebbins et al., Crystal Structure of an Hsp90-Geldanamycin Complex: Targeting of a Protein Chaperone by an Antitumor Agent, Cell, (Apr. 1997), 89, p. 241.

Steinberg, Martin H., Pathophysiologically based drug treatment of sickle cell disease, TRENDS in Pharmacological Sciences, vol. 27, No. 4, (Apr. 2006).

Strausberg, R.L., et al., "Generation and initial analysis of more than 15,000 full-length human and mouse cDNA sequences", PNAS vol. 99, No. 26, p. 16899-16903, (Dec. 2002).

Sun, H., et al., "Bcr-Abl ubiquitination and Usp9x inhibition block kinase signaling and promote CML cell apoptosis", Blood, (Jan. 2011).

Sundd, Prithu et al., Pathophysiology of Sickle Cell Disease, Annual Review of Pathology: Mechanisms of Disease, (Oct. 9, 2018), pp. 261-290.

Swanson, Devin M et al., "Identification and biological evaluation of 4-(3-trifluoromethylpyridine-2-yl) piperazine-1-c arboxylic acid (5-trifluoromethylpyridin-2-yl) amide, a high affinity TRPV1 (VR1) vanilloid receptor antagonist", Journal of Medicinal Chemistry, 48(6), pp. 1857-1872 (2005).

Taipale, M., et al., "A Quantitative Chaperone Interaction Network Reveals the Architecture of Cellular Protein Homeostasis Pathways", Cell 158, pp. 434-448, (Jul. 2014).

Takenaka, M. et al., Isolation and characterization of the human pyruvate kinase M gene, Eur J Biochem, 198(1):101-106 (1991).

Talmud, P.J., et al., "Gene-centric Association Signals for Lipids and Apolipoproteins Identified via the Human CVD Bead Chip", The American Journal of Human Genetics 85, pp. 628-642, (Nov. 2009).

Tanphaichitr, V.S. et al., Successful bone marrow transplantation in a child with red blood cell pyruvate kinase deficiency, Bone Marrow Transplant, 26(6):689-690 (2000).

Taya, S., et al., "The deubiquitinating enzyme Fam interacts with and stabilizes ß-catenin", Genes to Cells 4, pp. 757-767, (1999).

Taya, S., et al., "The Ras Target AF-6 is a Substrate of the Fam Deubiquitinating Enzyme", The Journal of Cell Biology, vol. 142, No. 4, pp. 1053-1062, (Aug. 1998).

Telen, Marilyn, Malik, Punam, and Vercellotti, Gregory M., Therapeutic strategies for sickle cell disease: towards a multi-agent approach, Nature Reviews/Drug Discovery; (Dec. 4, 2018).

Terao, Y., et al., "Trifluoroacetic Acid-Catalyzed 1,3-Cycloaddition of the Simplest Iminium Ylide Leading to 3- or 3,4-Substituted Pyrrolidines and 2,5-Dihydropyrroles", Chem. Pharm. Bull., 33(7), pp. 2762-2766, (1985).

(56) References Cited

OTHER PUBLICATIONS

Theard, D., et al., "USP9x-mediated deubiquitination of EFA6 regulates de novo tight junction assembly", The EMBO Journal, vol. 29, No. 9, pp. 1499-1509, (2010).
Thein, Swee Lay, The Molecular Basis of ß-Thalassemia, Cold Spring Harb Perspect Med. (2013).
Thompson, Alexis, M.D., M.P.H., "A Targeted Agent for Sickle Cell Disease—Changing the Protein but Not the Gene," The New England Journal of Medicine, (Jun. 14, 2019).
Tian, S., et al., Yaoxue Xueba (1993), 28(11), pp. 870-875. Chemical Abstract No. 120:299229.
Toloczko, A., et al., "Deubiquitinating Enzyme USP9X Suppresses Tumor Growth via LATS kinase and Core Components of the Hippo pathway", Cancer Research, pp. 1-37, (Jul. 2017).
Tripathi, Ashutoshi and Safo, Martin K., In Silico-Screening Approaches for Lead Generation: Identification of Novel Allosteric Modulators of Human-Erythrocyte Pyruvate Kinase, Allostery: Methods and Protocols, Methods in Molecular Biology, Chpt. 19, vol. 796, pp. 351-367 (2012).
Trivigno, D., et al., "Deubiquitinase USP9x Confers Radioresistance through Stabilization of Mcl-1 1,2", NEO Plasia, vol. 14, No. 10, pp. 893-904, (Oct. 2012).
Tsai, Y.C., et al., "Functional Proteomics Establishes the Interaction of SIRT7 with Chromatin Remodeling Complexes and Expands Its Role in Regulation of RNA Polymerase I Transcription", Molecular & Cellular Proteomics 11.5, pp. 60-76, (2012).
Tsutsumi H, Tani K, Fujii H, Miwa S. "Expression of L- and M-type pyruvate kinase in human tissues. Genomics." 1988, 2(1):86-9.
United States Securities and Exchange Commission, Form S-1 Registration Statement, Forma Therapeutics Holdings, Inc., dated Dec. 8, 2020, 374 pages.
United States Securities and Exchange Commission, Form S-1, Registration Statement—Forma Therapeutics Holdings, Inc., May 29, 2020.
Upadhyay J., et al., Studies on pyrazolines. Part III. Preparation and antimicrobial activity of 3-(4-phenylsulfonamidophenyl) -5-aryl-1-ace tyl/phenyl -4,5-dihydropyrazoles, Journal of the Indian Chemical Society, vol. 68, No. 7, (1991), pp. 413-414.
Van Zweiten, R. et al., Inborn defects in the antioxidant systems of human red blood cells, Free Radio Biol Med., 67:377-386 (2014).
Vanderah et al., Novel d-amino acid tetrapeptides produce potent antinociception by selectively acting at peripheral kappa-opioid receptors, European Journal of Pharmacology, Elsevier Science, vol. 583, No. 1, pp. 62-72 (Jan. 24, 2008).
Varjosalo, M., et al., The Protein Interaction Landscape of the Human CMGC Kinase Group, Cell Reports 3, pp. 1306-1320, (Apr. 2013).
Verma, S.K. et al., Imidazole-Catalyzed Monoacylation of Symmetrical Diamines, Organic Letters, 12(19): 4232-4235 (201).
Vichinsky, E. et al., "A Phase 3 Randomized Trial of Voxelotor in Sickle Cell Disease," N Engl J Med. DOI: 10.1056/NEJMoa1903212 (Jun. 2019).
Vichinsky, E. et al., Protocol to A Phase 3 Randomized Trial of Voxelotor in Sickle Cell Disease, (Jun. 14, 2019).
Vichinsky, E. et al., Supplementary Appendix to A Phase 3 Randomized Trial of Voxelotor in Sickle Cell Disease, (Jun. 14, 2019).
Vong, Q. P., et al., "Chromosome Alignment and Segregation Regulated by Ubiquitination of Survivin", Science, vol. 310, pp. 1499-1504, (Dec. 2, 2005).
Voskou S, Aslan M, Fanis P, Phylactides M, Kleanthous M. "Oxidative stress in ß-thalassaemia and sickle cell disease." Redox Biol. Dec. 2015, 6:226-39.
Wagner, G et al., Red cell vesiculation—a common membrane physiologic event, J Lab Clin., 108(4):315-324 (1986).
Wan, C., et al., "Panorama of ancient metazoan macromolecular complexes", Nature 525(7569), pp. 339-344, (Sep. 2015).
Wang, G.S., et al., Journal of Ethnopharmacology, 26 (1989), pp. 147-162.

Wang, H. et al., JMJD5 regulates PKM2 nuclear translocation and reprograms HIF-1a- mediated glucose metabolism, PNAS, 111(1):279-284 (2014).
Wang, J., et al., "TopBP1 Controls BLM Protein Level to Maintain Genome Stability", Molecular Cell 52, pp. 667-678, (Dec. 2013).
Wang, Q., et al., "The X-linked Deubiquitinase USP9X Is an Integral Component of Centrosome", The American Society for Biochemistry and Molecular Biology, Inc., pp. 1-33, (2017).
Wang, S. et al., "Ablation of the oncogenic transcription factor ERG by deubiquitinase inhibition in prostate cancer", PNAS, vol. 111, No. 11, pp. 4251-4256, (Mar. 2014).
Wang, S., et al., "The ubiquitin ligase TRIM25 targets ERG for degradation in prostate cancer", Oncotarget, vol. 7, No. 40, p. 64921-64931, (2016).
Wang, X, et al., "Hsp90 Cochaperone Aha1 Downregulation Rescues Misfolding of CFTR in Cystic Fibrosis", Cell 127, pp. 803-815, (Nov. 2006).
Waza et al., Nature, 11, No. 10, (Oct. 2005), pp. 1088-1095.
Weatherall, D., The inherited diseases of hemoglobin are an emerging global health burden, Blood, 115(22):4331-43336 (2010).
Wei, Wan-Guo et al., "A practical procedure for multisubstituted .beta.-naphthols and their derivatives", Tetrahedron, 59(34), pp. 6621-6625, (2003).
Willcocks, J. et al., Simultaneous determination of low free Mg2+ and pH in human sickle cells using P NMR spectroscopy, The Journal of Biological Chemistry, 277(51):49911-49920 (2002).
Wood BL, Gibson DF, Tait JF. "Increased erythrocyte phosphatidylserine exposure in sickle cell disease: flow-cytometric measurement and clinical associations." Blood., 88(5):1873-80 (Sep. 1, 1996).
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease (PRAISE)," Blood (2020) 136 (Supplement 1):19-20, Nov. 4, 2020.
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease," Presented at the 62nd American Society of Hematology (ASH) Annual Meeting, Dec. 7, 2020.
Woods, N.T., et al., "Charting the Landscape of Tandem BRCT Domain-Mediated Protein Interactions", Sci Signal, 5(242), pp. 1-35, (2014).
Wright, S.W. et al., A Convenient Preparation of Heteroaryl Sulfonamides and Sulfonyl Fluorides from Heteroaryl Thiols, J. Org. Chem., 71: 1080-1084 (2006).
Wu, Y., et al., "Aberrant phosphorylation of SMAD4 Thr277-mediated USP9x-SMAD4 interaction by free fatty acids promotes breast cancer matastasis", Cancer Research, pp. 1-34, (2017).
Wu, Z., et al., "Targeted Ubiquitination and Degradation of G-Protein-Coupled Receptor Kinase 5 by the DDB1-CUL4 Ubiquitin Ligase Complex", PLOS One, vol. 7, Issue 8, pp. 1-11, (Aug. 2012).
Xie, Y., et al., "Deubiquitinase FAM/USP9X Interacts with the E3 Ubiquitin Ligase SMURF1 Protein and Protects It from Ligase Activity-dependent Self-degradation", The Journal of Biological Chemistry., vol. 288, No. 5, pp. 2976-2985, (Feb. 2013).
Xu, Z., et al., "Identification of a Deubiquitinating Enzyme as a Novel AGS3-Interacting Protein", PLOS One, vol. 5, Issue 3, pp. 1-12, (Mar. 2010).
Yan, J., et al., "Usp9x- and Noxa-mediated Mcl-1 downregulation contributes to pemetrexed-induced apoptosis in human non-small-cell lung cancer cells", Cell Death and Disease 5, pp. 1-7, (2014).
Yang H, Merica E, Chen Y, Cohen M, Goldwater R, Hill C, et al. "Phase I single (SAD) and multiple ascending dose (MAD) studies of the safety, tolerability, pharmacokinetics (PK) and pharmacodynamics (PD) of AG-348, a first-in-class allosteric activator of pyruvate kinase-R, in healthy subjects." Blood. 2014, 124:4007.
Yang H, Merica E, Chen Y, et al. "Phase 1 Single- and Multiple-Ascending-Dose Randomized Studies of the Safety, Pharmacokinetics, and Pharmacodynamics of AG-348, A First-in-Class Allosteric Activator of Pyruvate Kinase R, in Healthy Volunteers." Clin Pharmacol Drug Dev. Aug. 9, 2018.
Yang, H. et al., Phase 1 Single- and Multiple-Ascending-Dose Randomized Studies of the Safety, Pharmacokinetics, and

(56) References Cited

OTHER PUBLICATIONS

Pharmacodynamics of AG-348, a First-in-Class Allosteric Activator of Pyruvate Kinase R, in Healthy Volunteers, 8 Clin. Pharmacol. Drug Dev. 246-259 (2019).

Yi, S., et al., Leukemia Research, vol. 15(10), (1991), pp. 883-886.

You, J. and Pickart, C.M., "A HECT Domain E3 Enzyme Assembles Novel Polyubiquitin Chains", vol. 276, No. 23, p. 19871-19878, (2001).

Yu, W., et al., "Large-Scale Concatenation cDNA Sequencing", Genome Research 7, pp. 353-358, (1997).

Zanella A, Fermo E, Bianchi P, Chiarelli LR, Valentini G. "Pyruvate kinase deficiency: The genotype-phenotype association." Blood Rev. 2007, 23:217-31.

Zanella A, Fermo E, Bianchi P, Valentini G. "Red cell pyruvate kinase deficiency: molecular and clinical aspects." Br J Haematol. 2005;130(1):11-25.

Zhang, C., et al., "Synergistic anti-tumor activity of gemcitabine and ABT-737 in vitro and in vivo through disrupting the interaction of USP9X and Mcl-1", Molecular Cancer Therapeutics, (May 12, 2011).

Zhang, C., et al., "USP9X destabilizes pVHL and promotes cell proliferation", Oncotarget, vol. 7, No. 37, pp. 60519-60534, (2016).

Zhang, Y & Xia, Y., Adenosine signaling in normal and sickle erythrocytes and beyond, Microbes Infect., 14(10) (2012).

Zhang, Y. et al., Detrimental effects of adenosine signaling in sickle cell disease, Nature Medicine, 17(1):79-87 (2011).

Zhang, Yongmin et al., "Organic reactions in chiral micelles. 7. The structural effects on the asymmetric oxidation of prochiral sulfides in chiral micelles", Chinese Journal of Chemistry, (1990), pp. 89-96.

Zhao, Y., et al., "Noncanonical regulation of alkylation damage resistance by the OTUD4 deubiquitinase", EMBO Journal, vol. 34, No. 12, pp. 1687-1703, (2015).

Zhi et al., Hybrid Antibacterals. DNA Polymerase—Topoisomerase Inhibitors. J. Med. Chem., published on Web Jan. 25, 2006., vol. 49, pp. 1455-1465, especially p. 1456. Scheme 3, compound 4; p. 1457, Scheme 4, compound 13, p. 1462.

Zhou, L., et al., "The Scaffold Protein KSR1, A Novel Therapeutic Target for the Treatment of Merlin-Deficient Tumors", Oncogene 35(26), pp. 3443-3453, (Jun. 2016).

Zhou, ZH et al., Phosphorus, Sulfur and Silicon and the Related Elements (1999), 152, pp. 45-52. Chemical Abstract No. 132: 180853.

Zhu, Tong et al., Polymer-Supported Synthesis of Pyridone-Focused Libraries as Inhibitors of Anaplastic Lymphoma Kinase, Journal of Combinatorial Chemistry, 8(3), pp. 401-409.

National Center for Biotechnology Information. PubChem Substance Record for SID 377251214, SCHEMBL20511283 Source: SureChEMBL. https://pubchem.ncbi.nim.nih.gov/substance/377251214. Accessed Nov. 3, 2020. Available Dec. 15, 2018.

U.S. Appl. No. 16/576,720, filed Sep. 19, 2019, 47 pages.

Qian et al., "Drug-polymer solubility and miscibility: Stability consideration and practical challenges in amorphous solid dispersion development", J. Pharm. Sci., Jul. 2010, vol. 99, No. 7, pp. 2941-2947.

SureChEMBL, "Open Patent Data", 2 pages, downloaded Oct. 31, 2023 from https://www.surechembl.org/knowledgebase/75969.

Schroeder et al., "Etavopivat, a Pyruvate Kinase Activator in Red Blood Cells, for the Treatment of Sickle Cell Disease", The Journal of Pharmacology and Experimental Therapeutics, Mar. 2022, vol. 380, pp. 210-219.

FIGURE 1

| Cpd. No. | Structure and Name | LCMS | ¹H NMR | AC₅₀ (G332S) | AC₅₀ (R510Q) | AC₅₀ (WT) |
|---|---|---|---|---|---|---|
| 3a | 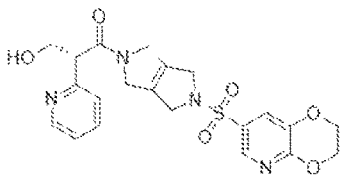 (R)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-(pyridin-2-yl)propan-1-one | m/z: 459.0 | (400 MHz, DSMO-$d_6$): δ 8.45-8.43 (m, 1H), 8.14 (d, J = 2.4 Hz, 1H), 7.74-7.62 (m,1H), 7.61 (d, J = 2.4 Hz, 1H), 7.30-7.22 (m, 2H), 4.80 (t, J = 5.2 Hz, 1H), 4.50-4.48 (m, 2H), 4.40-4.37 (m, 1H), 4.32-4.30 (m, 2H), 4.05-3.91 (m, 9H), 3.70-3.65 (m, 1H). | + | ++ | +++ |
| 4a | 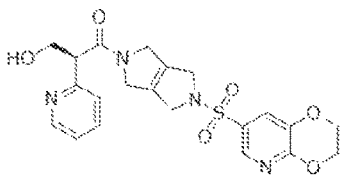 (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-(pyridin-2-yl)propan-1-one | m/z: 459.0 | (400 MHz, DSMO-$d_6$): δ 8.45-8.43 (m, 1H), 8.14 (d, J = 2.4 Hz, 1H), 7.74-7.62 (m,1H), 7.62 (d,J = 2.4 Hz, 1H), 7.30-7.22 (m, 2H), 4.80 (t, J = 5.20 Hz, 1H), 4.50-4.48 (m, 2H), 4.40-4.37 (m, 1H), 4.32-4.30 (m, 2H), 4.05-3.91 (m, 9H), 3.70-3.65 (m, 1H). |  | + | + |

FIGURE 1
(continued 1 of 20)

| Cpd. No. | Structure and Name | LCMS | 1H NMR | AC50 (G332S) | AC50 (R510Q) | AC50 (WT) |
|---|---|---|---|---|---|---|
| 5b | 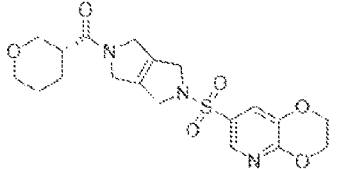 (R)-(5-((2,3-dihydro-[1,4]dioxino[2,3-b]pyridin-7-yl)sulfonyl)-3,4,5,6-tetrahydropyrrolo[3,4-c]pyrrol-2(1H)-yl)(tetrahydro-2H-pyran-3-yl)methanone | m/z: 422 | (400 MHz, CDCl$_3$): δ 8.31 (s, 1H), 7.60 (s, 1H), 4.57-4.50 (m, 2H), 4.36-4.25 (m, 4H), 4.15-4.09 (m, 6H), 3.94-3.88 (m, 2H), 3.56-3.50 (m, 1H), 3.49-3.33 (m, 1H), 2.63-2.60 (m, 1H), 1.95-1.78 (m, 2H), 1.67-1.61 (m, 2H). | + | + | ++ |
| 6b | 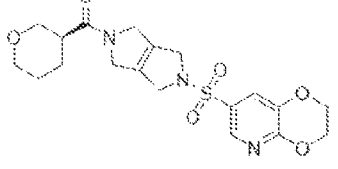 (S)-(5-((2,3-dihydro-[1,4] dioxino[2,3-b]pyridin-7-yl)sulfonyl)-3,4,5,6-tetrahydropyrrolo[3,4-c] pyrrol-2(1H)-yl)(tetrahydro-2H-pyran-3-yl)methanone | m/z: 422 | (400 MHz, CDCl$_3$): δ 8.30 (s, 1H), 7.61 (s, 1H), 4.54-4.52 (m, 2H), 4.35-4.27 (m, 4H), 4.15-4.09 (m, 6H), 3.95-3.90 (m, 2H), 3.56-3.50 (m, 1H), 3.42-3.35 (m, 1H), 2.65-2.60 (m, 1H), 1.95-1.78 (m, 2H), 1.67-1.62 (m, 2H). | 0 | 0 | + |
| 7 | 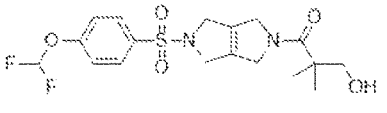 1-(5-((4-(difluoromethoxy)phenyl)sulfonyl)-3,4,5,6-tetrahydropyrrolo[3,4-c]pyrrol-2(1H)-yl)-3-hydroxy-2,2-dimethylpropan-1-one | m/z: 417 | (300 MHz, DMSO-d$_6$): δ ppm 7.89-7.92 (m, 2H), 7.39-7.42 (d, J = 7.8 Hz, 2H), 7.17-7.66 (t, J = 73.2 Hz, 1H), 4.68-4.72 (t, J = 5.4 Hz, 1H), 3.90-4.50 (m, 8H), 3.40-3.42 (d, J = 5.4 Hz, 2H), 1.09 (s, 6H). | +++ | ++ | ++ |

(continued 2 of 20)

| Cpd. No. | Structure and Name | LCMS | 1H NMR | AC50 (G332S) | AC50 (R510Q) | AC50 (WT) |
|---|---|---|---|---|---|---|
| 8 |  1-(5-(benzofuran-5-ylsulfonyl)-3,4,5,6-tetrahydropyrrolo[3,4-c]pyrrol-2(1H)-yl)-3-hydroxy-2-phenylpropan-1-one | m/z: 439 | | | | +++ |
| 9 |  1-(5-(benzofuran-5-ylsulfonyl)-3,4,5,6-tetrahydropyrrolo[3,4-c]pyrrol-2(1H)-yl)-3-hydroxy-2,2-dimethylpropan-1-one | m/z: 391 | | | | +++ |
| 10 |  1-(5-(benzofuran-5-ylsulfonyl)-3,4,5,6-tetrahydropyrrolo[3,4-c]pyrrol-2(1H)-yl)-3-hydroxy-2-(hydroxymethyl)-2-methylpropan-1-one | m/z: 407 | | | | +++ |

(continued 3 of 20)

| Cpd. No. | Structure and Name | LCMS | ¹H NMR | AC$_{50}$ (G332S) | AC$_{50}$ (R510Q) | AC$_{50}$ (WT) |
|---|---|---|---|---|---|---|
| 11 |  1-(5-(benzofuran-5-ylsulfonyl)-3,4,5,6-tetrahydropyrrolo[3,4-c]pyrrol-2(1H)-yl)-2,2-bis(hydroxymethyl)butan-1-one | m/z: 421 | | | | ++ |
| 12 |  (R)-(5-(benzofuran-5-ylsulfonyl)-3,4,5,6-tetrahydropyrrolo[3,4-c]pyrrol-2(1H)-yl)(tetrahydrofuran-3-yl)methanone | m/z: 389.1 | | | | ++ |
| 13 |  (S)-(5-(benzofuran-5-ylsulfonyl)-3,4,5,6-tetrahydropyrrolo[3,4-c]pyrrol-2(1H)-yl)(tetrahydrofuran-3-yl)methanone | m/z: 389.1 | | | | ++ |

FIGURE 1
((continued 4 of 20))

| Cpd. No. | Structure and Name | LCMS | 1H NMR | AC50 (G332S) | AC50 (R510Q) | AC50 (WT) |
|---|---|---|---|---|---|---|
| 14 | 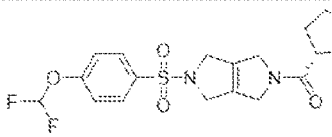 (R)-(5-((4-(difluromethoxy)phenyl)sulfonyl)-3,4,5,6-tetrahydropyrrolo[3,4-c]pyrrol-2(1H)-yl)(tetrahydrofuran-3-yl)methanone | m/z: 415 | (300 MHz, DMSO-$d6$): δ ppm 7.89-7.94 (m, 2H), 7.40- 7.42 (d, 2H), 7.18-7.66 (t, $J$ = 72 Hz, 1H) 3.83-4.29 (m, 9H), 3.62-3.74 (m, 3H), 3.06-3.16 (m, 1H), 1.94-2.07 (m, 2H). | ++ | + | ++ |
| 15 | 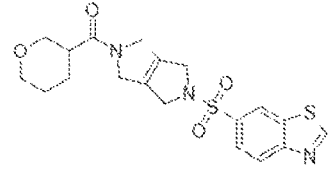 (5-(benzo[d]thiazol-6-ylsulfonyl)-3,4,5,6-tetrahydropyrrolo[3,4-c]pyrrol-2(1H)-yl)(tetrahydro-2H-pyran-3-yl)methanone | m/z: 420 | (300MHz, CDCl$_3$): δ ppm 9.22 (s, 1H), 8.54 (d, $J$ = 1.2 Hz, 1H), 8.29 (d, $J$ = 8.7 Hz, 1 H), 7.97 (dd, $J$ = 8.7 Hz, $J$ = 1.8 Hz, 1H), 4.24-4.12 (m, 8H), 3.94-3.90 (m, 2H), 3.54-3.41 (m, 2H), 2.65-2.55 (m, 1H), 1.86-1.81 (m, 2H), 1.67-1.49 (m, 2H). | 0 | + | ++ |
| 16 | 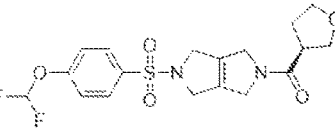 (S)-(5-((4-(difluromethoxy)phenyl)sulfonyl)-3,4,5,6-tetrahydropyrrolo[3,4-c]pyrrol-2(1H)-yl)(tetrahydrofuran-3-yl)methanone | m/z: 415 | (300 MHz, DMSO-$d6$): δ ppm 7.95-7.98 (m, 2H), 7.35- 7.42 (m, 2H), 6.79-7.28 (t, $J$ = 72 Hz, 1H) 3.80-4.32 (m, 14H), 3.24-3.40 (m, 1H), 2.22 (m, 2H). | ++ | + | ++ |

FIGURE 1
(continued 5 of 20)

| Cpd. No. | Structure and Name | LCMS | ¹H NMR | AC$_{50}$ (G332S) | AC$_{50}$ (R510Q) | AC$_{50}$ (WT) |
|---|---|---|---|---|---|---|
| 17 | 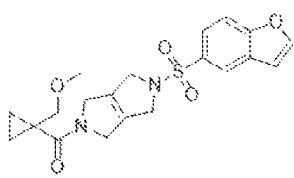 (5-(benzofuran-5-ylsulfonyl)-3,4,5,6-tetrahydropyrrolo[3,4-c]pyrrol-2(1H)-yl)(1-(methoxymethyl)cycloprotpyl)methanone | m/z: 403 | | | | ++ |
| 18 | 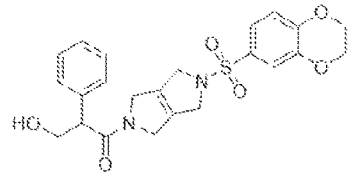 1-(5-((2,3-dihydrobenzo[b][1,4]dioxin-6-yl)sulfonyl)-3,4,5,6-tetrahydropyrrolo[3,4-c]pyrrol-2(1H)-yl)-3-hydroxy-2-phenylpropan-1-one | m/z: 457 | | 0 | +++ | |
| 19 | 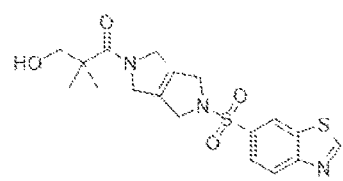 1-(5-(benzo[d]thiazol-6-ylsulfonyl)-3,4,5,6-tetrahydropyrrolo[3,4-c]pyrrol-2(1H)-yl)-3-hydroxy-2,2-dimethylpropan-1-one | m/z: 408 | | 0 | ++ | ++ |

(continued 6 of 20)

| Cpd. No. | Structure and Name | LCMS | ¹H NMR | AC$_{50}$ (G332S) | AC$_{50}$ (R510Q) | AC$_{50}$ (WT) |
|---|---|---|---|---|---|---|
| 20 |  (R)-(5-(benzo[d]thiazol-6-ylsulfonyl)-3,4,5,6-tetrahydropyrrolo[3,4-c]pyrrol-2(1H)-yl)(tetrahydrofuran-3-yl)methanone | m/z: 406 | | ++ | + | ++ |
| 21 |  3-hydroxy-2,2-dimethyl-1-(5-((2-methylbenzo[d]oxazol-6-yl)sulfonyl)-3,4,5,6-tetrahydropyrrolo[3,4-c]pyrrol-2(1H)-yl)propan-1-one | m/z: 406 | | | | + |
| 22 |  1-(5-(benzofuran-5-ylsulfonyl)-3,4,5,6-tetrahydropyrrolo[3,4-c]pyrrol-2(1H)-yl)-3-hydroxypropan-1-one | m/z: 363 | | | | ++ |

(continued 7 of 20)

| Cpd. No. | Structure and Name | LCMS | ¹H NMR | AC₅₀ (G332S) | AC₅₀ (R510Q) | AC₅₀ (WT) |
|---|---|---|---|---|---|---|
| 23 | <br>(R)-1-(5-(benzofuran-5-ylsulfonyl)-3,4,5,6-tetrahydropyrrolo[3,4-c]pyrrol-2(1H)-yl)-3-hydroxybutan-1-one | m/z: 377 | | | | ++ |
| 24 | <br>(S)-1-(5-(benzofuran-5-ylsulfonyl)-3,4,5,6-tetrahydropyrrolo[3,4-c]pyrrol-2(1H)-yl)-3-hydroxybutan-1-one | m/z: 377 | | | | ++ |
| 25 | <br>1-(5-(benzofuran-5-ylsulfonyl)-3,4,5,6-tetrahydropyrrolo[3,4-c]pyrrol-2(1H)-yl)-3-hydroxy-3-methylbutan-1-one | m/z: 391.14 | | | | ++ |

FIGURE 1
(continued 8 of 20)

| Cpd. No. | Structure and Name | LCMS | 1H NMR | AC50 (G332S) | AC50 (R510Q) | AC50 (WT) |
|---|---|---|---|---|---|---|
| 26 | 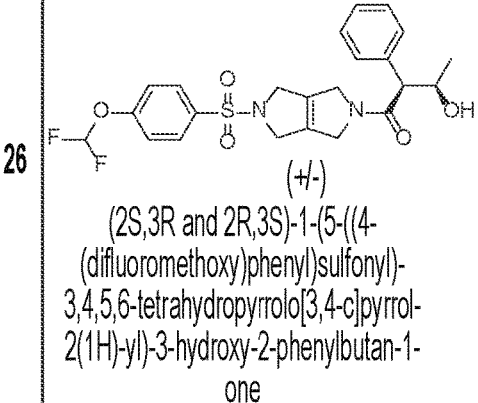<br>(+/-)<br>(2S,3R and 2R,3S)-1-(5-((4-(difluoromethoxy)phenyl)sulfonyl)-3,4,5,6-tetrahydropyrrolo[3,4-c]pyrrol-2(1H)-yl)-3-hydroxy-2-phenylbutan-1-one | m/z: 479.0 | (300MHz, CDCl$_3$): δ ppm 7.85-7.80 (m, 2H), 7.37-7.23 (m, 7H), 6.59 (t, J = 72.6 Hz, 1 H), 4.45-4.37 (m, 1H), 4.25-3.95 (m, 7H), 3.78-3.74 (m, 1H), 3.39 (d, J = 3.9 Hz, 1H), 1.05 (d, J = 6.3 Hz, 3 H). | +++ | +++ | +++ |
| 27 | 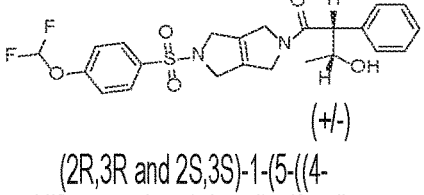<br>(+/-)<br>(2R,3R and 2S,3S)-1-(5-((4-(difluoromethoxy)phenyl)sulfonyl)-3,4,5,6-tetrahydropyrrolo[3,4-c]pyrrol-2(1H)-yl)-3-hydroxy-2-phenylbutan-1-one | m/z: 479 | (300MHz, CDCl$_3$): δ ppm 7.84-7.81 (m, 2H), 7.35-7.26 (m, 7H), 6.59 (t, J = 72.6 Hz, 1 H), 4.35-3.97 (m, 8H), 3.76-3.71 (m, 1H), 3.36-3.34 (m, 1H), 1.06 (dd, J = 13.2 Hz, J = 6.3 Hz, 3 H) | +++ | ++ | +++ |
| 28 | 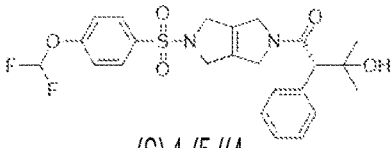<br>(S)-1-(5-((4-(difluoromethoxy)phenyl)sulfonyl)-3,4,5,6-tetrahydropyrrolo[3,4-c]pyrrol-2(1H)-yl)-3-hydroxy-3-methyl-2-phenylbutan-1-one | m/z: 493 | (300MHz, CDCl$_3$): δ ppm 7.83 (d, J = 8.7 Hz, 2H), 7.36-7.23 (m, 7H), 6.59 (t, J = 72.6 Hz, 1H), 4.28-3.85 (m, 8H), 3.32 (s, 1H), 1.39 (s, 3H), 0.92 (s, 3H) | +++ | + | ++ |

FIGURE 1
(continued 9 of 20)

| Cpd. No. | Structure and Name | LCMS | 1H NMR | AC50 (G332S) | AC50 (R510Q) | AC50 (WT) |
|---|---|---|---|---|---|---|
| 29 | 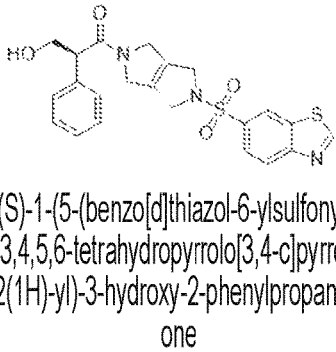 (S)-1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one | m/z: 456 | (300MHz, CDCl3): δ ppm 9.20 (s, 1H), 8.49 (s, 1H), 8.25 (d, J = 6.6 Hz, 1H), 7.94 (d, J = 8.7 Hz, 1H), 7.31-7.20 (m, 5H), 4.26- 4.03 (m, 8H), 3.73-3.64 (m, 3H) | +++ | +++ | +++ |
| 30 | 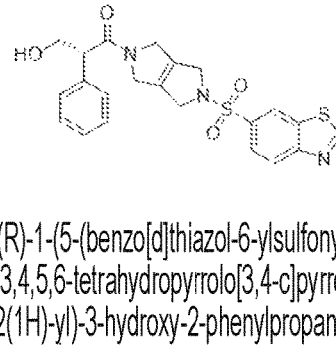 (R)-1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one | m/z: 456 | (300MHz, CDCl3): δ ppm 9.22 (s, 1H), 8.49 (s, 1H), 8.26 (d, J = 8.4 Hz, 1H), 7.94 (dd, J = 8.4 Hz, J = 1.8 Hz, 1H), 7.34-7.20 (m, 5H), 4.30-4.03 (m, 8H), 3.75-3.69 (m, 3H) | ++ | ++ | ++ |
| 31 | 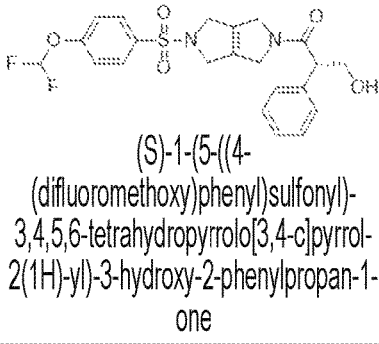 (S)-1-(5-((4-(difluoromethoxy)phenyl)sulfonyl)-3,4,5,6-tetrahydropyrrolo[3,4-c]pyrrol-2(1H)-yl)-3-hydroxy-2-phenylpropan-1-one | m/z: 465 | (300 MHz, DMSO-d6): δ ppm 7.89-7.85 (m, 2H), 7.64-7.15 (m, 8H), 4.76 (t, J = 5.1 Hz,1H), 4.40-4.36 (m, 1H), 4.04-3.82 (m, 8H), 3.80-3.77 (m, 1H), 3.48-3.41 (m, 1H) | +++ | +++ | +++ |

FIGURE 1
(continued 10 of 20)

| Cpd. No. | Structure and Name | LCMS | 1H NMR | AC50 (G332S) | AC50 (R510Q) | AC50 (WT) |
|---|---|---|---|---|---|---|
| 32 | 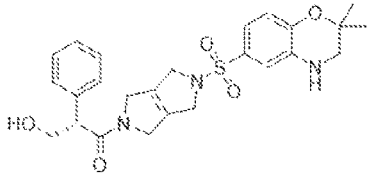<br>(S)-1-(5-((2,2-dimenthyl-3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2-phenylpropan-1-one | m/z: 484.0 | (300MHz, DMSO-$d_6$): δ ppm 7.29-7.28 (m, 5H), 7.04 (s, 1H), 6.90-6.85 (m, 1H), 6.76 (d, $J$ = 8.4 Hz, 1H), 6.35 (s, 1H), 4.85-4.70 (m, 1H), 4.50-4.30 (m, 1H), 3.97-3.93 (m, 8H), 3.90-3.80 (m, 1H), 3.35-3.50 (m, 1H), 3.02 (d, $J$ = 2.1 Hz, 2H), 1.24 (s, 6H). | 0 | +++ | +++ |
| 33c | 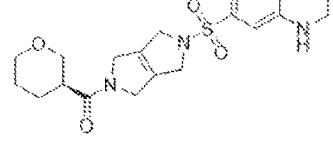<br>(S)-(5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydro-2H-pyran-3-yl)methanone | m/z: 420 | (300 MHz, CDCl$_3$): δ ppm 7.24-7.19 (m, 2H), 6.89 (d, $J$ = 6.6 Hz, 1H), 4.44-4.34 (d, 2H), 4.25-4.18 (m, 2H), 4.12 (s, 6H), 3.95-3.91 (m, 2H), 3.56-3.37 (m, 4H), 2.66-2.62 (m, 1H), 1.89-1.68 (m, 4H). | 0 | + | + |

(continued 11 of 20)

| Cpd. No. | Structure and Name | LCMS | 1H NMR | AC50 (G332S) | AC50 (R510Q) | AC50 (WT) |
|---|---|---|---|---|---|---|
| 34c | <br>(R)-(5-((3,4-dihydro-2H-benzo[b][1,4]oxazin-6-yl)sulfonyl)-3,4,5,6-tetrahydropyrrolo[3,4-c]pyrrol-2(1H)-yl)-(tetrahydro-2H-pyran-3-yl)methanone | m/z: 420 | (300 MHz, CDCl3): δ ppm 7.17-7.11 (m, 2H), 6.88 (d, J = 8.1 Hz, 1H), 4.33-4.25 (m, 4H), 4.12 (s, 6H), 3.95-3.91 (m, 2H), 3.56-3.37 (m, 4H), 2.67-2.57 (m, 1H), 1.89-1.66 (m, 4H). | ++ | +++ | +++ |
| 35 | <br>(S)-1-(5-((3,4-dihydro-2H-benzo[b][1,4]oxazin-6-yl)sulfonyl)-3,4,5,6-tetrahydropyrrolo[3,4-c]pyrrol-2(1H)yl-3-hydroxy-2-phenylpropan-1-one | m/z: 456 | | +++ | +++ | +++ |

(continued 12 of 20)

| Cpd. No. | Structure and Name | LCMS | 1H NMR | AC50 (G332S) | AC50 (R510Q) | AC50 (WT) |
|---|---|---|---|---|---|---|
| 36 |  (5-((3,4-dihydro-2H-benzo[b][1,4]oxazin-6-yl)sulfonyl)-3,4,5,6-tetrahydropyrrolo[3,4-c]pyrrol-2(1H)-yl)(1-(methoxymethyl)cyclopropyl)methanone | m/z: 420 | | 0 | + | ++ |
| 37 |  1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-2,2-dimenthylpropan-1-one | m/z: 408 | | 0 | +++ | ++ |

(continued 13 of 20)

| Cpd. No. | Structure and Name | LCMS | ¹H NMR | AC$_{50}$ (G332S) | AC$_{50}$ (R510Q) | AC$_{50}$ (WT) |
|---|---|---|---|---|---|---|
| 38 |  1-(5-((3,4-dihydro-2H-benzo[b][1,4]oxazin-6-yl)sulfonyl)-3,4,5,6-tetrahydropyrrolo[3,4-c]pyrrol-2(1H)-yl)-3-hydroxy-3-methylbutan-1-one | m/z: 408 | | | | |
| 39 |  (5-((3,4-dihydro-2H-benzo[b][1,4]oxazin-6-yl)sulfonyl)-3,4,5,6-tetrahydropyrrolo[3,4-c]pyrrol-2(1H)-yl)(tetrahydrofuran-3-yl)methanone | m/z: 406 | | +++ | ++ | ++ |
| 40 |  3-hydroxy-1-(5-((4-methoxyphenyl)sulfonyl)-3,4,5,6-tetrahydropyrrolo[3,4-c]pyrrol-2(1H)-yl)propan-1-one | | | | + | |

FIGURE 1
(continued 14 of 20)

| Cpd. No. | Structure and Name | LCMS | ¹H NMR | AC$_{50}$ (G332S) | AC$_{50}$ (R510Q) | AC$_{50}$ (WT) |
|---|---|---|---|---|---|---|
| 41d | 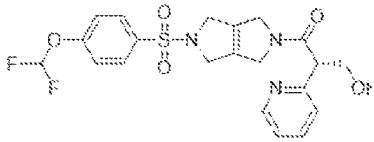 (S)-1-(5-((4-(difluoromethoxy)phenyl)sulfonyl)-3,4,5,6-tetrahydropyrrolo[3,4-c]pyrrol-2(1H)-yl)-3-hydroxy-2-(pyridin-2-yl)propan-1-one | m/z: 466 | (300 MHz, DMSO-$d_6$): δ ppm 8.45-8.47 (m, 1H), 7.90-7.87 (m, 2H), 7.70-7.75 (m, 1H), 7.37 (t, J = 73.2 Hz, 1H), 7.23-7.37 (m, 4H), 4.70-4.85 (m, 1H), 4.37-4.42 (m, 1H), 4.03-4.06 (m, 9H), 3.70-3.72 (m, 1H). | +++ | +++ | +++ |
| 42d | 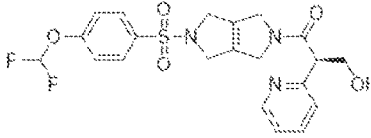 (R)-1-(5-((4-(difluoromethoxy)phenyl)sulfonyl)-3,4,5,6-tetrahydropyrrolo[3,4-c]pyrrol-2(1H)-yl)-3-hydroxy-2-(pyridin-2-yl)propan-1-one | m/z: 466 | (300 MHz, DMSO-$d_6$): δ ppm 8.45-8.47 (m, 1H), 7.90-7.87 (m, 2H), 7.70-7.75 (m, 1H), 7.31 (t, J = 73.2 Hz, 1H), 7.23-7.31 (m, 4H), 4.70-4.85 (m, 1H), 4.38-4.42 (m, 1H), 4.03-4.06 (m, 9H), 3.69-3.72 (m, 1H). | +++ | +++ | +++ |
| 43 | 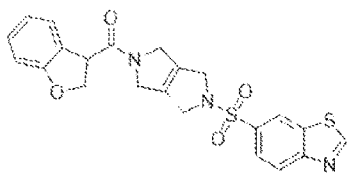 (5-(benzo[d]thiazol-6-ylsulfonyl)-3,4,5,6-tetrahydropyrrolo[3,4-c]pyrrol-2(1H)-yl)(2,3-dihydrobenzofuran-3-yl)methanone | m/z: 454 | (300 MHz, DMSO-$d_6$): δ ppm 9.66 (s,1H), 8.84 (d, J = 1.5 Hz, 1H), 8.32 (d, J = 8.4 Hz, 1H), 7.99 (dd, J1 = 8.7 Hz, J2 = 1.8 Hz, 1H), 7.14-7.09 (m, 2H), 6.80-6.75 (m, 2H), 4.67-4.38 (m, 5H), 4.18 (s, 4H), 4.01 (m, 2H). | ++ | + | ++ |

(continued 15 of 20)

| Cpd. No. | Structure and Name | LCMS | 1H NMR | AC50 (G332S) | AC50 (R510Q) | AC50 (WT) |
|---|---|---|---|---|---|---|
| 44e | <br>(R)-(5-(pyridin-2-ylsulfonyl)-3,4,5,6-tetrahydropyrrolo[3,4-c]pyrrol-2(1H)-yl)(tetrahydro-2H-pyran-3-yl)methanone | m/z: 364.0 | (400 MHz, CDCl$_3$): δ 8.73-8.69 (m, 1H), 8.03-7.88 (m, 2H), 7.56-7.42 (m,1H), 4.43-4.26 (m, 6H), 4.16 (d, J = 3.6 Hz, 2H), 3.98-3.87 (m, 2H), 3.54 (t, J = 12.0 Hz, 1H), 3.50-3.34 (m, 1H), 2.68-2.49 (m, 1H), 1.96-1.76 (m, 2H), 1.69-1.48 (m, 2H) | + | 0 | + |
| 45e | <br>(S)-(5-(pyridin-2-ylsulfonyl)-3,4,5,6-tetrahydropyrrolo[3,4-c]pyrrol-2(1H)-yl)(tetrahydro-2H-pyran-3-yl)methanone | m/z: 364.2 | (400 MHz, CDCl$_3$): δ 8.75-8.67 (m, 1H), 8.04-7.88 (m, 2H), 7.58-7.39 (m,1H), 4.43-4.26 (m, 6H), 4.18-4.16 (m, 2H), 4.00-3.89 (m, 2H), 3.54 (t, J = 12.0 Hz, 1H), 3.48-3.29 (m, 1H), 2.69-2.48 (m, 1H), 1.95-1.76 (m, 2H), 1.72-1.58 (m, 2H) | ++ | + | ++ |

FIGURE 1
(continued 16 of 20)

| Cpd. No. | Structure and Name | LCMS | $^1$H NMR | AC$_{50}$ (G332S) | AC$_{50}$ (R510Q) | AC$_{50}$ (WT) |
|---|---|---|---|---|---|---|
| 46 | 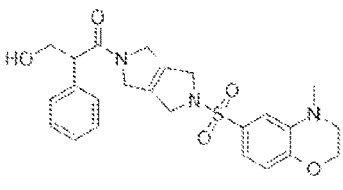 3-hydroxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)-2-phenylpropan-1-one | m/z: 470.2 | | 0 | 0 | +++ |
| 47 | 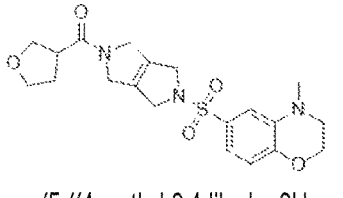 (5-((4-methyl-3,4dihydro-2H-benzo[b][1,4]oxazin-6-yl)sulfonyl)-3,4,5,6-tetrahydropyrrolo[3,4-c]pyrrol-2(1H)-yl)(tetrahydrofuran-3-yl)methanone | m/z: 420.2 | | 0 | + | ++ |
| 48 | 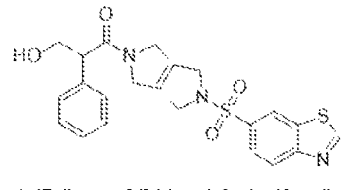 1-(5-(benzo[d]thiazol-6-ylsulfonyl)-3,4,5,6-tetrahydropyrrolo[3,4-c]pyrrol-2(1H)-yl)-3-hydroxy-2-phenylpropan-1-one | m/z: 456.1 | | +++ | +++ | +++ |

(continued 17 of 20)

| Cpd. No. | Structure and Name | LCMS | ¹H NMR | AC$_{50}$ (G332S) | AC$_{50}$ (R510Q) | AC$_{50}$ (WT) |
|---|---|---|---|---|---|---|
| 49 |  1-(5-((4-(difluoromethoxy)phenyl)sulfonyl)-3,4,5,6-tetrahydropyrrolo[3,4-c]pyrrol-2(1H)-yl)-3-hydroxy-2-phenylpropan-1-one | m/z: 465.1 | | +++ | +++ | +++ |
| 50 |  (2S)-3-hydroxy-2-phenyl-1-[5-pyridine-3-sulfonyl)-1H,2H,3H,4H,5H,6H-pyrrolo[3,4-c]pyrrol-2-yl]propan-1-one | m/z: 400.3 | | ++ | ++ | ++ |
| 51 |  (2S)-3-hydroxy-2-phenyl-1-[5-pyridine-2-sulfonyl)-1H,2H,3H,4H,5H,6H-pyrrolo[3,4-c]pyrrol-2-yl]propan-1-one | m/z: 400.3 | | ++ | +++ | +++ |

FIGURE 1
(continued 18 of 20)

| Cpd. No. | Structure and Name | LCMS | 1H NMR | AC50 (G332S) | AC50 (R510Q) | AC50 (WT) |
|---|---|---|---|---|---|---|
| 52 | 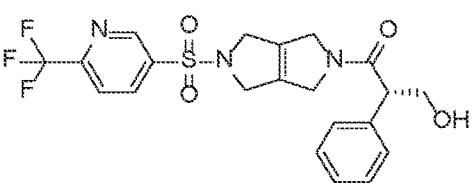<br>(2S)-3-hydroxy-2-phenyl-1-[5-{[6-(trifluoromethyl)pyridin-3-yl]sulfonyl}-1H,2H,3H,4H,5H,6H-pyrrolo[3,4-c]pyrrol-2-yl]propan-1-one | m/z: 468.2 | | ++ | + | ++ |
| 53 | 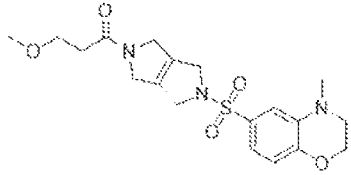<br>3-methoxy-1-(5-((4-methyl-3,4-dihydro-2H-benzo[b][1,4]oxazin-6-yl)sulfonyl)-3,4,5,6-tetrahydropyrrolo[3,4-c]pyrrol-2(1H)-yl)propan-1-one; and | m/z: 408.2 | | 0 | + | ++ |
| 54 | 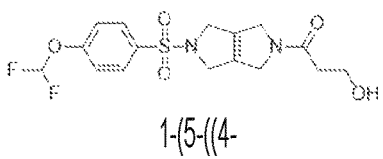<br>1-(5-((4-(difluoromethoxy)phenyl)sulfonyl)-3,4,5,6-tetrahydropyrrolo[3,4-c]pyrrol-2(1H)-yl)-3-hydroxypropan-1-one. | m/z: 391.1 | | | + | + |

(continued 19 of 20)

| Cpd. No. | Structure and Name | LCMS | 1H NMR | AC50 (G332S) | AC50 (R510Q) | AC50 (WT) |
|---|---|---|---|---|---|---|
| 55 |  (5-(benzofuran-5-ylsulfonyl)-3,4,5,6-tetrahydropyrrolo[3,4-c]pyrrol-2(1H)-yl)(tetrahydrofuran-3-yl)methanone | | | | | |
| 56 |  (5-(benzo[d]thiazol-6-ylsulfonyl)-3,4,5,6-tetrahydropyrrolo[3,4-c]pyrrol-2(1H)-yl)(morpholin-3-yl)methanone | | | 0 | + | |
| 57 |  1-(5-((2,3-dihydrobenzo[b][1,4]dioxin-6-yl)sulfonyl)-3,4,5,6-tetrahydropyrrolo[3,4-c]pyrrol-2(1H)-yl)-3-methoxypropan-1-one | | | +++ | ++ | |

FIGURE 1
(continued 20 of 20)

| Cpd. No. | Structure and Name | LCMS | 1H NMR | AC50 (G332S) | AC50 (R510Q) | AC50 (WT) |
|---|---|---|---|---|---|---|
| 58 | 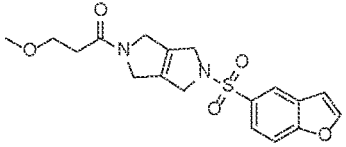<br>1-(5-(benzofuran-5-ylsulfonyl)-3,4,5,6-tetrahydropyrrolo[3,4-c]pyrrol-2(1H)-yl)-3-methoxypropan-1-one | | | +++ | ++ | | a Compounds 3 and 4 are enantiomers, but absolute stereochemistry is undetermined; b Compounds 5 and 6 are enantiomers, but absolute stereochemistry is undetermined; c Compounds 33 and 34 are enantiomers, but absolute stereochemistry is undetermined; d Compounds 41 and 42 are enantiomers, but absolute stereochemistry is undetermined; e Compounds 44 and 45 are enantiomers, but absolute stereochemistry is undetermined.

TREATING SICKLE CELL DISEASE WITH A PYRUVATE KINASE R ACTIVATING COMPOUND

CROSS-REFERENCE TO RELATED APPLICATIONS

This application is a National Stage application of International Application No. PCT/US2019/052024, filed Sep. 19, 2019, which claims the benefit of U.S. Provisional Application No. 62/733,558, filed on Sep. 19, 2018, U.S. Provisional Application No. 62/733,562, filed on Sep. 19, 2018, U.S. Provisional Application No. 62/782,933, filed on Dec. 20, 2018, U.S. Provisional Application No. 62/789,641, filed on Jan. 8, 2019, and U.S. Provisional Application No. 62/811,904, filed on Feb. 28, 2019, each of which is incorporated by reference in its entirety.

TECHNICAL FIELD

This disclosure relates to the treatment of sickle cell disease (SCD), including the treatment of patients diagnosed with SCD by the administration of a compound that activates pyruvate kinase R (PKR).

BACKGROUND

Sickle cell disease (SCD) is a chronic hemolytic anemia caused by inheritance of a mutated form of hemoglobin (Hgb), sickle Hgb (HgbS). It is the most common inherited hemolytic anemia, affecting 70,000 to 80,000 patients in the United States (US). SCD is characterized by polymerization of HgbS in red blood cells (RBCs) when HgbS is in the deoxygenated state (deoxy-HgbS), resulting in a sickle-shaped deformation. Sickled cells aggregate in capillaries precipitating vaso-occlusive events that generally present as acute and painful crises resulting in tissue ischemia, infarction, and long-term tissue damage. RBCs in patients with SCD tend to be fragile due to sickling and other factors, and the mechanical trauma of circulation causes hemolysis and chronic anemia. Finally, damaged RBCs have abnormal surfaces that adhere to and damage vascular endothelium, provoking a proliferative/inflammatory response that underlies large-vessel stroke and potentially pulmonary-artery hypertension. Collectively, these contribute to the significant morbidity and increased mortality associated with this disease.

Currently, therapeutic treatment of SCD is inadequate. The only known cure for SCD is hematopoietic stem cell transplantation which has serious risks, is typically recommended for only the most serious cases, and is largely offered only to children with sibling-matched donors. Gene therapy is also under investigation with promising preliminary results; however, there are market access hurdles, mainly high cost and treatment complexities, that are likely to limit its broad use in the near term. There have been few advances in therapies for SCD over the past two decades. Hydroxyurea (HU) induces HgbF which interrupts the polymerization of HgbS, and thereby has activity in decreasing the onset of vaso-occlusive crises and pathological sequelae of SCD. While HU is in wide use as a backbone therapy for SCD, it remains only partially effective, and is associated with toxicity, such as myelosuppression and teratogenicity. Patients receiving HU still experience hemolysis, anemia, and vaso-occlusive crises, suggesting a need for more effective therapies, either as a replacement or in combination with HU. Beyond HU, therapeutic intervention is largely supportive care, aimed at managing the symptoms of SCD. For instance, blood transfusions help with the anemia and other SCD complications by increasing the number of normal RBCs. However, repeated transfusions lead to iron overload and the need for chelation therapies to avoid consequent tissue damage. In addition to these approaches, analgesic medications are used to manage pain.

Given the current standard of care for SCD, there is a clear medical need for a noninvasive, disease-modifying therapy with appropriate safety and efficacy profiles.

SUMMARY

One aspect of the disclosure relates to methods of treating SCD comprising the administration of a therapeutically effective amount of a pyruvate kinase R (PKR) activator to a patient in need thereof diagnosed with SCD. Pyruvate kinase R (PKR) is the isoform of pyruvate kinase expressed in RBCs, and is a key enzyme in glycolysis. The invention is based in part on the discovery that the activation of PKR can target both sickling, by reducing deoxy-HgbS, and hemolysis. Targeting hemolysis may be achieved by improving RBC membrane integrity. One aspect of the disclosure is the recognition that activation of PKR can reduce 2,3-diphosphoglycerate (2,3-DPG), which leads to decreased deoxy-HgbS (and, therefore, sickling), as well as can increase ATP, which promotes membrane health and reduces hemolysis. Another aspect of the disclosure is the recognition that activation of PKR can reduce 2,3-diphosphoglycerate (2,3-DPG), which inhibits Hgb deoxygenation/increases oxygen affinity of HgbS and leads to decreased deoxy-HgbS (and, therefore, sickling), as well as can increase ATP, which promotes membrane health and reduces hemolysis. Accordingly, in one embodiment, PKR activation (e.g., by administration of a therapeutically effective amount of a PKR Activating Compound to a patient diagnosed with SCD) reduces RBC sickling via a reduction in levels of 2,3-diphosphoglycerate (2,3-DPG), which in turn reduces the polymerization of sickle Hgb (HgbS) into rigid aggregates that deform the cell. Furthermore, in some embodiments, PKR activation may contribute to overall RBC membrane integrity via increasing levels of adenosine triphosphate (ATP), which is predicted to reduce vaso-occlusive and hemolytic events which cause acute pain crises and anemia in SCD patients.

Preferably, a patient diagnosed with SCD is treated with a compound that is a PKR Activating Compound. The PKR activator can be a compound identified as a PKR Activating Compound or a composition identified as a PKR Activating Composition having an $AC_{50}$ value of less than 1 μM using the Luminescence Assay described in Example 2, or a pharmaceutically acceptable salt and/or other solid form thereof. For example, the PKR Activating Compound can be the compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one (Compound 1):

1

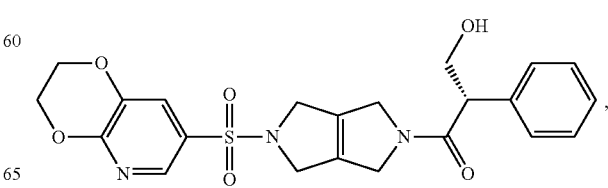

or a pharmaceutically acceptable salt thereof. Compound 1 is a selective, orally bioavailable PKR Activating Compound that decreases 2,3-DPG, increases ATP, and has anti-sickling effects in disease models with a wide therapeutic margin relative to preclinical toxicity.

PKR Activating Compounds can be readily identified as compounds of Formula I:

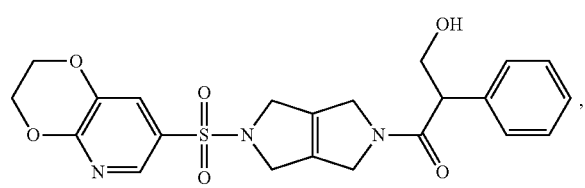

I or a pharmaceutically acceptable salt thereof, (e.g., Compound 1 and mixtures of Compound 1 with its stereoisomer) having an $AC_{50}$ value of less than 1 µM using the Luminescence Assay described in Example 2.

In other embodiments, the PKR Activating Compound can be any of the compounds listed in FIG. 1, or a pharmaceutically acceptable salt thereof.

PKR Activating Compounds, such as 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a pharmaceutically acceptable salt thereof, are useful in pharmaceutical compositions for the treatment of patients diagnosed with SCD. PKR Activating Compounds, such as any of the compounds listed in FIG. 1, or a pharmaceutically acceptable salt thereof, are useful in pharmaceutical compositions for the treatment of patients diagnosed with SCD. The compositions comprising a compound of Formula I (e.g., Compound 1), or a pharmaceutically acceptable salt thereof, can be obtained by certain processes also provided herein. The compositions comprising any of the compounds listed in FIG. 1, or a pharmaceutically acceptable salt thereof, can be obtained by certain processes also provided herein.

The methods of treating SCD provided herein can offer greater protection against vaso-occlusive crises and hemolytic anemia, as compared to existing and emerging therapies. Therefore, use of a PKR Activating Compound, such as Compound 1, provides a novel and improved therapeutic approach either alone or in combination with drugs that act through alternative mechanisms, such as hydroxyurea (HU). In addition, use of a PKR Activating Compound, such as any of the compounds listed in FIG. 1, provides a novel and improved therapeutic approach either alone or in combination with drugs that act through alternative mechanisms, such as hydroxyurea (HU).

BRIEF DESCRIPTION OF THE DRAWINGS

FIG. 8A shows each data point in grayscale, while FIG. 8B shows the same data with stylized lines.

DETAILED DESCRIPTION

Figure 1:
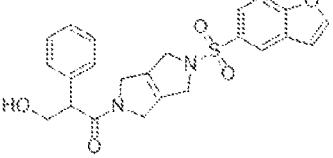
FIG. 1 is a table of PKR Activating Compounds.
Figure 1:
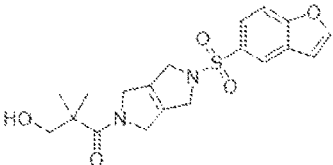
Figure 1:
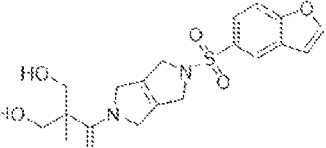
Figure 1:
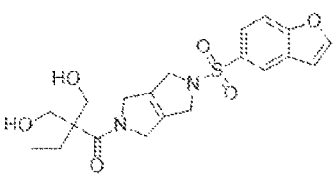
Figure 1:
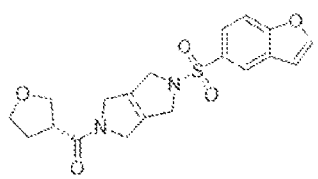
Figure 1:
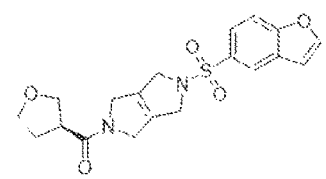
Figure 1:
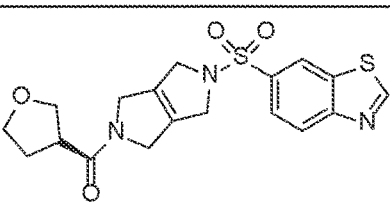
Figure 1:
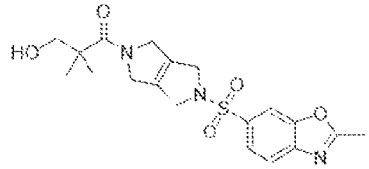
Figure 1:
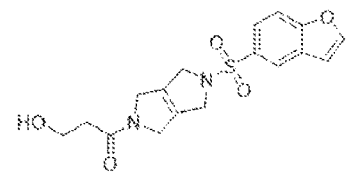
Figure 1:
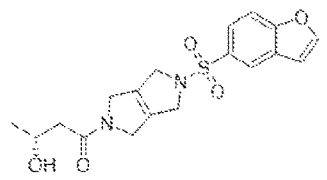
Figure 1:
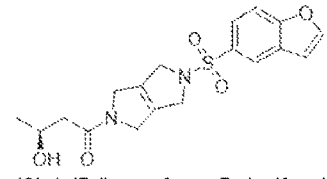
Figure 1:
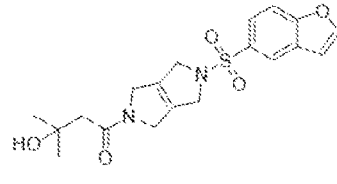
Figure 1:
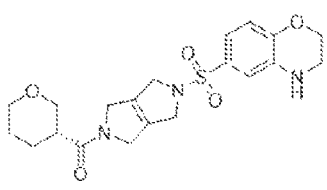
Figure 1:
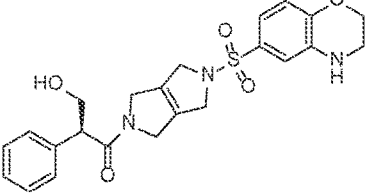
Figure 1:
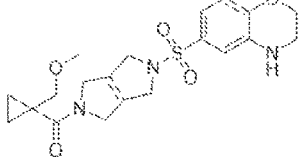
Figure 1:
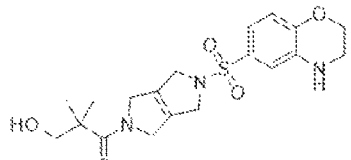
Figure 1:
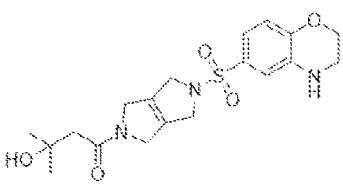
Figure 1:
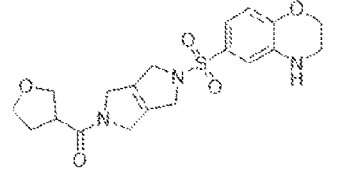
Figure 1:
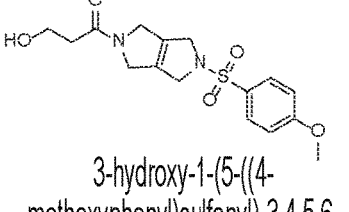
Figure 1:
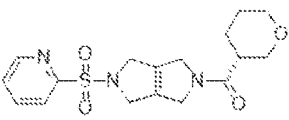
Figure 1:
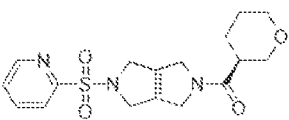
Figure 1:
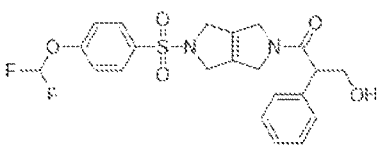
Figure 1:
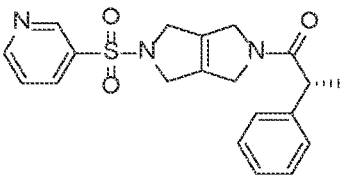
Figure 1:
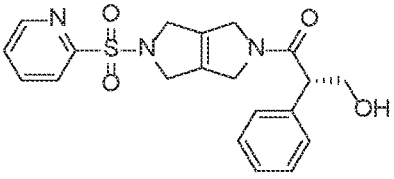
Figure 1:
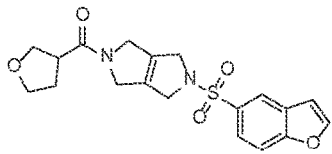
Figure 1:
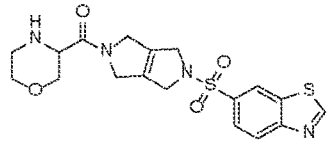
Figure 1:
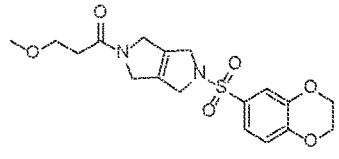

Methods of treating SCD preferably include administration of a therapeutically effective amount of a compound (e.g., Compound 1) that reduces HgbS polymerization, for example by increasing HgbS affinity for oxygen. Methods of treating SCD also preferably include administration of a therapeutically effective amount of a compound (e.g., any of the compounds listed in FIG. 1) that reduces HgbS polymerization, for example by increasing HgbS affinity for oxygen. Methods of lowering 2,3-DPG and/or increasing ATP levels in human RBCs comprise administering a PKR Activating Compound, such as Compound 1. Methods of lowering 2,3-DPG and/or increasing ATP levels in human RBCs also comprise administering a PKR Activating Compound, such as any of the compounds listed in FIG. 1. Together these effects are consistent with providing therapies to reduce HgbS sickling and to improve RBC membrane health, presenting a unique disease-modifying mechanism for treating SCD.

A PKR Activating Compound, such as Compound 1, is useful to promote activity in the glycolytic pathway. A PKR Activating Compound, such as any of the compounds listed in FIG. 1, also is useful to promote activity in the glycolytic pathway. As the enzyme that catalyzes the last step of glycolysis, PKR directly impacts the metabolic health and primary functions of RBCs. PKR Activating Compounds (e.g., Compound 1), are useful to decrease 2,3-DPG and increase ATP. PKR Activating Compounds (e.g., any of the compounds listed in FIG. 1), are useful to decrease 2,3-DPG and increase ATP. PKR Activating Compounds (e.g., Compound 1 or any of the compounds listed in FIG. 1, preferably Compound 1) are also useful to increase Hgb oxygen affinity in RBC. The disclosure is based in part on the discovery that PKR activation is a therapeutic modality for SCD, whereby HgbS polymerization and RBC sickling are reduced via decreased 2,3-DPG and increased ATP levels.

SCD is the most common inherited blood disorder and clinically manifests with potentially severe pathological conditions associated with substantial physical, emotional, and economic burden. For instance, acute vaso-occlusive pain crises can be debilitating and necessitate rapid medical response. Chronic hemolytic anemia causes fatigue and often necessitates blood transfusions and supportive care. Over time, impaired oxygen transport through microvasculature precipitates organ and tissue damage. While there are a number of options available for treating symptoms, overall disease management would benefit from therapies that target upstream processes to prevent vaso-occlusion and hemolysis.

The described clinical symptoms are largely due to perturbations in RBC membrane shape and function resulting from aggregation of HgbS molecules. Unlike normal Hgb, HgbS polymerizes when it is in the deoxygenated state and ultimately causes a deformed, rigid membrane that is unable to pass through small blood vessels, thereby blocking normal blood flow through microvasculature. The loss of membrane elasticity also increases hemolysis, reducing RBC longevity. Furthermore, decreased cellular ATP and oxidative damage contribute to a sickle RBC membrane that is stiffer and weaker than that of normal RBCs. The damaged membrane has a greater propensity for adhering to vasculature, leading to hemolysis, increased aggregation of sickled RBCs, and increased coagulation and inflammation associated with vaso-occlusive crises.

The underlying cause of sickling is the formation of rigid deoxy-HgbS aggregates that alter the cell shape and consequently impact cellular physiology and membrane elasticity. These aggregates are highly structured polymers of deoxygenated HgbS; the oxygenated form does not polymerize. Polymerization is promoted by a subtle shift in conformation from the oxygen-bound relaxed (R)-state to the unbound tense (T)-state. In the latter, certain residues within the β-chain of HgbS are able to interact in a specific and repetitive manner, facilitating polymerization.

Figure 3:
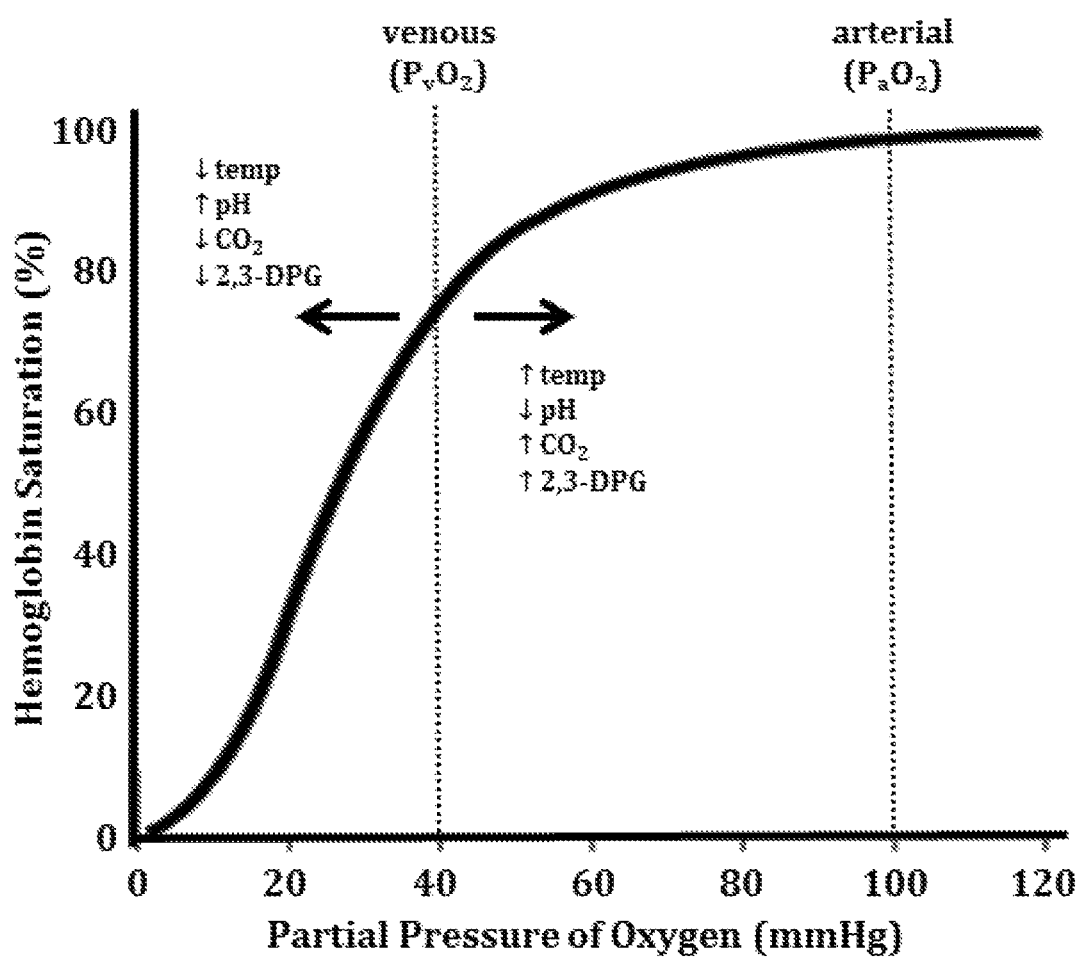
FIG. 3 is a graph showing the oxyhemoglobin dissociation curve and modulating factors by plotting the relationship between hemoglobin saturation (percent) vs. partial pressure of oxygen (mmHg).

The concentration of deoxy-HgbS depends on several factors, but the predominant factor is the partial pressure of oxygen ($PO_2$). Oxygen reversibly binds to the heme portions of the Hgb molecule. As oxygenated blood flows via capillaries to peripheral tissues and organs that are actively consuming oxygen, $PO_2$ drops and Hgb releases oxygen. The binding of oxygen to Hgb is cooperative and the relationship to $PO_2$ levels fits a sigmoidal curve (FIG. 3). This relationship can be impacted by temperature, pH, carbon dioxide, and the glycolytic intermediate 2,3-DPG. 2,3-DPG binds within the central cavity of the Hgb tetramer, causes allosteric changes, and reduces Hgb's affinity for oxygen. Therefore, therapeutic approaches that increase oxygen affinity (i.e., reduce deoxygenation) of HgbS would presumably decrease polymer formation, changes to the cell membrane, and clinical consequences associated with SCD.

Figure 2:
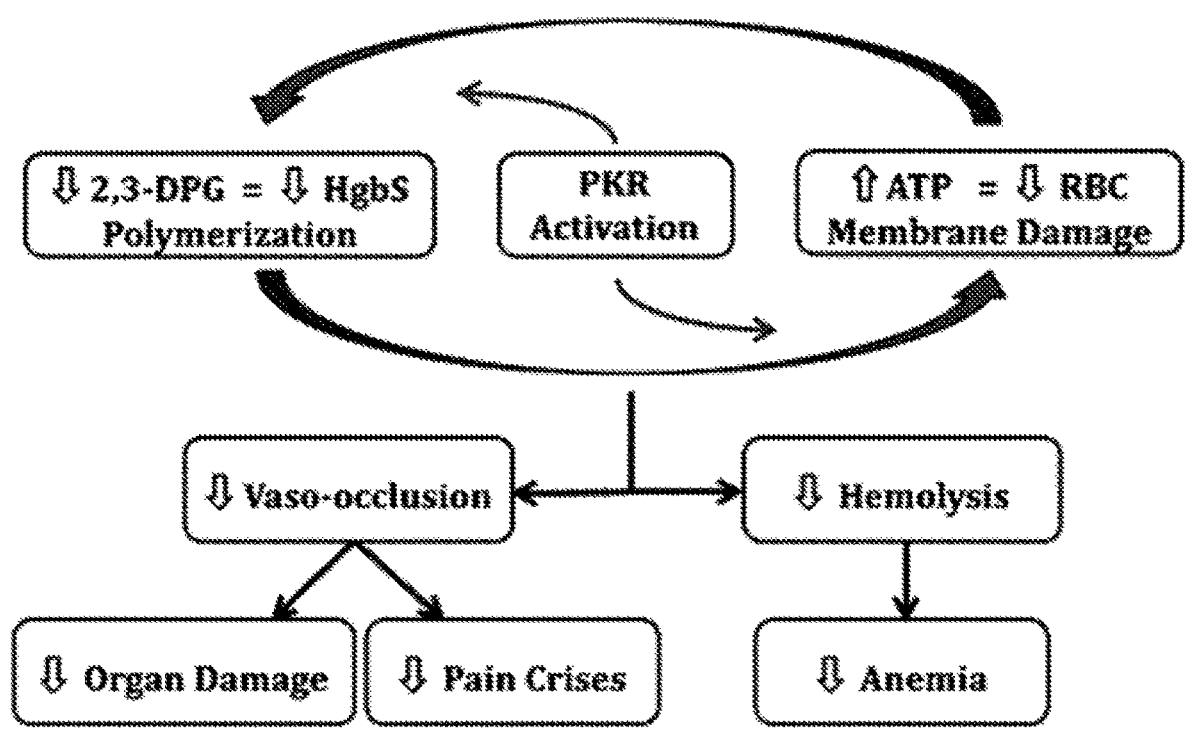
FIG. 2 is a schematic showing the relationship of PKR activation to the reduction of the clinical consequences of sickle cell disease (SCD).

One aspect of this disclosure is targeting PKR activation to reduce 2,3-DPG levels, based on PKR's role in controlling the rate of glycolysis in RBCs. A decrease in 2,3-DPG with PKR activation has been demonstrated in preclinical studies and in healthy volunteers and patients with pyruvate kinase deficiency. Additionally, PKR activation would be expected to increase ATP, and has been observed to do so in these same studies. Given the role of ATP in the maintenance of a healthy RBC membrane and protection from oxidative stress, elevating its levels is likely to have broad beneficial effects. Therefore, activation of PKR offers the potential for a 2,3-DPG effect (i.e., reduced cell membrane damage from HgbS polymerization) that is augmented by ATP support for membrane integrity. It is via these changes that a PKR activator is could positively impact physiological changes that lead to the clinical pathologies of SCD (FIG. 2). In another aspect, the disclosure relates to a method of improving the anemia and the complications associated with anemia in SCD patients (e.g., ≥12 years of age) with Hgb SS or Hgb SB⁰-thalassemia.

Compound 1 is a selective, orally bioavailable PKR activator that has been shown to decrease 2,3-DPG, increase ATP, and have anti-sickling effects in disease models with a wide therapeutic margin relative to preclinical toxicity.

Methods of treatment can comprise administering to a subject in need thereof a therapeutically effective amount of (i) a PKR Activating Compound (e.g., a compound disclosed herein), or a pharmaceutically acceptable salt thereof; or (ii) a PKR Activating Composition (e.g., a pharmaceutical composition comprising a compound disclosed herein, or a pharmaceutically acceptable salt thereof, and a pharmaceutically acceptable carrier). The pharmaceutical composition may be orally administered in any orally acceptable dosage form. In some embodiments, to increase the lifetime of red blood cells, a compound, composition, or pharmaceutical composition described herein is added directly to whole blood or packed cells extracorporeally or provided to the subject (e.g., the patient) directly. A patient and/or subject can be selected for treatment using a compound described herein by first evaluating the patient and/or subject to determine whether the subject is in need of activation of PKR, and if the subject is determined to be in need of activation of PKR, then administering to the subject a PKR Activating Compound in a pharmaceutically acceptable composition. A patient and/or subject can be selected for treatment using a compound described herein by first evaluating the patient and/or subject to determine whether the subject is diagnosed with SCD, and if the subject is diagnosed with SCD, then administering to the subject a PKR Activating Compound in a pharmaceutically acceptable composition. For example, administration of a therapeutically effective amount of a PKR Activating Compound can include administration of a total of about 25 mg-1,500 mg of Compound 1 each day, in single or divided doses. In some embodiments, Compound 1 is administered to patients diagnosed with SCD in total once daily (QD) doses of 25 mg, 50 mg, 75 mg, 100 mg, 125 mg, 150 mg, and/or higher if tolerated (e.g., 250 mg, 300 mg, 500 mg, 600 mg, 1000 mg, and/or 1500 mg). In some embodiments, a human dose of 80 to 130 mg of Compound 1 is administered once daily (QD) to a patient in need thereof (e.g., a patient diagnosed with SCD). In some embodiments, a PKR Activating Compound is administered in an amount of 400 mg per day (e.g., 400 mg QD or 200 mg BID). In some embodiments, Compound 1 or a pharmaceutically acceptable salt thereof is administered in an amount of 400 mg per day (e.g., 400 mg QD or 200 mg BID). In some embodiments, any of the compounds listed in FIG. 1 or a pharmaceutically acceptable salt thereof is administered in an amount of 400 mg per day (e.g., 400 mg QD or 200 mg BID). In some embodiments, a PKR Activating Compound is administered in an amount of 700 mg per day (e.g., 700 mg QD or 350 mg BID). In some embodiments, Compound 1 or a pharmaceutically acceptable salt thereof is administered in an amount of 700 mg per day (e.g., 700 mg QD or 350 mg BID). In some embodiments, any of the compounds listed in FIG. 1 or a pharmaceutically acceptable salt thereof is administered in an amount of 700 mg per day (e.g., 700 mg QD or 350 mg BID). In some embodiments, a PKR Activating Compound is administered in an amount of 100 mg, 200 mg, 400 mg, 600 mg, 700 mg, 1100 mg, or 1500 mg per day, in single or divided doses. In some embodiments, Compound 1 or a pharmaceutically acceptable salt thereof is administered in an amount of 100 mg, 200 mg, 400 mg, 600 mg, 700 mg, 1100 mg, or 1500 mg per day, in single or divided doses. In some embodiments, any of the compounds listed in FIG. 1 or a pharmaceutically acceptable salt thereof is administered in an amount of 100 mg, 200 mg, 400 mg, 600 mg, 700 mg, 1100 mg, or 1500 mg per day, in single or divided doses.

Methods of treating a patient diagnosed with SCD can include administering to the patient in need thereof a therapeutic compound targeting reduction of deoxy-HgbS, which may or may not directly improve RBC membrane integrity. Compound 1 has been shown to decrease 2,3-DPG and increase ATP, and reduced cell sickling has been demonstrated in disease models. Accordingly, in some embodiments, the methods of treatment can address not only sickling, but also hemolysis and anemia.

Methods of treating a patient diagnosed with sickle cell disease, and PKR Activating Compounds for use in such methods, can include administering to the patient the PKR Activating Compound (e.g., a composition comprising one or more compounds of Formula I, such as Compound 1 or a mixture of Compound 1 and Compound 2) in an amount sufficient to reduce 2,3-DPG levels in the patient's red blood cells. In some embodiments, the amount is sufficient to reduce 2,3-DPG levels by at least 30% after 24 hours, or greater (e.g., reducing 2,3-DPG levels in the patient's red blood cells by at least 40% after 24 hours). In some embodiments, the amount is sufficient to reduce 2,3-DPG levels by 30-50% after 24 hours. In some embodiments, the amount is sufficient to reduce 2,3-DPG levels by 40-50% after 24 hours. In some embodiments, the amount is sufficient to reduce 2,3-DPG levels by at least 25% after 12 hours. In some embodiments, the amount is sufficient to reduce 2,3-DPG levels by 25-45% after 12 hours. In some embodiments, the amount is sufficient to reduce 2,3-DPG levels by at least 15% after 6 hours. In some embodiments, the amount is sufficient to reduce 2,3-DPG levels by 15-30% after 6 hours. In some embodiments, the amount is sufficient to reduce 2,3-DPG levels by at least 40% on day 14 of treatment. In some embodiments, the amount is sufficient to reduce 2,3-DPG levels by 40-60% on day 14 of treatment. In some embodiments, the amount is sufficient to reduce 2,3-DPG levels by at least 50% on day 14 of treatment. In some embodiments, the amount is sufficient to reduce 2,3-DPG levels by 50-60% on day 14 of treatment.

Methods of treating a patient diagnosed with sickle cell disease, and PKR Activating Compounds for use in such methods, can also include administering to the patient the PKR Activating Compound (e.g., a composition comprising one or more compounds of Formula I, such as Compound 1 or a mixture of Compound 1 and Compound 2) in a daily amount sufficient to increase the patient's ATP blood levels. In some embodiments, the amount is sufficient to increase ATP blood levels by at least 40% on day 14 of treatment, or greater (e.g., t least 50% on day 14 of treatment). In some embodiments, the amount is sufficient to increase ATP blood levels by 40-65% on day 14 of treatment. In some embodiments, the amount is sufficient to increase ATP blood levels by at least 50% on day 14 of treatment, or greater (e.g., at least 50% on day 14 of treatment). In some embodiments, the amount is sufficient to increase ATP blood levels by 50-65% on day 14 of treatment.

In some examples, a pharmaceutical composition comprising Compound 1 can be used in a method of treating a patient diagnosed with sickle cell disease, the method comprising administering to the patient 400 mg of Compound 1 once per day (QD)

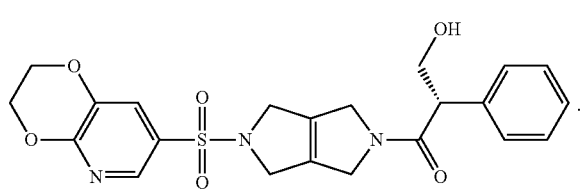

In some examples, a pharmaceutical composition comprising Compound 1 can be used in a method of treating a patient diagnosed with sickle cell disease, the method comprising administering to the patient 200 mg of Compound 1 twice per day (BID)

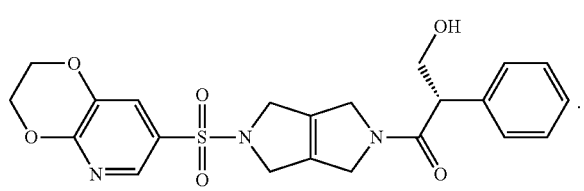

In some embodiments, the present disclosure provides PKR Activating Compounds of Formula I:

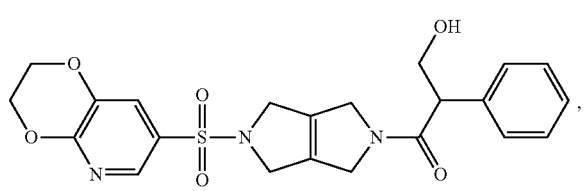

or a pharmaceutically acceptable salt thereof. In some embodiments, a PKR Activating Compound is 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

The compound of Formula I is preferably Compound 1:

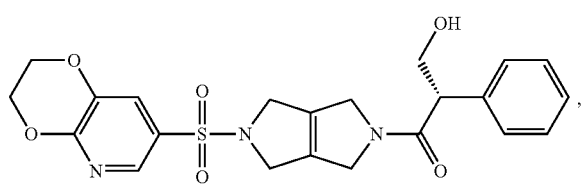

or a pharmaceutically acceptable salt thereof. In some embodiments, a compound of Formula I is (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

In some embodiments, the present disclosure provides a PKR Activating Compound that is any of the compounds listed in FIG. 1, or a pharmaceutically acceptable salt thereof.

The present disclosure also provides compositions (e.g. pharmaceutical compositions) comprising a compound of Formula I. In some embodiments, a provided composition containing a compound of Formula I comprises a mixture of Compound 1 and Compound 2:

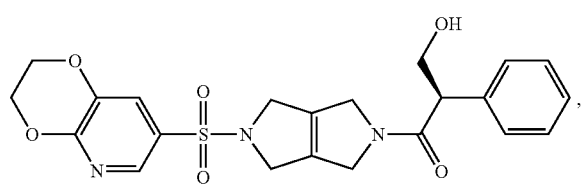

or a pharmaceutically acceptable salt thereof. The present disclosure also provides compositions (e.g. pharmaceutical compositions) comprising any of the compounds listed in FIG. 1, or a pharmaceutically acceptable salt thereof.

Pharmaceutical compositions comprising a PKR Activating Composition containing a compound of Formula (I) can be formulated for oral administration (e.g., as a capsule or tablet). For example, Compound 1 can be combined with suitable compendial excipients to form an oral unit dosage form, such as a capsule or tablet, containing a target dose of Compound 1. The drug product can be prepared by first manufacturing Compound 1 as an active pharmaceutical ingredient (API), followed by roller compaction/milling with intragranular excipients and blending with extra granular excipients. A Drug Product can contain the Compound 1 API and excipient components in Table 1 in a tablet in a desired dosage strength of Compound 1 (e.g., a 25 mg or 100 mg tablet formed from a Pharmaceutical Composition in Table 1). The blended material can be compressed to form tablets and then film coated.

The pharmaceutical composition preferably comprises about 30-70% by weight of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, and a pharmaceutically acceptable excipient in an oral dosage form.

TABLE 1

Exemplary Pharmaceutical Compositions of Compound 1 for Oral Administration

| Function | % Formulation (weight) | Exemplary Component |
| --- | --- | --- |
| API | 30-70% | Compound 1 |
| Filler | 15-40% | Microcrystalline Cellulose |
| Dry binder | 2-10% | Crospovidone Kollidon CL |
| Glidant | 0.25-1.25% | Colloidal Silicon Dioxide |
| Lubricant | 0.25-1.00% | Magnesium Stearate, Hyqual |

In some embodiments, a provided composition containing a compound of Formula I comprises a mixture of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one and (R)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one. In some embodiments, a provided composition containing a compound of Formula I is a mixture of Compound 1 and Compound 2 as part of a PKR Activating Composition. In some embodiments, a compound of Formula I is racemic. In some embodiments, a compound of Formula I consists of about 50% of Compound 1 and about 50% of Compound 2. In some embodiments, a compound of Formula I is not racemic. In some embodiments, a compound of Formula I does not consist of about 50% of Compound 1 and about 50% of Compound 2. In some embodiments, a compound of Formula I comprises about 99-95%, about 95-90%, about 90-80%, about 80-70%, or about 70-60% of Compound 1. In some embodiments, a compound of Formula I comprises about 99%, 98%, 95%, 90%, 80%, 70%, or 60% of Compound 1.

In some embodiments, a PKR Activating Composition comprises a mixture of Compound 1 and Compound 2. In some embodiments, a PKR Activating Composition comprises a mixture of Compound 1 and Compound 2, wherein the PKR Activating Composition comprises a therapeutically effective amount of Compound 1.

Figure 4A:
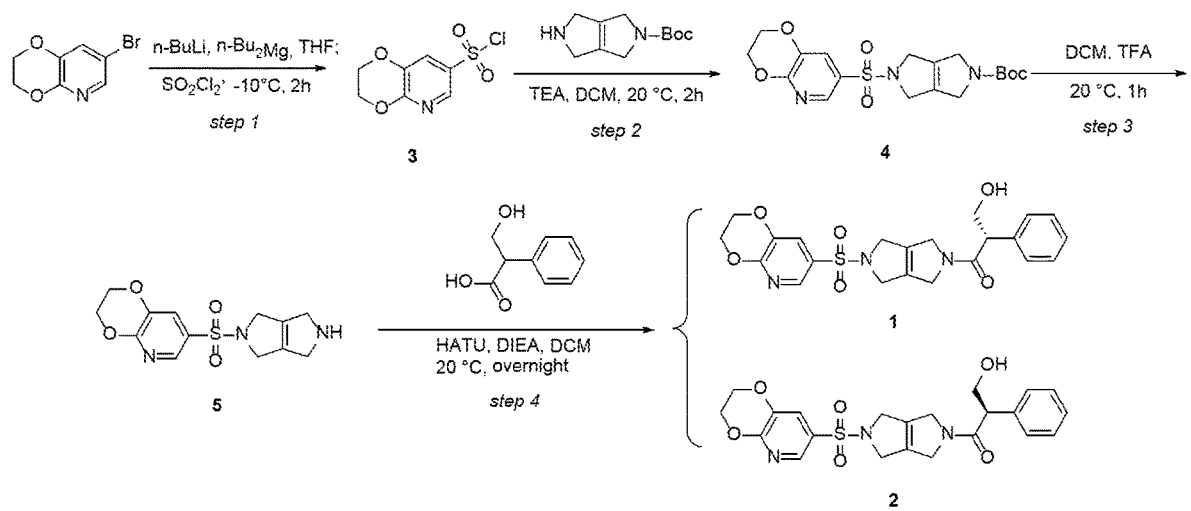
FIG. 4A is a chemical synthesis scheme for compounds of Formula I, including a synthesis of Compound 1 (separately provided in FIG. 4B).
Figure 4B:
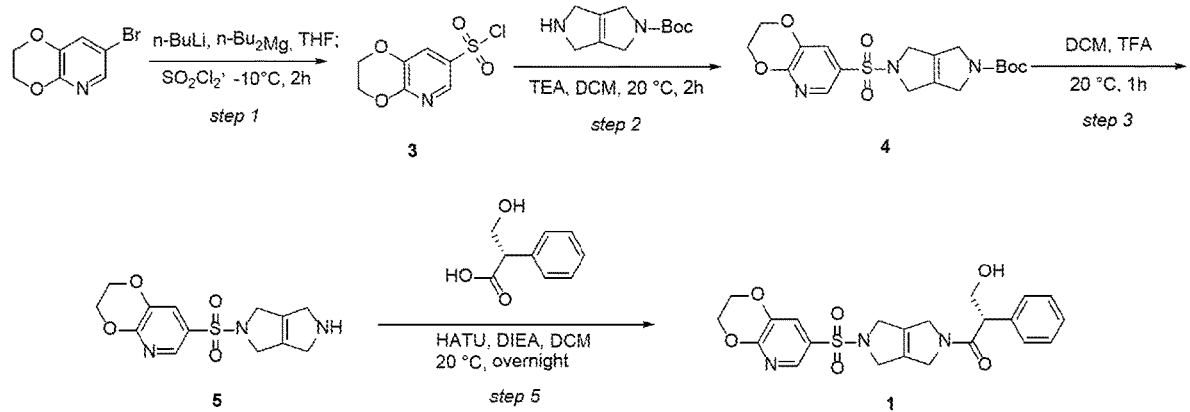
FIG. 4B is a chemical synthesis scheme for Compound 1.

Compositions comprising a compound of Formula I can be prepared as shown in FIG. 4A and FIG. 4B. Compounds of Formula I can be obtained by the general chemical synthesis scheme of FIG. 4A. Compound 1 can be obtained by the chemical synthesis route of FIG. 4A or FIG. 4B. In brief, compounds of Formula I (FIG. 4A) and/or Compound 1 (FIG. 4B) can be obtained from a series of four reaction steps from commercially available starting materials. Commercially available 7-bromo-2H,3H-[1,4]dioxino[2,3-b]pyridine was treated with a mixture of n-butyl lithium and dibutylmagnesium followed by sulfuryl chloride to give sulfonyl chloride 3. Treatment of 3 with tert-butyl 1H,2H,3H,4H,5H,6H-pyrrolo[3,4-c]pyrrole-2-carboxylate in the presence of triethylamine (TEA) afforded Boc-protected monosulfonamide 4. Compound 4 was then de-protected in the presence of trifluoroacetic acid (TFA) to give 5, the free base of the monosulfonamide. The last step to generate Compound 1 (FIG. 4B) or Compound 1 and Compound 2 (FIG. 4A) was an amide coupling of 5 and tropic acid in the presence of 1-[bis(dimethylamino)methylene]-1H-1,2,3-triazolo[4,5-b]pyridinium 3-oxide hexafluoro-phosphate (HATU).

Figure 4C:
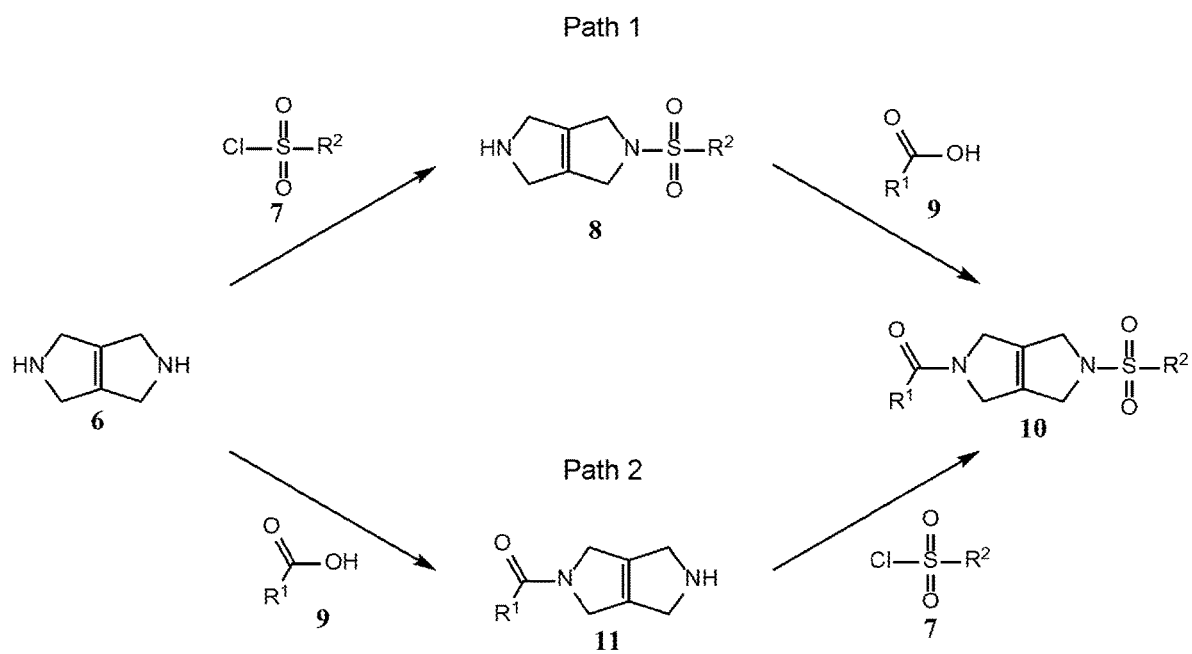
FIG. 4C is a general chemical synthesis of the compounds listed in FIG. 1.

The compounds listed in FIG. 1 can be prepared as shown in FIG. 4C and as described in International Publication No. WO 2018/175474, published Sep. 27, 2018. Generally, the compounds listed in FIG. 1 can be prepared by acylation and sulfonylation of the secondary amine groups of hexahydropyrrolopyrrole 6. For example, sulfonylation of 6 with a suitable sulfonyl chloride 7 affords sulfonyl hexahydropyrrolopyrrole 8, which is then treated with a suitable carboxylic acid 9 in the presence of an amide coupling reagent (e.g., HATU) to afford compound 10 (Path 1). Alternatively, acylation of 6 with a suitable carboxylic acid 9 in the presence of an amide coupling reagent affords acyl hexahydropyrrolopyrrole 11, which is then treated with a suitable sulfonyl chloride 7 to afford compound 10 (Path 2). As a person of ordinary skill would understand, well-known protecting groups, functionalization reactions, and separation techniques can be used in conjunction with Paths 1 and 2 to obtain the specific compounds listed in FIG. 1.

Methods of treating SCD also include administration of a therapeutically effective amount of a bioactive compound (e.g., a small molecule, nucleic acid, or antibody or other therapy) that reduces HgbS polymerization, for example by increasing HgbS affinity for oxygen. In some embodiments, a method of treating SCD comprises administering to a patient in need thereof a bioactive compound that reduces the percent of sickled cells in a murine model of sickle cell disease provided in Example 7 herein following 7 days of oral treatment with the compound. In some embodiments, the bioactive compound is any compound (including small molecules, nucleic acids, proteins or antibodies) that, in the murine model of sickle cell disease provided in Example 7, exhibits one or more of the following characteristics: (a) increases oxygen affinity to Hgb in hypoxic conditions; (b) decreases P50 in hypoxic conditions; (c) decreases the percentage of RBCs that sickle at low oxygen pressures; (d) increases the time of a cell to sickle; and/or (e) increases Hgb by at least approximately 1 g/dL.

In other embodiments, the disclosure relates to each of the following numbered embodiments:

1. A composition comprising a PKR Activating Compound of Formula I, or a pharmaceutically acceptable salt thereof:

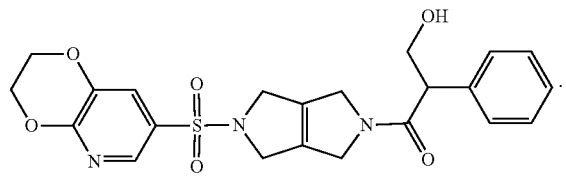

2. The composition of embodiment 1, wherein the compound of Formula I is Compound 1, or a pharmaceutically acceptable salt thereof:

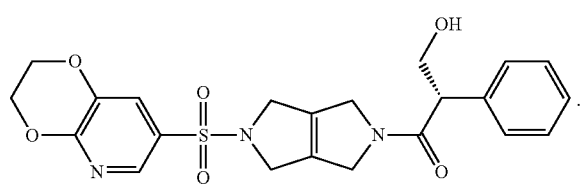

3. The composition of embodiment 2, wherein the composition comprises a mixture of Compound 1 and Compound 2, or a pharmaceutically acceptable salt thereof:

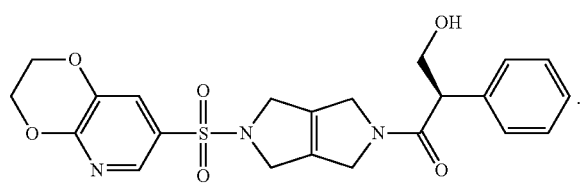

4. The composition of embodiment 1, comprising the compound: 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

5. The composition of any one of embodiments 1-4, formulated as an oral unit dosage form.

6. A method of treating a patient diagnosed with a sickle cell disease (SCD), the method comprising administering to the patient in need thereof a therapeutically effective amount of a pharmaceutical composition comprising (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a pharmaceutically acceptable salt thereof.

7. The method of embodiment 6, wherein the method comprises oral administration of the pharmaceutical composition comprising (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, as the only PKR Activating Compound in the pharmaceutical composition.

8. A method of treating a patient diagnosed with a sickle cell disease (SCD), the method comprising administering to the patient in need thereof a therapeutically effective amount of a pharmaceutical composition comprising Compound 1:

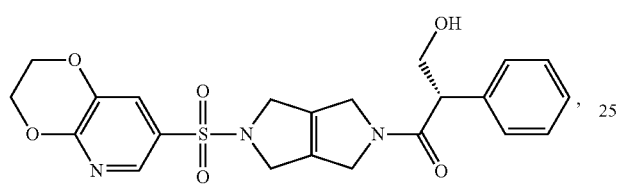

or a pharmaceutically acceptable salt thereof.

9. A composition comprising a compound of Formula I obtainable by a process comprising the step of converting compound 5 into a compound of Formula I in a reaction described as Step 4:

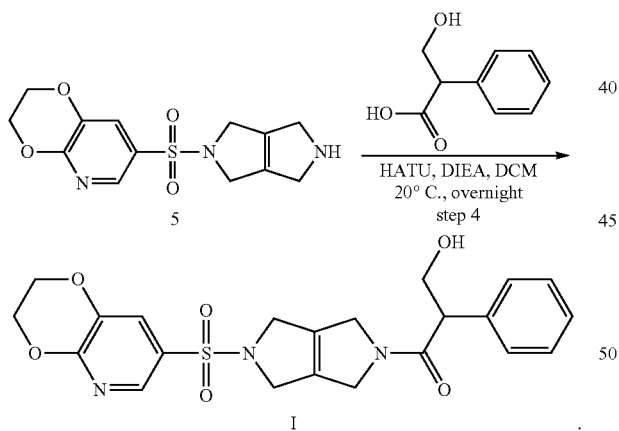

10. The composition of embodiment 9, wherein the process further comprises first obtaining the compound 5 from a compound 4 by a process comprising Step 3:

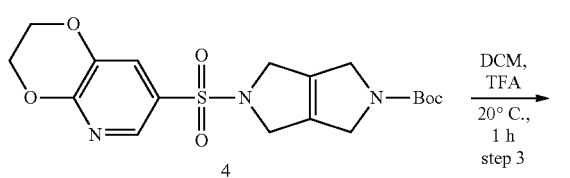

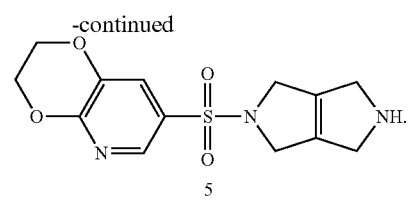

11. The composition of embodiment 10, wherein the process further comprises first obtaining the compound 4 from a compound 3 by a process comprising Step 2:

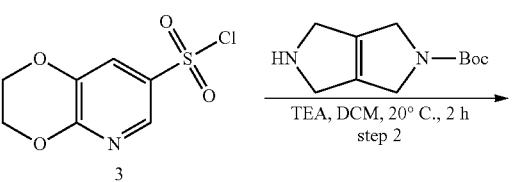

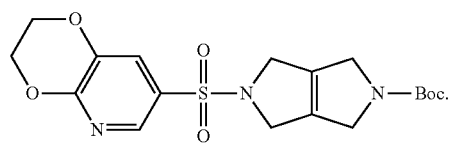

12. The composition of embodiment 11, wherein the process further comprises first obtaining the compound 3 from a process comprising Step 1:

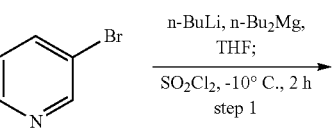

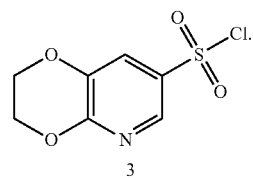

13. A method of treating a patient diagnosed with sickle cell disease (SCD), the method comprising administering to the patient in need thereof a therapeutically effective amount of a PKR Activating Compound having an $AC_{50}$ value of less than 1 μM using the Luminescence Assay described in Example 2.

14. The method of embodiment 13, wherein the PKR Activating Compound is Compound 1.

15. The method of any one of embodiments 13-14, wherein the PKR Activating Compound is orally administered to the patient in need thereof.

16. The use of Compound 1:

or a pharmaceutically acceptable salt thereof, for the treatment of patients diagnosed with sickle cell disease (SCD).

17. The use of a PKR Activating Compound having an AC$_{50}$ value of less than 1 µM using the Luminescence Assay described in Example 2, in the treatment of patients diagnosed with sickle cell disease.

18. The method of any one of embodiments 6-8 or 13-15, comprising the administration of Compound 1 once per day.

19. The method of any one of embodiments 6-8 or 13-15, comprising the administration of a total of 25 mg-1,500 mg of Compound 1 each day.

20. The method of any one of embodiments 18-19, comprising the administration of a total of 25 mg-130 mg of Compound 1 each day.

21. A method of treating a patient diagnosed with SCD, comprising the administration to the patient of a therapeutically effective amount of a PKR Activating Compound, wherein the PKR Activating Compound, in the murine model of sickle cell disease provided in Example 10, exhibits one or more of the following characteristics: (a) increases oxygen affinity to Hgb in hypoxic conditions; (b) decreases P50 in hypoxic conditions; (c) decreases the percentage of RBC that sickle at low oxygen pressures; (d) increases the time of a cell to sickle; and/or (e) increases Hgb by at least approximately 1 g/dL.

22. The method of embodiment 21, wherein the PKR Activating Compound is an antibody.

23. The method of embodiment 21, wherein the PKR Activating Compound is a protein.

24. The method of embodiment 21, wherein the PKR Activating Compound is a nucleic acid.

25. The method of embodiment 21, wherein the PKR Activating Compound is a DNA nucleic acid.

26. The method of embodiment 21, wherein the PKR Activating Compound is a RNA nucleic acid.

In other embodiments, the disclosure relates to each of the following numbered embodiments:

1. A PKR Activating Compound for use in a method of treating a patient diagnosed with sickle cell disease (SCD), comprising administering to the patient the PKR Activating Compound in a therapeutically effective amount, wherein the PKR Activating Compound is a compound of Formula I:

or a pharmaceutically acceptable salt thereof, having an AC$_{50}$ value of less than 1 µM using the Luminescence Assay described in Example 2.

2. The PKR Activating Compound of embodiment 1, wherein the PKR Activating Compound is Compound 1:

or a pharmaceutically acceptable salt thereof.

3. The PKR Activating Compound of embodiment 1, wherein the PKR Activating Compound is Compound 1:

4. The PKR Activating Compound of embodiment 3, wherein the PKR Activating Compound is administered in an amount of 25-1500 mg per day.

5. The PKR Activating Compound of embodiment 3, wherein the PKR Activating Compound is administered once daily in an amount of 250 mg, 300 mg, 500 mg, 600 mg, 1000 mg, or 1500 mg per day.

6. The PKR Activating Compound of embodiment 3, wherein the PKR Activating Compound is administered once daily in an amount of 100 mg per day.

7. The PKR Activating Compound of embodiment 3, wherein the PKR Activating Compound is administered once daily in an amount of 600 mg per day.

8. The PKR Activating Compound of embodiment 3, wherein the PKR Activating Compound is administered once per day.

9. The PKR Activating Compound of embodiment 3, wherein the PKR Activating Compound is orally administered to the patient.

10. The PKR Activating Compound of embodiment 3, wherein Compound 1 is the only PKR Activating Compound administered to the patient.

11. A PKR Activating Compound for use in a method of treating a patient diagnosed with sickle cell disease, comprising administering to the patient the PKR Activating Compound in an amount sufficient to reduce 2,3-DPG levels in the patient's red blood cells by at least 30% after 24 hours, wherein the PKR Activating Compound is a compound of Formula I.

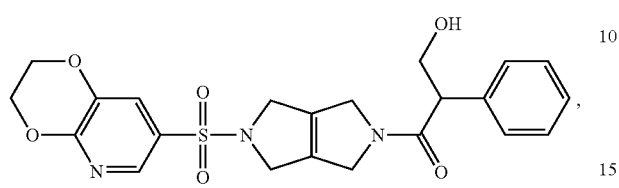

or a pharmaceutically acceptable salt thereof, having an AC$_{50}$ value of less than 1 µM using the Luminescence Assay described in Example 2.

12. The PKR Activating Compound of embodiment 11, wherein the PKR Activating Compound is Compound 1:

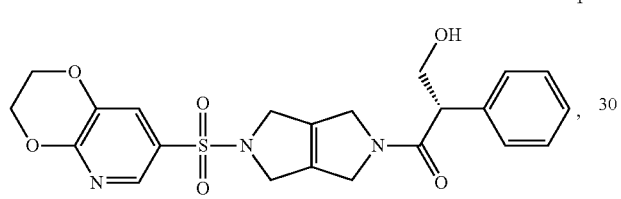

or a pharmaceutically acceptable salt thereof.

13. The PKR Activating Compound of embodiment 1, wherein the PKR Activating Compound is Compound 1:

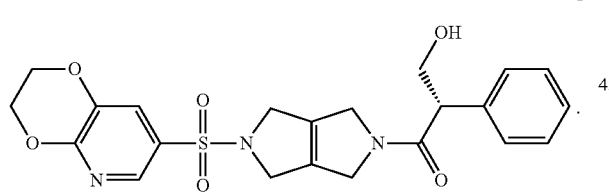

14. The PKR Activating Compound of embodiment 13, wherein Compound 1 is the only PKR Activating Compound administered to the patient.

15. The PKR Activating Compound of any one of embodiments 11-14, wherein the PKR Activating Compound is orally administered to the patient.

16. The PKR Activating Compound of any one of embodiments 11-15, wherein the PKR Activating Compound is administered once per day.

17. The PKR Activating Compound of any one of embodiments 11-16, wherein the PKR Activating Compound is administered in an amount sufficient to reduce 2,3-DPG levels in the patient's red blood cells by at least 40% after 24 hours.

18. The PKR Activating Compound of any one of embodiments 11-17, wherein the PKR Activating Compound is administered in a daily amount sufficient to increase the patient's ATP blood levels by at least 40% on day 14 of treatment.

19. The PKR Activating Compound of any one of embodiments 11-15, wherein the PKR Activating Compound is administered in an amount of 100 mg, 200 mg, 400 mg, 600 mg, 700 mg, 1100 mg, or 1500 mg per day.

20. The PKR Activating Compound of any one of embodiments 11-15, wherein the PKR Activating Compound is administered in an amount of 200 mg per day.

21. The PKR Activating Compound of embodiment 20, wherein the PKR Activating Compound is administered in an amount of 200 mg per day once per day (QD).

22. The PKR Activating Compound of embodiment 20, wherein the PKR Activating Compound is administered in an amount of 100 mg per day twice per day (BID).

23. The PKR Activating Compound of any one of embodiments 11-15, wherein the PKR Activating Compound is administered in an amount of 400 mg per day.

24. The PKR Activating Compound of embodiment 23, wherein the PKR Activating Compound is administered in an amount of 400 mg once per day (QD).

25. The PKR Activating Compound of embodiment 23, wherein the PKR Activating Compound is administered in an amount of 200 mg twice per day (BID).

26. The PKR Activating Compound of any one of embodiments 11-15, wherein the PKR Activating Compound is administered in an amount of 600 mg per day.

27. The PKR Activating Compound of embodiment 26, wherein the PKR Activating Compound is administered in an amount of 300 mg twice per day (BID).

28. The PKR Activating Compound of any one of embodiments 11-15, wherein the PKR Activating Compound is administered in an amount of 700 mg per day.

29. The PKR Activating Compound of embodiment 28, wherein the PKR Activating Compound is administered in an amount of 700 mg once per day (QD).

30. The PKR Activating Compound of embodiment 28, wherein the PKR Activating Compound is administered in an amount of 350 mg twice per day (BID).

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description and drawings are by way of example to illustrate the discoveries provided herein.

EXAMPLES

As the enzyme that catalyzes the last step of glycolysis, PKR underlies reactions that directly impact the metabolic health and primary functions of RBCs. The following Examples demonstrate how PKR activation by Compound 1 impacts RBCs. The primary effect of Compound 1 on RBCs is a decrease in 2,3-DPG that is proposed to reduce Hgb sickling and its consequences on RBCs and oxygen delivery to tissues. Compound 1 also increases ATP, which may provide metabolic resources to support cell membrane integrity and protect against loss of deformability and increased levels of hemolysis in SCD. With the combination of effects Compound 1 has on RBCs, it is likely to reduce the clinical sequelae of sickle Hgb and provide therapeutic benefits for patients with SCD.

The PKR Activating Compound designated Compound 1 was prepared as described in Example 1, and tested for PKR activating activity in the biochemical assay of Example 2.

The biological enzymatic activity of PKR (i.e., formation of ATP and/or pyruvate) was evaluated in enzyme and cell assays with Compound 1, as described in Example 3 and Example 4, respectively. Results from enzyme assays show that Compound 1 is an activator of recombinant wt-PKR and mutant PKR, (e.g., R510Q), which is one of the most prevalent PKR mutations in North America. PKR exists in both a dimeric and tetrameric state, but functions most efficiently as a tetramer. Compound 1 is an allosteric activator of PKR and is shown to stabilize the tetrameric form of PKR, thereby lowering the $K_m$ (the Michaelis-Menten constant) for PEP.

Similarly, results from assays with RBCs from human patients with SCD showed that treatment with Compound 1 caused a shift in P50 ($PO_2$ at 50% hemoglobin saturation) and that this shift was related to increased oxygen affinity in the presence of Compound 1 (Example 5). Furthermore, Compound 1 decreased sickling under severe hypoxic conditions. Taken together the data suggest that Compound 1 can reduce the clinical consequences of sickled cells by decreasing cell sickling through an increase in oxygen affinity that comes from PKR activation.

In vivo testing in mice (Examples 6 and 7) demonstrated PKR activation in wt mice, and provided an evaluation of effects on RBCs and Hgb in a murine model of SCD. Compound 1 was well tolerated up to the highest dose tested, and exposures increased in a dose-proportional manner. Levels of 2,3-DPG were reduced by >30% for doses ≥120 mg/kg Compound 1 (AUC from 0 to 24 hours ($AUC_{0-24}$>5200 hr·ng/mL) and levels of ATP were increased by >40% for ≥60 mg/kg Compound 1 ($AUC_{0-24}$>4000 hr·ng/mL). In two studies with a murine model of SCD, increased oxygen affinity, decreased sickling, and increased Hgb were observed ex vivo in RBCs from mice following 7 days of oral (chow) administration of Compound 1. Taken together, the data support exposure-related therapeutic benefits of Compound 1 for treatment of SCD.

In some embodiments, a daily dose of between 100 mg to 1500 mg of a PKR Activating Compound is administered to humans. In some embodiments, a daily dose of between 100 mg to 1500 mg of Compound 1 is administered to humans. In some embodiments, a daily dose of between 100 mg to 1500 mg of any of the compounds listed in FIG. 1 is administered to humans. In particular, a total daily dose of 100 mg-600 mg of a PKR Activating Compound can be administered to humans (including, e.g., a dose of 100 mg, 200 mg, 300 mg, 400 mg, 500 mg, or 600 mg, per day, in single or divided doses). In particular, a total daily dose of 100 mg-600 mg of Compound 1 can be administered to humans (including, e.g., a dose of 100 mg, 200 mg, 300 mg, 400 mg, 500 mg, or 600 mg, per day, in single or divided doses). In particular, a total daily dose of 100 mg-600 mg of any of the compounds listed in FIG. 1 can be administered to humans (including, e.g., a dose of 100 mg, 200 mg, 300 mg, 400 mg, 500 mg, or 600 mg, per day, in single or divided doses). In some embodiments, a daily dose of 400 mg (e.g., 400 mg QD or 200 mg BID) of a PKR Activating Compound is administered to humans. In some embodiments, a daily dose of 400 mg (e.g., 400 mg QD or 200 mg BID) of Compound 1, or a pharmaceutically acceptable salt thereof, is administered to humans. In some embodiments, a daily dose of 400 mg (e.g., 400 mg QD or 200 mg BID) of any of the compounds listed in FIG. 1 is administered to humans.

Example 1: Synthesis of Compounds of Formula I

The PKR Activating Compound 1 was obtained by the method described herein and the reaction scheme shown in FIG. 4A and/or FIG. 4B. Compound 1 has a molecular weight of 457.50 Da.

Step 1. 2H,3H-[1,4]dioxino[2,3-b]pyridine-7-sulfonyl chloride (3)

Into a 100 mL round-bottom flask purged and maintained with an inert atmosphere of nitrogen was placed a solution of n-BuLi in hexane (2.5 M, 2 mL, 5.0 mmol, 0.54 equiv) and a solution of n-Bu$_2$Mg in heptanes (1.0 M, 4.8 mL, 4.8 mmol, 0.53 equiv). The resulting solution was stirred for 10 min at RT (20° C.). This was followed by the dropwise addition of a solution of 7-bromo-2H,3H-[1,4]dioxino[2,3-b]pyridine (2 g, 9.26 mmol, 1.00 equiv) in tetrahydrofuran (16 mL) with stirring at −10° C. in 10 min. The resulting mixture was stirred for 1 h at −10° C. The reaction mixture was slowly added to a solution of sulfuryl chloride (16 mL) at −10° C. The resulting mixture was stirred for 0.5 h at −10° C. The reaction was then quenched by the careful addition of 30 mL of saturated ammonium chloride solution at 0° C. The resulting mixture was extracted with 3×50 mL of dichloromethane. The organic layers were combined, dried over anhydrous sodium sulfate, filtered and concentrated under vacuum. The residue was purified by silica gel column chromatography, eluting with ethyl acetate/petroleum ether (1:3). This provided 1.3 g (60%) of 2H,3H-[1,4]dioxino[2,3-b]pyridine-7-sulfonyl chloride as a white solid. LCMS m/z: calculated for $C_7H_6ClNO_4S$: 235.64; found: 236 $[M+H]^+$.

Step 2. tert-Butyl 5-[2H,3H-[1,4]dioxino[2,3-b]pyridine-7-sulfonyl]-1H,2H,3H,4H,5H,6H-pyrrolo[3,4-c]pyrrole-2-carboxylate (4)

Into a 100-mL round-bottom flask was placed 2H,3H-[1,4]dioxino[2,3-b]pyridine-7-sulfonyl chloride (1.3 g, 5.52 mmol, 1.00 equiv), tert-butyl 1H,2H,3H,4H,5H,6H-pyrrolo[3,4-c]pyrrole-2-carboxylate (1.16 g, 5.52 mmol), dichloromethane (40 mL), and triethylamine (1.39 g, 13.74 mmol, 2.49 equiv). The solution was stirred for 2 h at 20° C., then diluted with 40 mL of water. The resulting mixture was extracted with 3×30 mL of dichloromethane. The organic layers were combined, dried over anhydrous sodium sulfate, filtered and concentrated under vacuum. The residue was purified by silica gel column chromatography, eluting with dichloromethane/methanol (10:1). This provided 1.2 g (53%) of tert-butyl 5-[2H,3H-[1,4]dioxino[2,3-b]pyridine-7-sulfonyl]-1H,2H,3H,4H,5H,6H-pyrrolo[3,4-c]pyrrole-2-carboxylate as a yellow solid. LCMS m/z: calculated for $C_{18}H_{23}N_3O_6S$: 409.46; found: 410 $[M+H]^+$.

Step 3. 2-[2H,3H-[1,4]dioxino[2,3-b]pyridine-7-sulfonyl]-1H,2H,3H,4H,5H,6H-pyrrolo[3,4-c]pyrrole (5)

Into a 100-mL round-bottom flask was placed tert-butyl 5-[2H,3H-[1,4]dioxino[2,3-b]pyridine-7-sulfonyl]-1H,2H,3H,4H,5H,6H-pyrrolo[3,4-c]pyrrole-2-carboxylate (1.2 g, 2.93 mmol, 1.00 equiv), dichloromethane (30 mL), and trifluoroacetic acid (6 mL). The solution was stirred for 1 h at 20° C. The resulting mixture was concentrated under vacuum. The residue was dissolved in 10 mL of methanol and the pH was adjusted to 8 with sodium bicarbonate (2 mol/L). The resulting solution was extracted with 3×10 mL of dichloromethane. The organic layers were combined, dried over anhydrous sodium sulfate, filtered and concentrated under vacuum. The crude product was purified by silica gel column chromatography, eluting with dichloromethane/methanol (10:1). This provided 650 mg (72%) of 2-[2H,3H-[1,4]dioxino[2,3-b]pyridine-7-sulfonyl]-1H,2H,3H,4H,5H,6H-pyrrolo[3,4-c]pyrrole as a yellow solid. LCMS m/z: calculated for $C_{13}H_{15}N_3O_4S$: 309.34; found: 310 [M+H]$^+$.

Step 4. (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (1) and (R)-1-(5-[2H, 3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (2)

Into a 100 mL round-bottom flask was placed 2-[2H,3H-[1,4]dioxino[2,3-b]pyridine-7-sulfonyl]-1H,2H,3H,4H,5H,6H-pyrrolo[3,4-c]pyrrole (150 mg, 0.48 mmol, 1.00 equiv), 3-hydroxy-2-phenylpropanoic acid (97 mg, 0.58 mmol, 1.20 equiv), dichloromethane (10 mL), HATU (369 mg, 0.97 mmol, 2.00 equiv) and DIEA (188 mg, 1.46 mmol, 3.00 equiv). The resulting solution was stirred overnight at 20° C. The reaction mixture was diluted with 20 mL of water and was then extracted with 3×20 mL of dichloromethane. The organic layers were combined, dried over anhydrous sodium sulfate and concentrated under vacuum. The residue was purified by prep-TLC eluted with dichloromethane/methanol (20:1) and further purified by prep-HPLC (Column: XBridge C18 OBD Prep Column, 100 Å, 5 µm, 19 mm×250 mm; Mobile Phase A: water (10 mmol/L NH$_4$HCO$_3$), Mobile Phase B: MeCN; Gradient: 15% B to 45% B over 8 min; Flow rate: 20 mL/min; UV Detector: 254 nm). The two enantiomers were separated by prep-Chiral HPLC (Column, Daicel CHIRALPAK® IF, 2.0 cm×25 cm, 5 m; mobile phase A: DCM, phase B: MeOH (hold 60% MeOH over 15 min); Flow rate: 16 mL/min; Detector, UV 254 & 220 nm). This resulted in peak 1 (2, Rt: 8.47 min) 9.0 mg (4%) of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as a yellow solid; and peak 2 (1, Rt: 11.83 min) 10.6 mg (5%) of (S)-1-(5-[2H, 3H-[1,4]dioxino[2,3-b]pyridine-7-sulfonyl]-1H,2H,3H,4H, 5H,6H-pyrrolo[3,4-c]pyrrol-2-yl)-3-hydroxy-2-phenylpropan-1-one as a yellow solid.

(1): $^1$H NMR (400 MHz, DMSO-d$_6$) δ 8.13 (d, J=2.0 Hz, 1H), 7.61 (d, J=2.0 Hz, 1H), 7.31-7.20 (m, 5H), 4.75 (t, J=5.2 Hz, 1H), 4.50-4.47 (m, 2H), 4.40-4.36 (m, 1H), 4.32-4.29 (m, 2H), 4.11-3.87 (m, 8H), 3.80-3.77 (m, 1H), 3.44-3.41 (m, 1H). LC-MS (ESI) m/z: calculated for $C_{22}H_{23}N_3O_6S$: 457.13; found: 458.0 [M+H]$^+$.

(2): $^1$H NMR (400 MHz, DMSO-d$_6$) δ 8.13 (d, J=2.0 Hz, 1H), 7.60 (d, J=2.0 Hz, 1H), 7.31-7.18 (m, 5H), 4.75 (t, J=5.2 Hz, 1H), 4.52-4.45 (m, 2H), 4.40-4.36 (m, 1H), 4.34-4.26 (m, 2H), 4.11-3.87 (m, 8H), 3.80-3.78 (m, 1H), 3.44-3.43 (m, 1H). LC-MS (ESI) m/z: calculated for $C_{22}H_{23}N_3O_6S$: 457.13; found: 458.0 [M+H]$^+$.

Step 5. (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (1)

Alternatively, Compound 1 can be synthesized using the procedure described here as Step 5. A solution of 7-((3,4,5,6-tetrahydropyrrolo[3,4-c]pyrrol-2(1H)-yl)sulfonyl)-2,3-dihydro-[1,4]dioxino[2,3-b]pyridine (130.9 mg, 0.423 mmol) in DMF (2.5 ml) was cooled on an ice bath, then treated with (S)-3-hydroxy-2-phenylpropanoic acid (84.8 mg, 0.510 mmol), HATU (195.5 mg, 0.514 mmol), and DIEA (0.30 mL, 1.718 mmol) and stirred at ambient temperature overnight. The solution was diluted with EtOAc (20 mL), washed sequentially with water (20 mL) and brine (2×20 mL), dried (MgSO$_4$), filtered, treated with silica gel, and evaporated under reduced pressure. The material was chromatographed by Biotage MPLC (10 g silica gel column, 0 to 5% MeOH in DCM) to provide a white, slightly sticky solid. The sample was readsorbed onto silica gel and chromatographed (10 g silica gel column, 0 to 100% EtOAc in hexanes) to provide (2S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (106.5 mg, 0.233 mmol, 55% yield) as a white solid.

Example 2: Biochemical Assay for Identification of PKR Activating Activity

PKR Activating Compounds can be identified with the biochemical Luminescence Assay of Example 2. The PKR activating activity of a series of chemical compounds was evaluated using the Luminescence Assay below, including compounds designated Compound 1, Compound 2, and Compounds 6, 7, and 8 below, and the compounds listed in FIG. 1.

For each tested compound, the ability to activate PKR was determined using the following Luminescence Assay. The effect of phosphorylation of adenosine-5'-diphosphate (ADP) by PKR is determined by the Kinase Glo Plus Assay (Promega) in the presence or absence of FBP (D-fructose-1,6-diphosphate; BOC Sciences, CAS: 81028-91-3) as follows. Unless otherwise indicated, all reagents are purchased from Sigma-Aldrich. All reagents are prepared in buffer containing 50 mM Tris-HCl, 100 mM KCl, 5 mM MgCl$_2$, and 0.01% Triton X100, 0.03% BSA, and 1 mM DTT. Enzyme and PEP (phosphoenolpyruvate) are added at 2× to all wells of an assay-ready plate containing serial dilutions of test compounds or DMSO vehicle. Final enzyme concentrations for PKR(wt), PKR(R510Q), and PKR(G332S) are 0.8 nM, 0.8 nM, and 10 nM respectively. Final PEP concentration is 100 µM. The Enzyme/PEP mixture is incubated with compounds for 30 minutes at RT before the assay is initiated with the addition of 2×ADP and KinaseGloPlus. Final concentration of ADP is 100 µM. Final concentration of KinaseGloPlus is 12.5%. For assays containing FBP, that reagent is added at 30 µM upon reaction initiation. Reactions are allowed to progress for 45 minutes at RT until luminescence is recorded by the BMG PHERAstar FS Multilabel Reader. The compound is tested in triplicate at concentrations ranging from 42.5 µM to 2.2 nM in 0.83% DMSO. AC$_{50}$ measurements were obtained by the standard four parameter fit algorithm of ActivityBase XE Runner (max, min, slope and AC$_{50}$). The AC$_{50}$ value for a compound is the concentration (µM) at which the activity along the four parameter logistic curve fit is halfway between minimum and maximum activity.

As set forth in Tables 2 and 3 below and in FIG. 1, AC$_{50}$ values are defined as follows: ≤0.1 µM (+++); >0.1 µM and ≤1.0 µM (++); >1.0 µM and ≤40 µM (+); >40 µM (0).

TABLE 2

Luminescence Assay Data

| Compound | AC$_{50}$ (PKRG332S) | AC$_{50}$ (PKRR510Q) | AC$_{50}$ (WT) |
|---|---|---|---|
| 1 | ++ | +++ | +++ |
| 2 | + | + | + |

TABLE 3

Additional Luminescence Assay Data

| Compound | Structure | AC$_{50}$ (PKRG332S) | AC$_{50}$ (PKRR510Q) |
|---|---|---|---|
| 6 | [structure] | ++ | + |
| 7 | [structure] | 0 | 0 |
| 8 | [structure] | 0 | 0 |

Compounds and compositions described herein are activators of wild type PKR and certain PKR mutants having lower activities compared to the wild type. Such mutations in PKR can affect enzyme activity (catalytic efficiency), regulatory properties, and/or thermostability of the enzyme. One example of a PKR mutation is G332S. Another example of a PKR mutation is R510Q.

Example 3: Enzyme Assays of a PKR Activating Compound

Figure 5:
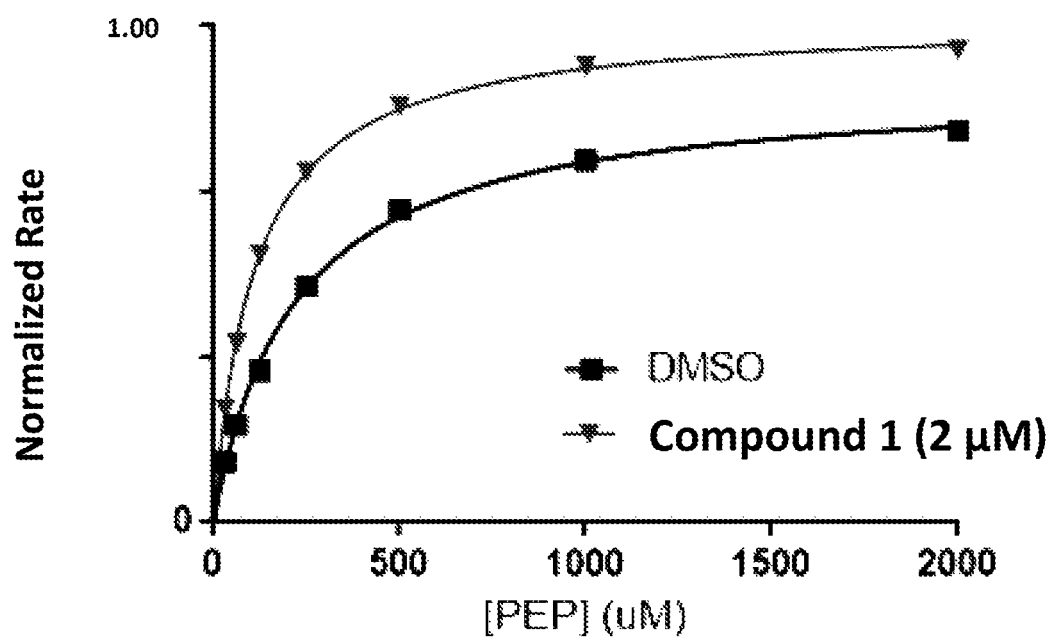
FIG. 5 is a graph showing activation of recombinant PKR-R510Q with Compound 1, plotting the normalized rate vs. concentration of phosphoenolpyruvate (PEP) (Example 3).

The effect of 2 μM Compound 1 on maximum velocity ($V_{max}$) and PEP $K_m$ (Michaelis-Menten constant, i.e., the concentration of PEP at which $v=\frac{1}{2}v_{max}$) was evaluated for wt-PKR and PKR-R510Q. Tests were conducted in the presence and absence of fructose-1,6-bisphosphate (FBP), a known allosteric activator of PKR. Assessments were made up to 60 min at RT, and $V_{max}$ and PEP $K_m$ were calculated. The effect of Compound 1 on $V_{max}$ ranged from no effect to a modest increase (see FIG. 5 for a representative curve). Compound 1 consistently reduced the PEP $K_m$, typically by ~2 fold, for wt-PKR and PKR-R510Q in the presence or absence of FBP (Table 4), demonstrating that Compound 1 can enhance the rate of PKR at physiological concentrations of PEP.

TABLE 4

Effect of Compound 1 on PKR Enzyme Kinetic Parameters

| | | No FBP | | 30 μM FBP | |
|---|---|---|---|---|---|
| Enzyme | Kinetic Parameter[a] | DMSO | 2 μM Compound 1 | DMSO | 2 μM Compound 1 |
| WT-PKR | $V_{max}$ | 1.00 | 1.14 | 1.19 | 1.16 |
| | PEP $K_m$ | 4.84 | 2.44 | 1.98 | 1.00 |
| PKR R510Q | $V_{max}$ | 1.54 | 1.56 | 1.00 | 1.29 |
| | PEP $K_m$ | 6.20 | 1.70 | 2.01 | 1.00 |

[a]All values in Table 4 are normalized to 1.00, relative to the other values in the same row.

Figure 6:
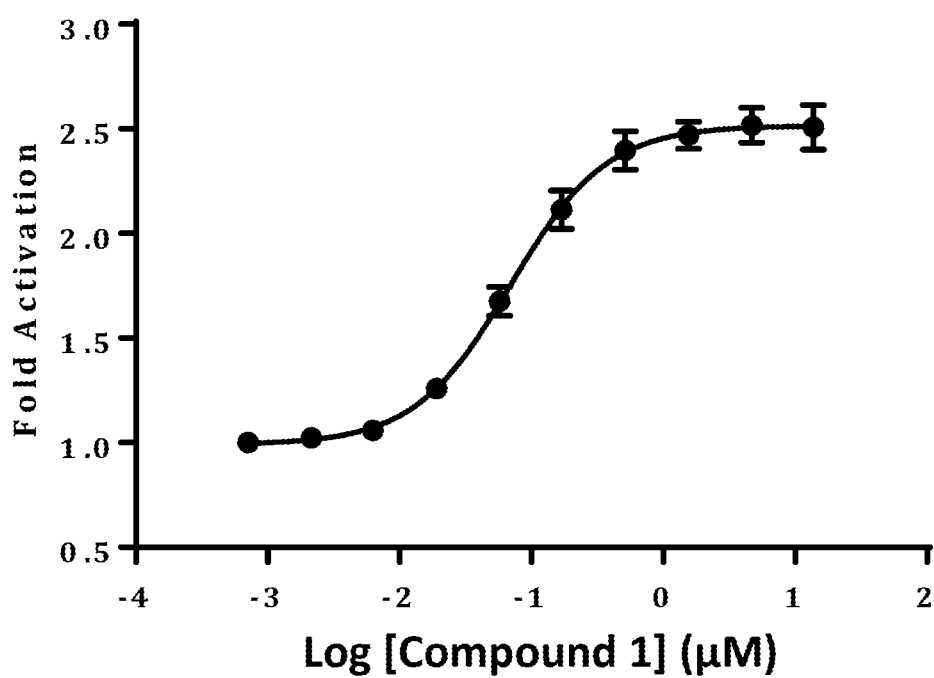
FIG. 6 is a graph of data showing activation of recombinant PKR-R510Q by Compound 1 in the enzyme assay of Example 3.

Activation of wt-PKR and PKR-R510Q by different concentrations of Compound 1 was evaluated for PEP concentrations at or below $K_m$. Compound 1 increased the rate of ATP formation, with AC$_{50}$ values ranging from <0.05 to <0.10 μM and a range of <2.0 to <3.0 maximum-fold activation (ie, <200% to <300%) (Table 5). Representative data from PKR-R510Q showed that the effect was concentration dependent (FIG. 6).

TABLE 5

Activation of PKR Wild and Mutant Types by Compound 1

| PK Enzyme | Maximum-fold Activation | $AC_{50}$ (μM) |
| --- | --- | --- |
| WT-PKR | <2.0 | <0.05 |
| PKR R510Q | <3.0 | <0.10 |

Example 4: Cell Assays of a PKR Activating Compound

Figure 7:
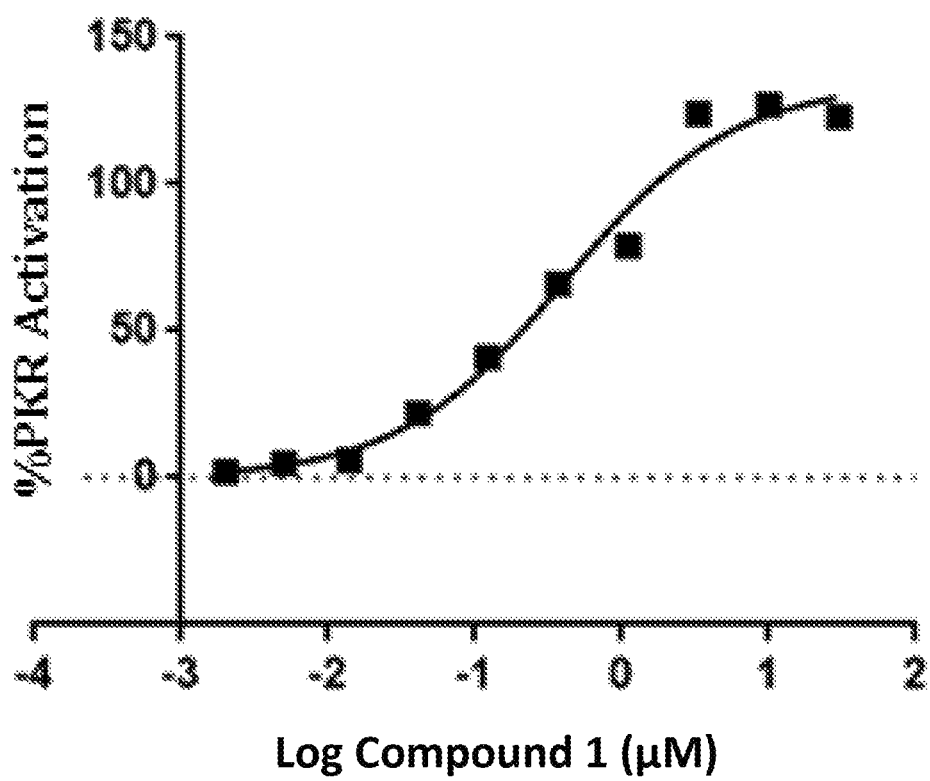
FIG. 7 is a graph of data showing PKR activation in human red blood cells treated with Compound 1 (Example 4).

The activation of wt-PKR by Compound 1 in mature human erythrocytes ex vivo was evaluated in purified RBCs purchased from Research Blood Components. Cells treated with Compound 1 for 3 hr in glucose-containing media were washed, lysed, and assayed using a Biovision Pyruvate Kinase Assay (K709-100). The assay was repeated multiple times to account for donor-to-donor variability and the relatively narrow dynamic range. Mean maximum activation increase (Max–Min) was <100% and mean 50% effective concentration ($EC_{50}$) was <125 nM (Table 6). wt-PKR was activated in a concentration-dependent manner (FIG. 7).

TABLE 6

Wild Type PKR Activation in Human Red Blood Cells Treated with Compound 1

| Replicate | Max – Min (%) | $EC_{50}$ (nM) |
| --- | --- | --- |
| 1 | <125 | <250 |
| 2 | <150 | <150 |
| 3 | <100 | <50 |
| 4 | <50 | <50 |
| Mean | <100 | <125 |

Mouse RBCs were isolated fresh from whole blood using a Ficoll gradient and assayed with methods similar to those used in the human RBCs assays. Maximum activation increase, and $EC_{50}$ values were comparable to the effects in human RBCs (Table 7).

TABLE 7

Effect of Compound 1 on PKR Activation in Mouse Red Blood Cells

| Replicate | Max – Min (%) | $EC_{50}$ (nM) |
| --- | --- | --- |
| 1 | <50 | <125 |
| 2 | <100 | <125 |
| Mean | <100 | <125 |

Example 5: Ex Vivo Pharmacology of a PKR Activating Compound

Red blood cells from SCD patients were used to evaluate the effects of Compound 1 on Hgb affinity for oxygen (i.e., oxygen affinity) and sickling under hypoxic conditions. Cells were incubated at 37° C. for 1, 2, and 3 hr with HEPES buffered saline (HBS) (untreated), HBS+dimethyl sulfoxide (DMSO) (vehicle), or 10 μM Compound 1. To assess oxygen dissociation, Hgb oxygen equilibrium curves were collected during deoxygenation.

Figure 8A:
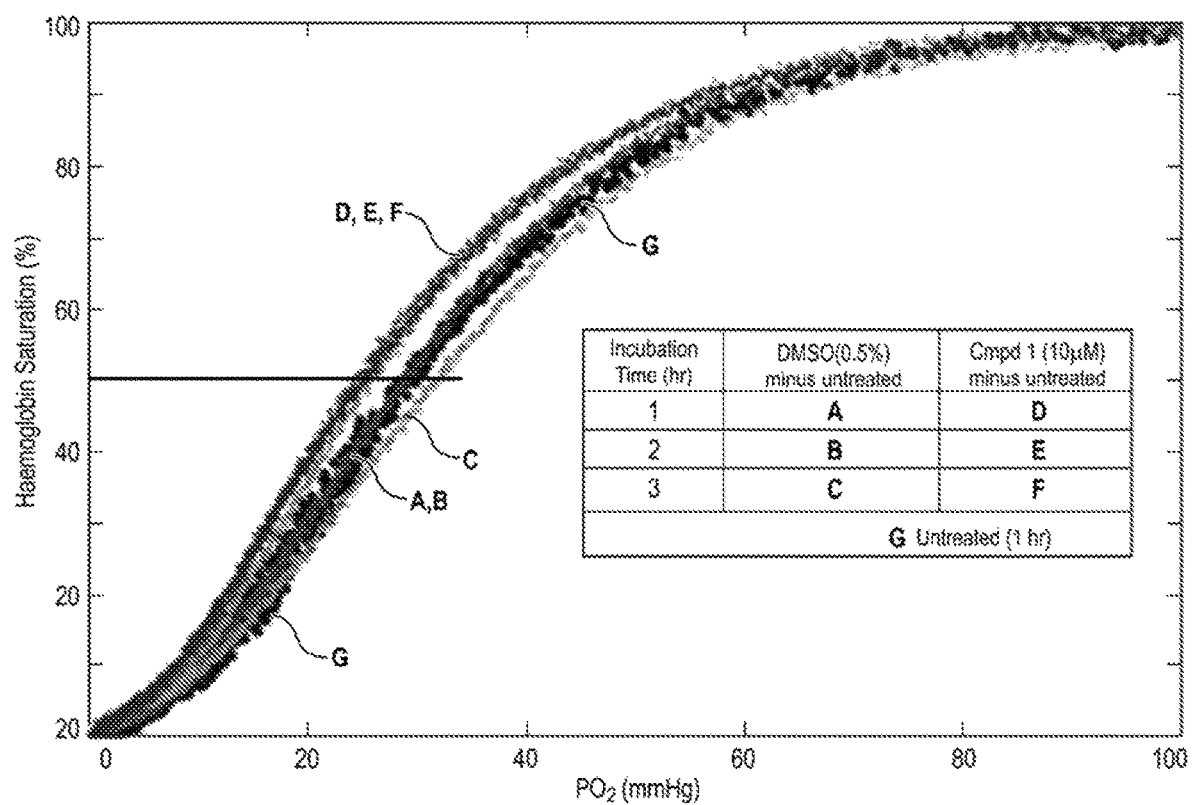
FIGS. 8A and 8B are graphs of data showing the effect of treatment with Compound 1 on oxyhemoglobin dissociation in RBCs from SCD patients (Example 5).
Figure 8B:
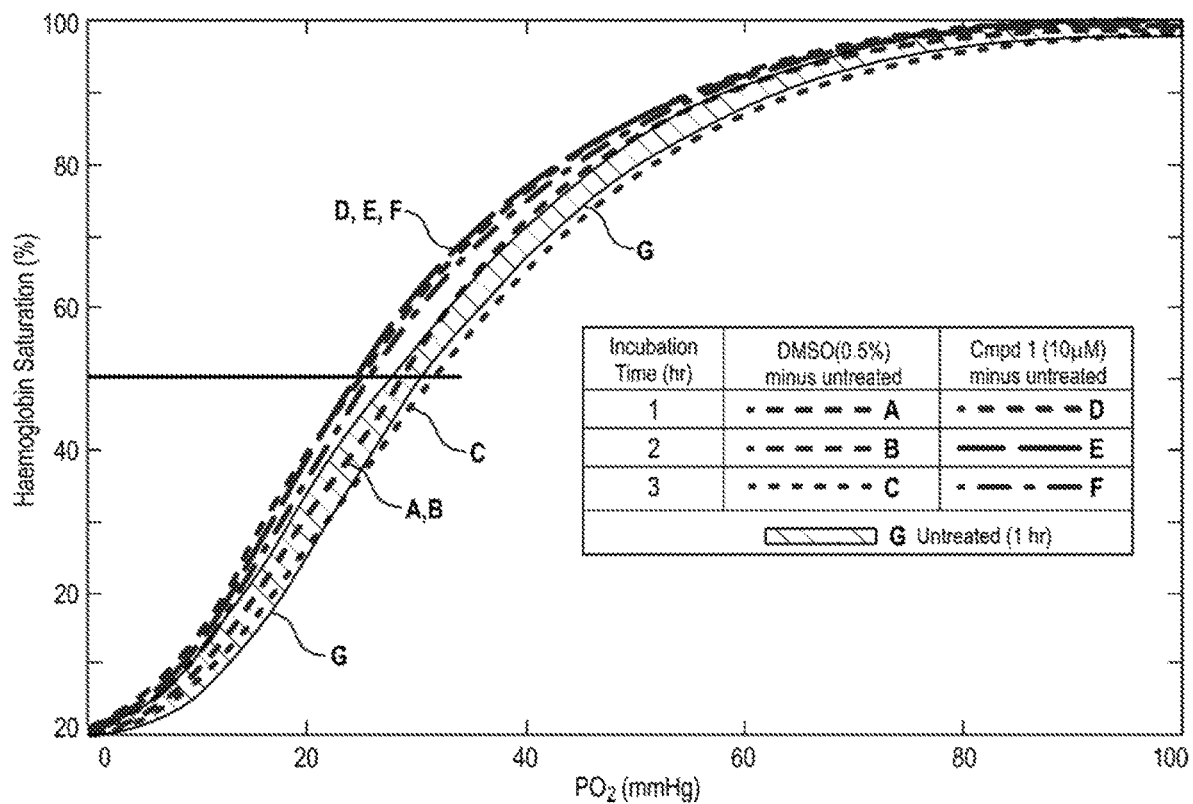

Hemoglobin saturation was shifted to the left in cells treated with Compound 1 and not in untreated or 0.5% DMSO-treated cells (FIGS. 8A and 8B). The increased oxygen affinity corresponded to a significant (but limited) shift in P50 from 29 to 25 mmHg after 1 hr that was maintained until at least 3 hr, the last time point evaluated (Table 8). Notably, oxygen affinity in the first 2 hr of incubation was not affected by DMSO.

TABLE 8

Effect of Compound 1 on Hemoglobin Saturation[a]

| | Hemoglobin Saturation | | |
| --- | --- | --- | --- |
| Incubation Time (hr) | Untreated[a] | DMSO (0.5%) | Compound 1 (10 μM) |
| 1 | 1.18 | 1.18 | 1.05 |
| 2 | | 1.18 | 1.00 |
| 3 | | 1.30 | 1.02 |

[a]All values in Table 8 are normalized to 1.00, relative to the other values.
[b]Untreated cells are washed RBCs at 40% hematocrit in media without incubation.

Figure 9:
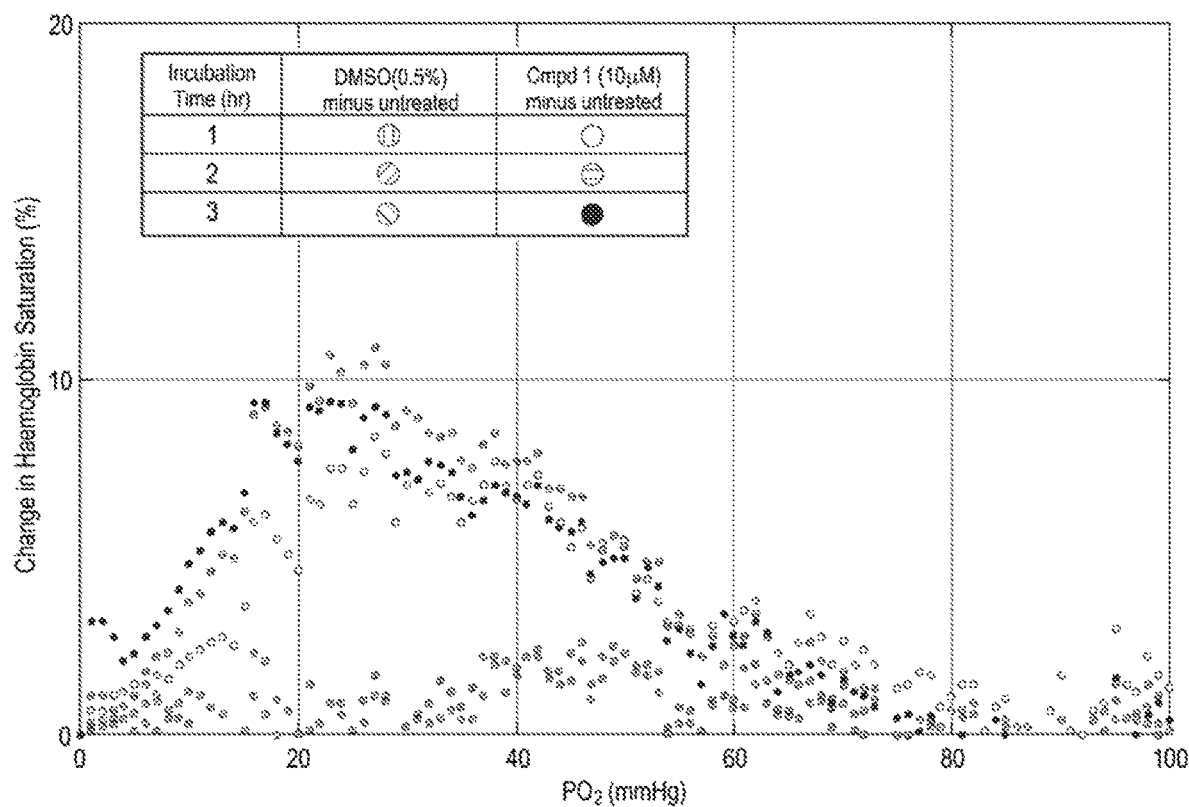
FIG. 9 is a graph of data showing delta curves of hemoglobin saturation at different oxygen tensions for red blood cells from SCD patients (Example 5). The measurement intervals are 1 mmHg.

At each $PO_2$, the average shift in Hgb saturation in the cells treated with Compound 1 was most pronounced around 25 mmHg, compared to a normal $PO_2$ of 26.7 mmHg (FIG. 9). Therefore, the shift in oxygen affinity occurred at oxygen tensions that are relevant for sickling. At 2 hr, Hgb saturation is approximately 10% higher compared to DMSO-treated cells. There is a clear difference between the cells treated with Compound 1 and those treated with DMSO at lower $PO_2$ (approximately 10 mmHg at 1% to 2% oxygen) even at 1 hr.

Figure 10:
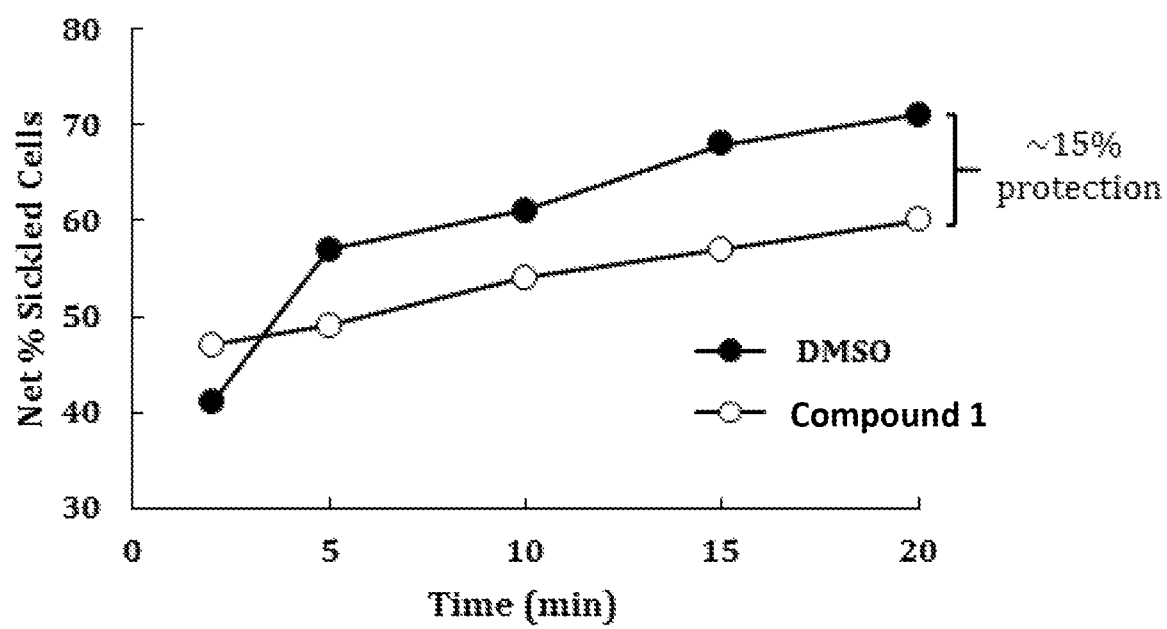
FIG. 10 is a graph of data showing an effect of Compound 1 on sickling of human SCD cells under hypoxic conditions (Example 5).

Compound 1 (10 μM) reduced cell sickling under severe hypoxic conditions of 2% oxygen ($PO_2$ of <20 mmHg) for up to 20 min (Table 9). The percent protection (i.e., the level of activity in treated cells, normalized to the level of activity in untreated cells after exposure to severe hypoxic conditions) reached a maximum of 16% at 15 min under hypoxic conditions (FIG. 10) and remained at 15% at the last time point measured.

TABLE 9

Effect of Compound 1 on Sickling of Human SCD Cells in Hypoxic Conditions

| Time in Hypoxic Conditions (min) | Net % of Sickled Cells | | % Protection |
| --- | --- | --- | --- |
| | DMSO (0.5%) | Compound 1 (10 μM) | |
| 0 | 7 | 10 | |
| 2 | 41 | 47 | −15 |
| 5 | 57 | 49 | 14 |
| 10 | 61 | 54 | 11 |
| 15 | 68 | 57 | 16 |
| 20 | 71 | 60 | 15 |

Example 6: Pharmacokinetic/Pharmacodynamic Studies of Compound 1 in Wild Type Mice Two pharmacokinetic (PK)/phamacodynamic (PD) studies were conducted in Balb/c mice that were administered Compound 1 once daily by oral gavage (formulated in 10% Cremophor EL/10% PG/80% DI water) for 7 days (QD×7) at doses of 0 (vehicle), 3.75, 7.5, 15, 30, 60 mg/kg (Study 1); 0 (vehicle), 7.5, 15, 30, 60, 120, or 240 mg/kg (Study 2). On the 7th day, whole blood was collected 24 hours after dosing and snap frozen. Samples were later thawed and analyzed by LC/MS for 2,3-DPG and ATP levels. In both studies, Compound 1 was well tolerated. No adverse clinical signs were observed and there were no differences in body weight change compared with the vehicle group.

Figure 11A:
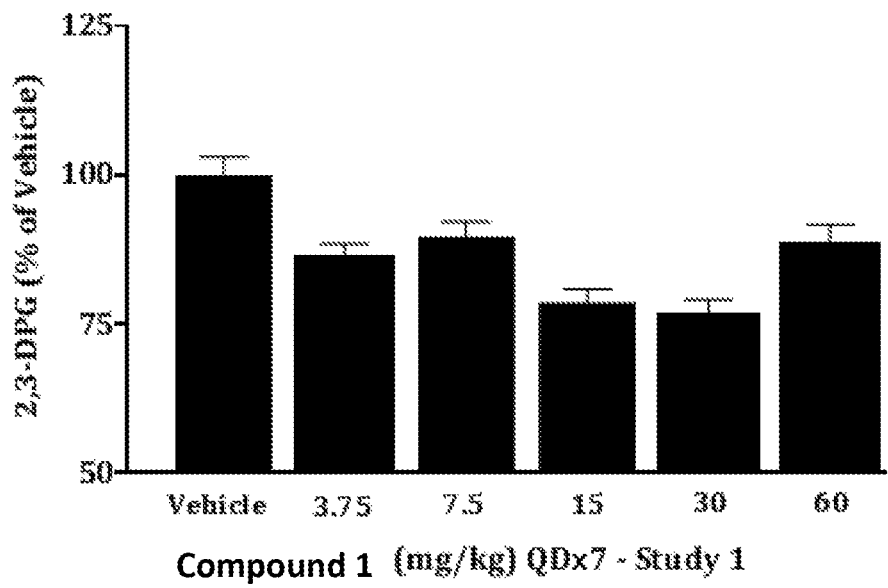
FIG. 11A (Study 1) and FIG. 11B (Study 2) are each graphs showing the observed changes in 2,3-DPG levels in blood from mice following 7 days of once daily (QD) oral treatment with Compound 1 (Example 6).
Figure 11B:
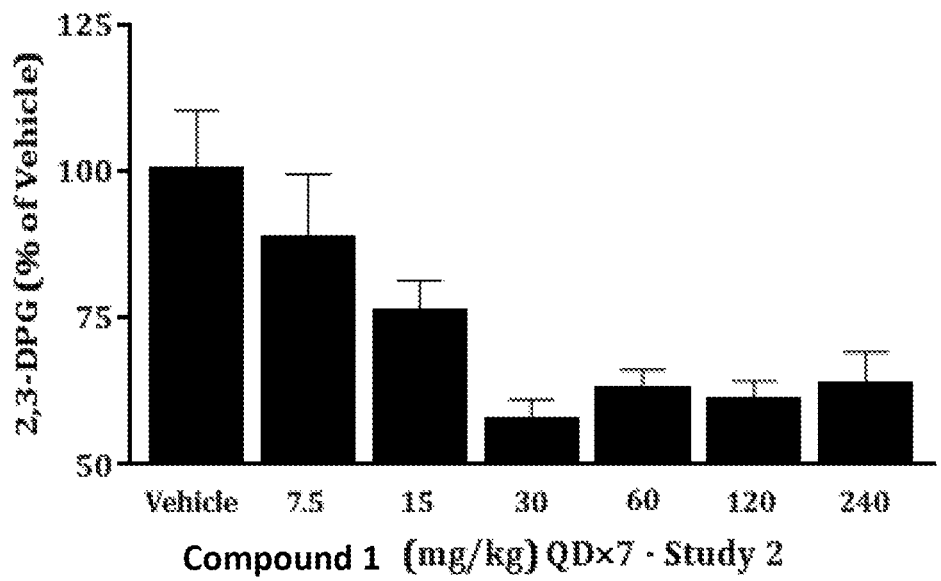
Figure 12:
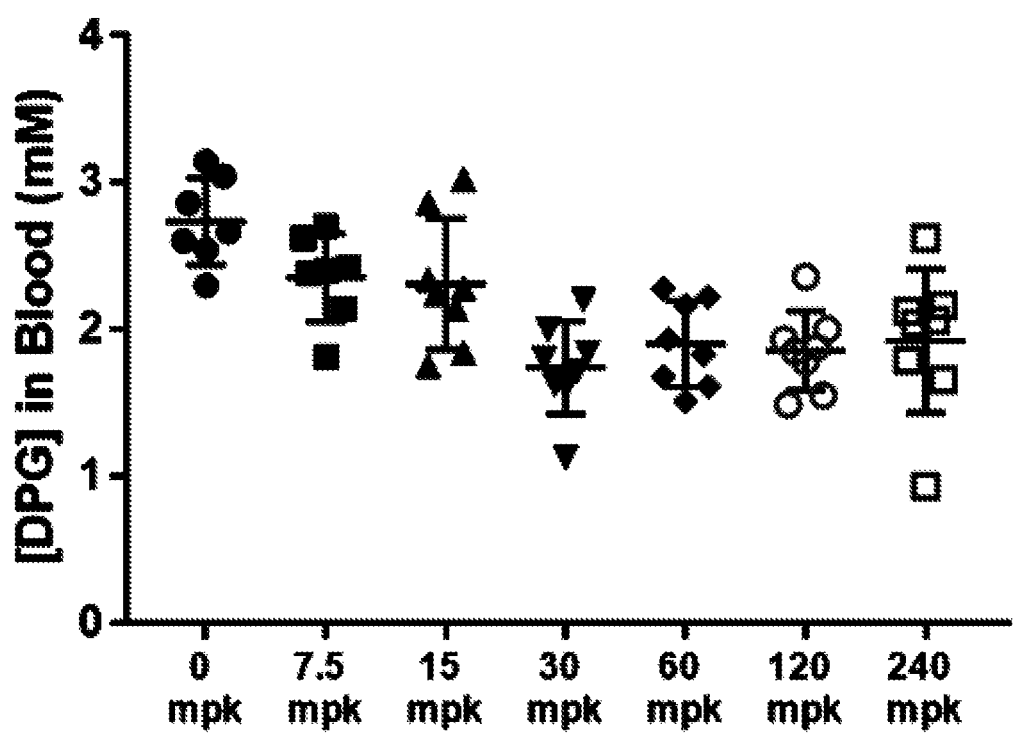
FIG. 12 is a graph showing observed changes in 2,3-DPG levels in blood from mice following 7 days of once daily (QD) oral treatment with Compound 1 (Example 6, Study 2).

The levels of 2,3-DPG decreased with Compound 1 treatment (FIGS. 11A and 11B (Studies 1 and 2) and FIG. 12 (Study 2)). In general, reductions were >20% at ≥15 mg/kg Compound 1, and >30% for 120 and 240 mg/kg Compound 1. Together, the results from the highest doses provide in vivo evidence that 2,3-DPG decreases with PKR activation.

Figure 13A:
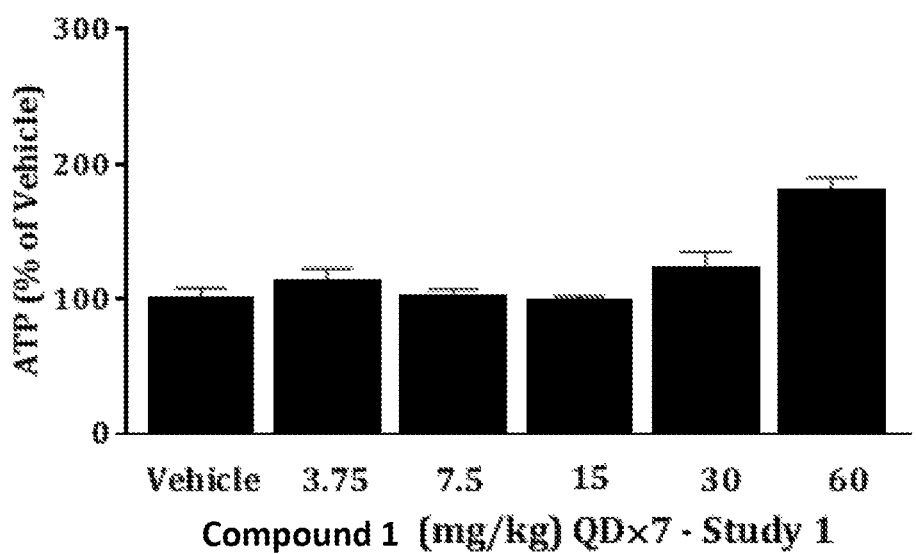
FIG. 13A (Study 1) and FIG. 13B (Study 2) are graphs of data measuring ATP concentrations in red blood cells of mice following 7 days of once daily (QD) oral treatment with Compound 1 (Example 6).
Figure 13B:
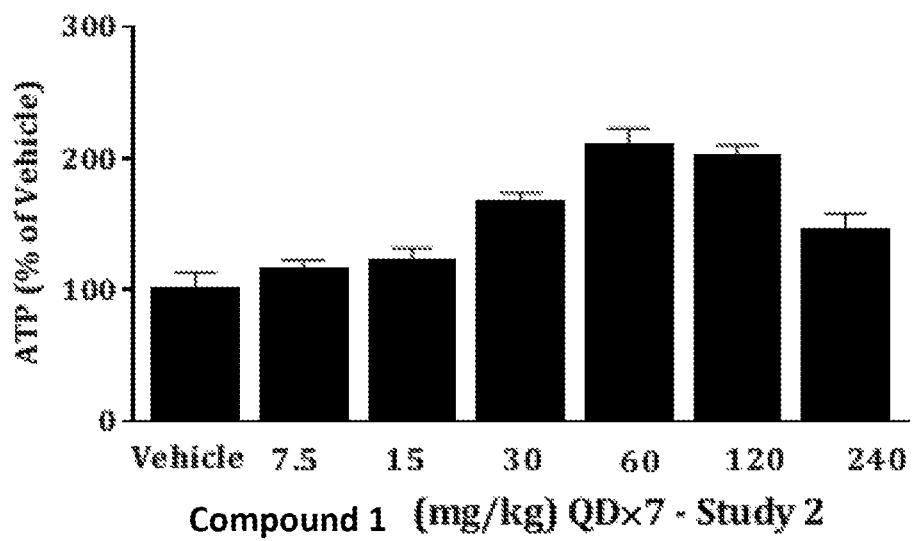
Figure 14A:
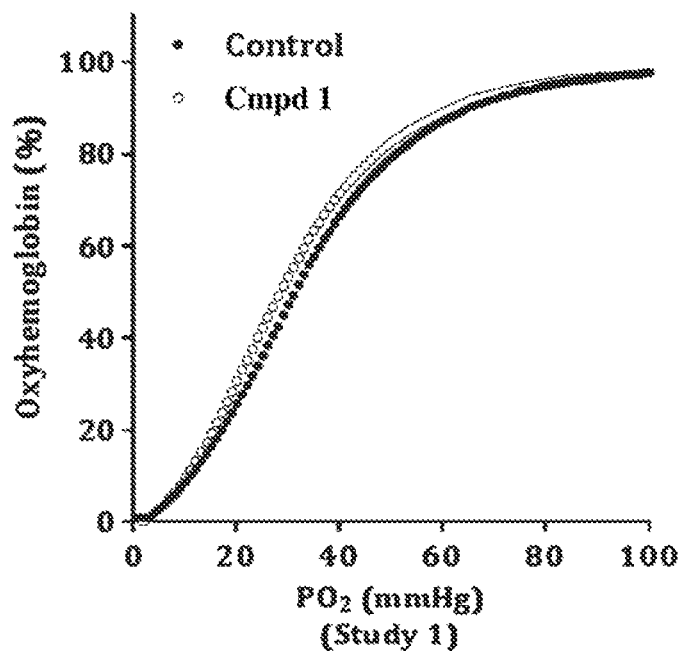
FIG. 14A and FIG. 14B are each a graph of data showing oxygen saturation in RBCs following 7 days of oral treatment with Compound 1 in a murine model of SCD (Example 7).
Figure 14B:
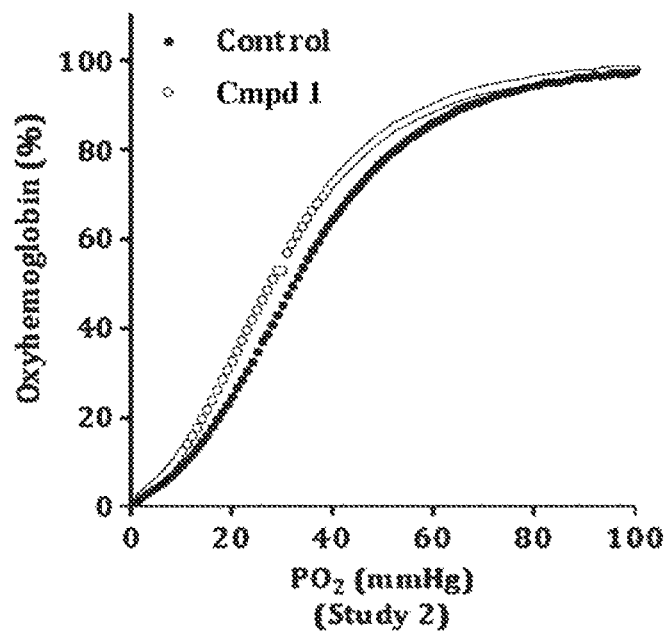
Figure 15A:
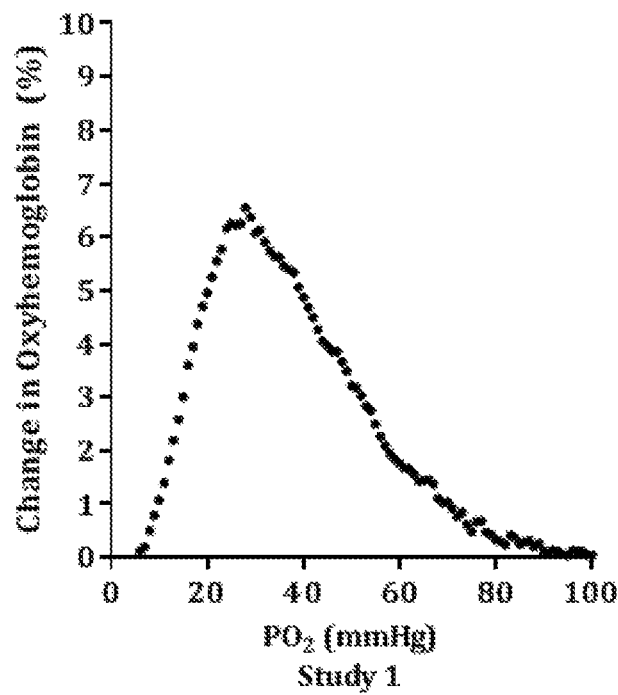
FIG. 15A and FIG. 15B are each a graph of data showing change in oxygen saturation in RBCs following 7 days of oral treatment with Compound 1 in a murine model of SCD (Example 7).
Figure 15B:
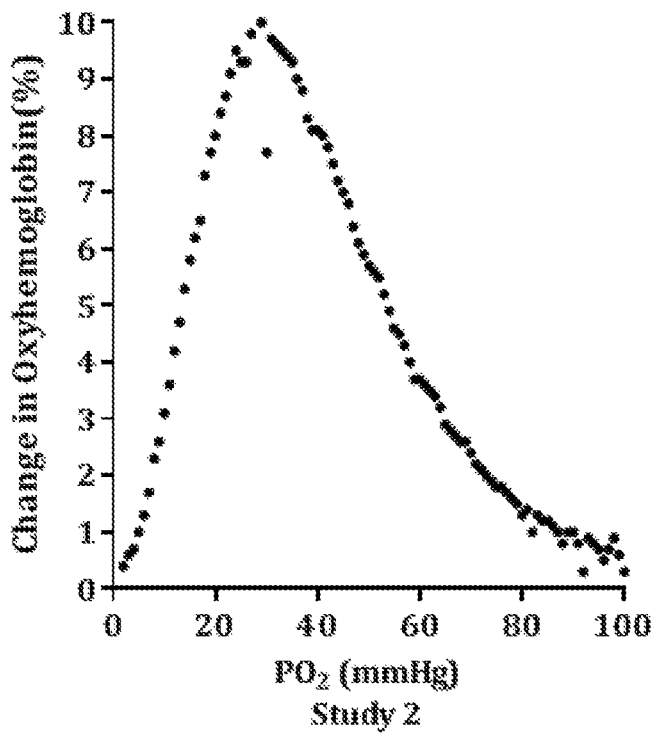

Evaluation of ATP levels in these studies showed that treatment with Compound 1 increased levels of ATP. In Study 1, ATP increased 21% and 79% with 30 and 60 mg/kg Compound 1, respectively, compared to vehicle, and in Study 2, ATP levels increased with exposure with doses up to 120 mg/kg Compound 1 with a maximum increase of ~110% compared to vehicle (FIG. 13A and FIG. 13B). At the highest dose, 240 mg/kg Compound 1, ATP levels increased by 45%. Levels of ATP correlated with Compound 1 exposure in a manner similar across both studies.

Example 7: Testing a PKR Activating Compound in a Berkeley SS Mouse Model

Targeted gene deletions and a human transgene in the Berkeley SS mouse model result in mice that express human HgbS almost exclusively (Pászty C. Transgenic and gene knock-out mouse models of sickle cell anemia and the thalassemias. Curr Opin Hematol. 1997 March; 4(2):88-93) and mimic the genetic, hematologic, and histopathologic features of SCD in humans. These include irreversibly sickled RBCs, anemia, and multi-organ pathology.

The effects of Compound 1 on Hgb affinity for oxygen, percentage of sickled cells, and/or Hgb were evaluated in the Berkley SS mouse. Two studies were conducted where mice received 0 or 1000 ppm Compound 1 ad libitum in mouse chow for 7 days. Blood was drawn on Day 7 and analyzed under hypoxic conditions. Red cell parameters were measured by ADVIA.

Figure 16:
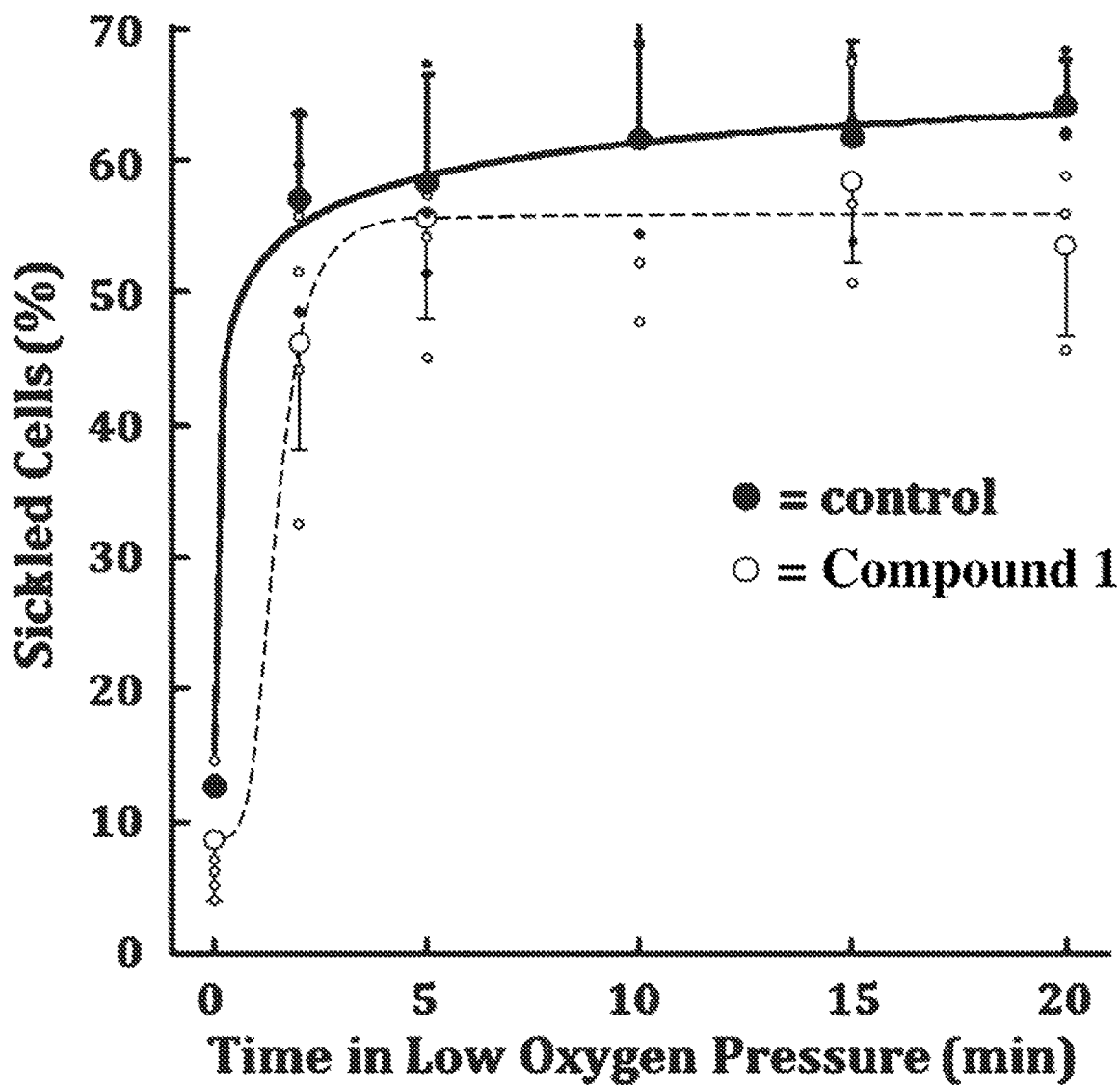
FIG. 16 is a graph of data showing the percentage of sickled cells in a murine model of SCD following 7 days of oral treatment with Compound 1 (Example 7).
Figure 17:
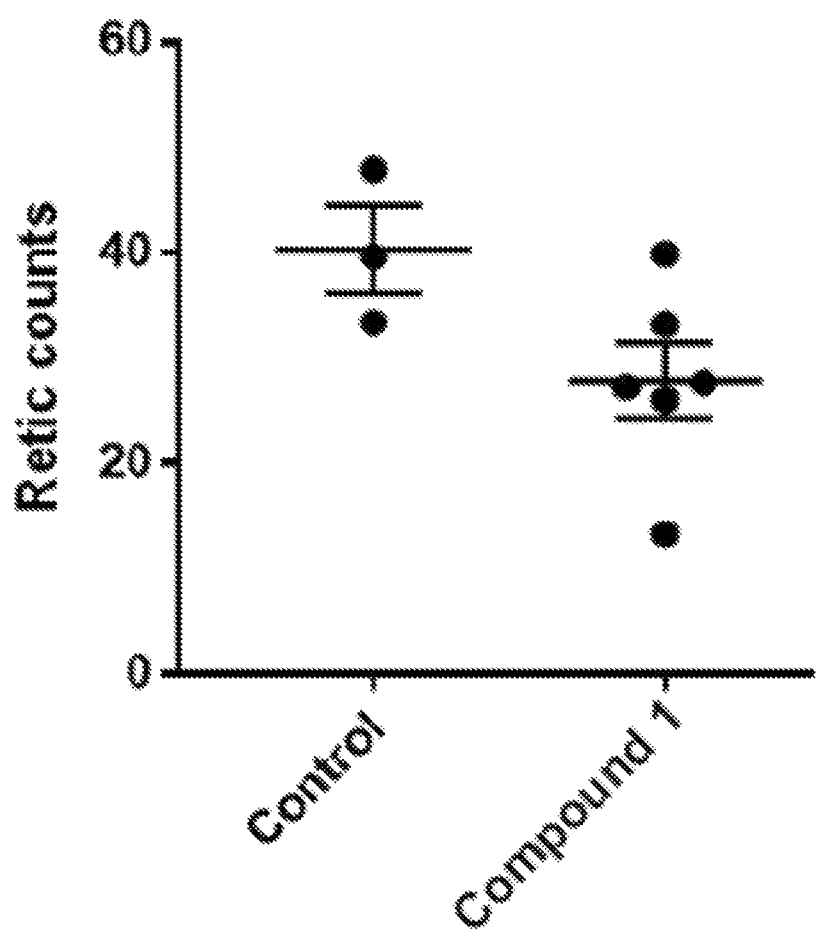
FIG. 17 is a graph of data showing the reticulocyte count in cells in a murine model of SCD following 7 days of oral treatment with Compound 1 (Example 7).

The findings were relatively consistent between the two studies. Oxygen affinity to Hgb under hypoxic conditions was increased and P50 was decreased (FIG. 14A, FIG. 14B, FIG. 15A, and FIG. 15B). A positive effect on sickling was observed such that the percentage of RBCs that sickled at low oxygen pressures was decreased (FIG. 16) and time to sickle was increased with Compound 1 treatment. Furthermore, Hgb was increased by ~1 g/dL. Together, these changes support the hypothesis that Compound 1 will reduce cell sickling and positively impact the downstream clinical complications of sickled RBCs. Compound 1 also reduced the level of reticulocytes in treated mice (FIG. 17), indicative of reduced red cell lysis.

Example 8: A SAD/MAD Study to Assess the Safety, Pharmacokinetics, and Pharmacodynamics of Compound 1 in Healthy Volunteers and Sickle Cell Disease Patients Compound 1 will be evaluated in a randomized, placebo-controlled, double blind, single ascending and multiple ascending dose study to assess the safety, pharmacokinetics, and pharmacodynamics of Compound 1 in healthy volunteers and sickle cell disease patients. The use of Compound 1 is disclosed herein for treatment of sickle cell disease in humans.

Compound 1 is an oral small-molecule agonist of pyruvate kinase red blood cell isozyme (PKR) being developed for the treatment of hemolytic anemias. This human clinical trial study will characterize the safety, tolerability and the pharmacokinetics/pharmacodynamics (PK/PD) of a single ascending dose and multiple ascending doses of Compound 1 in the context of phase 1 studies in healthy volunteers and sickle cell disease patients. The effects of food on the absorption of Compound 1 will also be evaluated, in healthy volunteers.

The objectives of the study include the following:
1. To evaluate the safety and tolerability of a single ascending dose and multiple ascending doses of Compound 1 in healthy volunteers and sickle cell disease (SCD) patients.
2. To characterize the pharmacokinetics (PK) of Compound 1.
3. To evaluate the levels of 2,3-diphosphoglycerate (DPG) and adenosine triphosphate (ATP) in the red blood cells (RBCs) of healthy volunteers and SCD patients after single and multiple doses of Compound 1.
4. To evaluate the relationship between Compound 1 plasma concentration and potential effects on the QT interval in healthy volunteers.
5. To evaluate the effect of single ascending doses of Compound 1 on other electrocardiogram (ECG) parameters (heart rate, PR and QRS interval and T-wave morphology) in healthy volunteers.
6. To explore food effects on the PK of Compound 1 in healthy volunteers.
7. To explore the association of Compound 1 exposure and response variables (such as safety, pharmacodynamics (PD), hematologic parameters as appropriate).
8. To explore effects of Compound 1 after single and multiple doses on RBC function.
9. To explore effects of Compound 1 after multiple doses in SCD patients on RBC metabolism, inflammation and coagulation.

This is a first-in-human (FIH), Phase 1 study of Compound 1 that will characterize the safety, PK, and PD of Compound 1 after a single dose and after repeated dosing first in healthy adult volunteers and then in adolescents or adults with sickle cell disease. The study arms and assigned interventions to be employed in the study are summarized in Table 10. Initially, a dose range of Compound 1 in single ascending dose (SAD) escalation cohorts will be explored in healthy subjects. Enrollment of healthy subjects into 2-week multiple ascending dose (MAD) escalation cohorts will be initiated once the safety and PK from at least two SAD cohorts is available to inform the doses for the 2-week MAD portion of the study. The MAD cohorts will then run in parallel to the single dose cohorts. A single dose cohort is planned to understand food effects (FE) on the PK of Compound 1. After the SAD and FE studies in healthy subjects are completed, the safety, PK and PD of a single dose of Compound 1 that was found to be safe in healthy subjects will then be evaluated in sickle cell disease (SCD) subjects. Multiple dose studies in SCD subjects will then be initiated upon completion of MAD studies in healthy volunteers. Compound 1 will be administered in 25 mg and 100 mg tablets delivered orally.

TABLE 10

| Arms | Assigned Interventions |
| --- | --- |
| Experimental: Single ascending dose cohorts in healthy subjects<br>Healthy volunteer subject cohorts randomized 6:2 receiving a single dose of Compound 1 or placebo. The first cohort will receive 200 mg of Compound 1 or placebo. Dose escalation will occur if Compound 1 or placebo is tolerated. The maximum dose of Compound 1 or placebo will be 1500 mg. Planned doses for the SAD cohorts are listed in Table 11. | Drug: Compound 1/Placebo<br>Healthy volunteer subjects will receive Compound 1/placebo and be monitored for side effects while undergoing pharmacokinetics and pharmacodynamic studies |
| Experimental: Multiple ascending dose cohorts in healthy subjects<br>Healthy volunteer subject cohorts randomized 9:3 to receive Compound 1 or placebo for 14 days continuous dosing. The first cohort will receive 100 mg of Compound 1 or placebo daily X 14 days. Alternatively, the first cohort will receive 200 mg (e.g., 100 mg BID or 200 mg QD) of Compound 1 or placebo daily X 14 days. The maximum dose of Compound 1/placebo will be 600 mg Compound 1/placebo daily for 14 days. Planned doses for the MAD cohorts are listed in Table 12. | Drug: Compound 1/Placebo<br>Healthy volunteer subjects will receive Compound 1/placebo and be monitored for side effects while undergoing pharmacokinetics and pharmacodynamic studies |
| Experimental: Food Effect Cohort in healthy subjects<br>Healthy Volunteer subject cohort of 10 subjects who will receive a single dose of Compound 1 with food and without food. Dose will be administered per the protocol defined dose. Healthy Volunteer subject cohort of 10 subjects who will receive a single dose of Compound 1 with food and without food. Dose will be 500 mg of Compound 1, but is subject to change based on the pharmacokinetic profile of Compound 1 observed in the initial SAD cohorts and the safety profile of Compound 1 observed in prior SAD and MAD cohorts. | Drug: Compound 1<br>Healthy subjects will receive Compound 1 with or without food and undergo pharmacokinetic studies |
| Experimental: Single ascending dose cohorts in SCD subjects<br>Sickle cell disease subject cohort randomized 6:2 receiving a single dose of Compound 1 or placebo. The dose of Compound 1/placebo administered will be a dose that was found to be safe in healthy subjects. The dose of Compound 1/placebo administered also will be a dose that was found to be pharmacodynamically active (e.g., results in a reduction in 2,3-DPG) in healthy subjects. | Drug: Compound 1/Placebo<br>SCD subjects will receive Compound 1/placebo and be monitored for side effects while undergoing pharmacokinetic and pharmacodynamics studies |
| Experimental: Multiple ascending dose cohorts in SCD subjects<br>Sickle cell disease subject cohorts randomized 9:3 to receive Compound 1 or placebo for 14 days continuous dosing. The dose of Compound 1/placebo administered will be a dose less than maximum tolerable dose evaluated in MAD healthy volunteers. The dose of Compound 1/placebo also will be a dose that was found to be pharmacodynamically active (e.g., results in a reduction in RBC 2,3-DPG and increase in RBC ATP) in MAD healthy volunteers. | Drug: Compound 1/Placebo<br>SCD subjects will receive Compound 1/placebo and be monitored for side effects while undergoing pharmacokinetic and pharmacodynamics studies |

TABLE 11

| Dose Level/Cohort | Dose | Tablet Strength (#/day) |
| --- | --- | --- |
| SAD 1 | 200 mg | 100 mg (2/day) |
| SAD 2 | 400 mg | 100 mg (4/day) |
| SAD 3 | 700 mg | 100 mg (7/day) |
| SAD 4 | 1100 mg | 100 mg (11/day) |
| SAD 5 | 1500 mg | 100 mg (15/day) |

TABLE 12

| Dose Level/Cohort | Dose | Tablet Strength (#/day) |
| --- | --- | --- |
| MAD 1 | 100 mg | 100 mg (1/day) or 25 mg (4/day) |
| MAD 2 | 200 mg | 100 mg (2/day) |
| MAD 3 | 400 mg | 100 mg (4/day) |
| MAD 4 | 600 mg | 100 mg (6/day) |

Outcome Measures

Primary Outcome Measures:

1. Incidence, frequency, and severity of adverse events (AEs) per CTCAE v5.0 of a single ascending dose and multiple ascending doses of Compound 1 in adult healthy volunteers and SCD patients.
   [Time Frame: Up to 3 weeks of monitoring]
2. Maximum observed plasma concentration (Cmax)
   [Time Frame: Up to 3 weeks of testing]
3. Time to maximum observed plasma concentration (Tmax)
   [Time Frame: Up to 3 weeks of testing]
4. Area under the plasma concentration-time curve from time zero until the 24-hour time point (AUC0-24)
   [Time Frame: Up to 3 weeks of testing]
5. Area under the plasma concentration-time curve from time zero until last quantifiable time point (AUC0-last)
   [Time Frame: Up to 3 weeks of testing]
6. Area under the plasma concentration-time curve from time zero to infinity (AUC0-inf)
   [Time Frame: Up to 3 weeks of testing]
7. Terminal elimination half-life (t½)
   [Time Frame: Up to 3 weeks of testing]
8. Apparent clearance (CL/F)
   [Time Frame: Up to 3 weeks of testing]
9. Apparent volume of distribution (Vd/F)
   [Time Frame: Up to 3 weeks of testing]
10. Terminal disposition rate constant (Lz)
    [Time Frame: Up to 3 weeks of testing]
11. Renal clearance (ClR)
    [Time Frame: Up to 3 weeks of testing]

Secondary Outcome Measures:

12. Change from baseline in the levels of 2,3-diphosphoglycerate (DPG) and adenosine triphosphate (ATP) in the red blood cells (RBCs) of healthy volunteers and SCD patients after single and multiple doses of Compound 1.
    [Time Frame: Up to 3 weeks of testing]
13. Model-based estimate of change from baseline QT interval corrected using Fridericia's correction formula (QTcF) and 90% confidence interval at the estimated Cmax after a single dose of Compound 1 in healthy volunteers.
    [Time Frame: up to 7 days]
14. Change from baseline heart rate after a single dose of Compound 1 in healthy volunteers
    [Time Frame: up to 7 days]
15. Change from baseline PR after a single dose of Compound 1 in healthy volunteers
    [Time Frame: up to 7 days]
16. Change from baseline QRS after a single dose of Compound 1 in healthy volunteers
    [Time Frame: up to 7 days]
17. Change from baseline T-wave morphology after a single dose of Compound 1 in healthy volunteers
    [Time Frame: up to 7 days]

Exploratory Outcome Measures:

18. Effect of food on $C_{max}$, $AUC_{0-24}/AUC_{last}$
19. Effect of $AUC_{last}/AUC_{0-24}$, $C_{max}$, minimum plasma concentration ($C_{min}$), peak-to trough ratio, dose linearity, accumulation ratio on safety, PD, and hematologic parameters of interest, as assessed by exposure-response analyses
20. Effect of 2,3-DPG reduction in RBCs on the oxyhemoglobin dissociation curve (P50; partial pressure of $O_2$ at which 50% of hemoglobin is saturated with $O_2$) after a single dose and after chronic dosing of Compound 1
21. Effect of chronic Compound 1 dosing on normal and SCD RBC deformability by osmotic gradient ektacytometry and oxygen gradient ektacytometry
22. Effect of chronic Compound 1 dosing on SCD RBC response to oxidative stress in SCD Patients (including evaluation of glutathione, glutathione peroxidase and superoxide dismutase levels)
23. Effect of chronic Compound 1 dosing on measurable markers of inflammation in SCD Patients (C-reactive protein, ferritin, interleukin [IL]-1β, IL-6, IL-8, and tumor necrosis factor-α)
24. Effects of chronic Compound 1 dosing on measurable markers of hypercoagulation in SCD patients (D-dimer, prothrombin 1.2, and thrombin-antithrombin [TAT] complexes)

Eligibility

Minimum age: 18 Years (healthy volunteers); 12 Years (SCD subjects)

Maximum age: 60 Years

Sex: All

Gender Based: No

Accepts Healthy Volunteers: Yes

Inclusion Criteria:

Healthy volunteer: subjects must be between 18 and 60 years of age; SCD: subjects must be between 12 and 50 years of age Subjects must have the ability to understand and sign written informed consent, which must be obtained prior to any study-related procedures being completed.

Subjects must be in general good health, based upon the results of medical history, a physical examination, vital signs, laboratory profile, and a 12-lead ECG.

Subjects must have a body mass index (BMI) within the range of 18 kg/m² to 33 kg/m² (inclusive) and a minimum body weight of 50 kg (healthy volunteer subjects) or 40 kg (SCD subjects)

For SCD subjects, sickle cell disease previously confirmed by hemoglobin electrophoresis or genotyping indicating one of the following hemoglobin genotypes: Hgb SS, Hgb Sβ⁺-thalassemia, Hgb Sβ⁰-thalassemia, or Hgb SC All males and females of child bearing potential must agree to use medically accepted contraceptive regimen during study participation and up to 90 days after.

Subjects must be willing to abide by all study requirements and restrictions.

Exclusion Criteria:

Evidence of clinically significant medical condition or other condition that might significantly interfere with the absorption, distribution, metabolism, or excretion of study drug, or place the subject at an unacceptable risk as a participant in this study History of clinically significant cardiac diseases including condition disturbances Abnormal hematologic, renal and liver function studies History of drug or alcohol abuse Results (Healthy Volunteers)

Four healthy SAD cohorts were evaluated at doses of 200, 400, 700, and 1000 mg, and four healthy MAD cohorts received 200 to 600 mg total daily doses for 14 days at QD or BID dosing (100 mg BID, 200 mg BID, 300 mg BID, and 400 mg QD). In the food effect (FE) cohort, 10 healthy subjects received 200 mg of Compound 1 QD with and without food.

No serious adverse events (SAEs) or AEs leading to withdrawal were reported in the SAD and MAD cohorts of healthy volunteers. In PK assessments, Compound 1 was rapidly absorbed with a median $T_{max}$ of 1 hr postdose. Single dose exposure increased in greater than dose-proportional manner at doses ≥700 mg. In multiple-doses delivered BID or QD, linear PK was observed across all dose levels (100-300 mg BID, 400 mg QD), and exposure remained steady up to day 14, without cumulative effect. Compound 1 exposure under fed/fasted conditions was similar.

PD activity was demonstrated at all dose levels evaluated in Compound 1-treated subjects (Table 13). Table 13 reports the mean maximum percentage change in 2,3-DPG, ATP, and P50 across all doses and timepoints in the SAD and MAD cohorts. As shown in Table 13, a mean decrease in 2,3-DPG and P50, and a mean increase in ATP, relative to baseline, was observed in both the SAD and MAD cohorts. Within 24 hr of a single dose of Compound 1, a decrease in 2,3-DPG with a corresponding increase in P50 was observed. After 14 days of Compound 1 dosing these PD effects were maintained along with an increase in ATP over baseline. Accordingly, the mean maximum reduction in the concentration of 2,3-DPG was at least about 40% in patients receiving Compound 1 in the SAD study and at least about 50% in patients receiving Compound 1 in the MAD study.

In the SAD cohorts, the subjects' blood 2,3-DPG levels were measured periodically after dosing by a qualified LC-MS/MS method for the quantitation of 2,3-DPG in blood. Decreased 2,3-DPG blood levels were observed 6 hours following a single dose of Compound 1 at all dose levels (earlier timepoints were not collected). Maximum decreases in 2,3-DPG levels generally occurred ~24 hours after the first dose with the reduction sustained ~48-72 hr postdose. Table 14 reports the median percentage change in 2,3-DPG blood levels, relative to baseline, measured over time in healthy volunteers after a single dose of Compound 1 (200 mg, 400 mg, 700 mg, or 1000 mg) or placebo. Accordingly, the median reduction in the concentration of 2,3-DPG, relative to baseline, was at least about 30% at all dose levels tested 24 hours after administration of the single dose.

TABLE 14

Median Percentage Change in 2,3-DPG Levels

| Time After Dose | Dose | | | | |
|---|---|---|---|---|---|
| | Placebo | 200 mg | 400 mg | 700 mg | 1000 mg |
| 0 | 0.0 | 0.0 | 0.0 | 0.0 | 0.0 |
| 6 | −7.8 | −18 | −23 | −29 | −20 |
| 8 | −7.6 | −17 | −29 | −28 | −31 |
| 12 | −4.0 | −25 | −40 | −41 | −44 |
| 16 | −6.0 | −33 | −35 | −46 | −50 |
| 24 | −2.0 | −31 | −39 | −49 | −48 |
| 36 | −6.9 | −33 | −38 | −46 | −47 |
| 48 | −15 | −29 | −31 | −48 | −47 |
| 72 | −6.9 | −18 | −30 | −33 | −21 |

Figure 18:
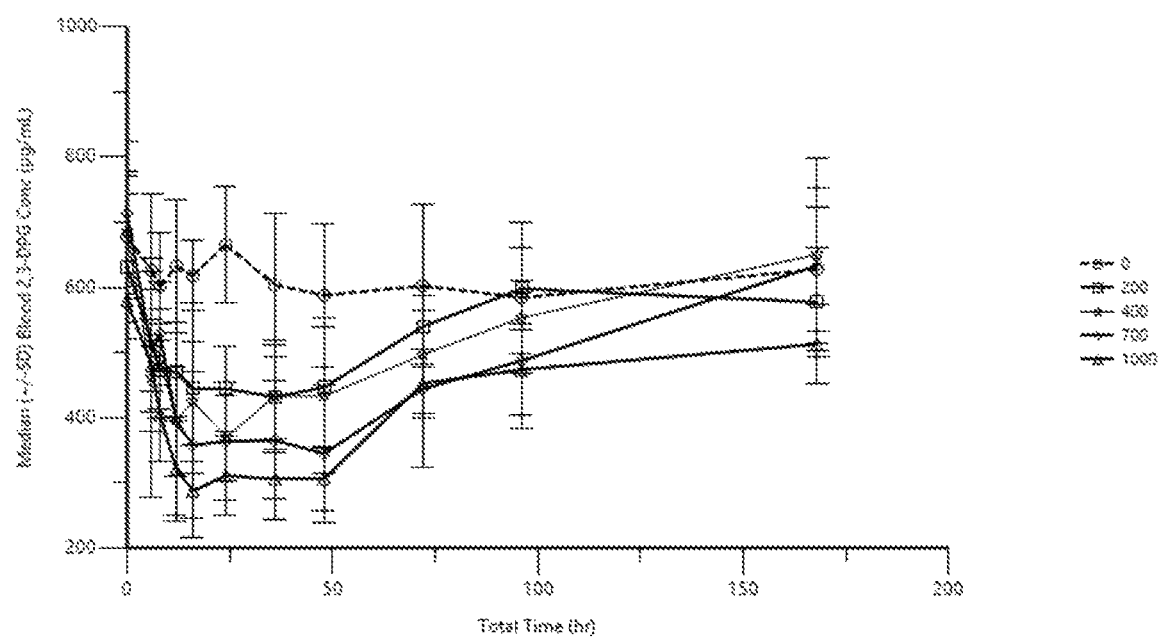
FIG. 18 is a graph of the blood 2,3-DPG levels measured over time in healthy volunteers who received a single dose of Compound 1 or placebo.
Figure 19:
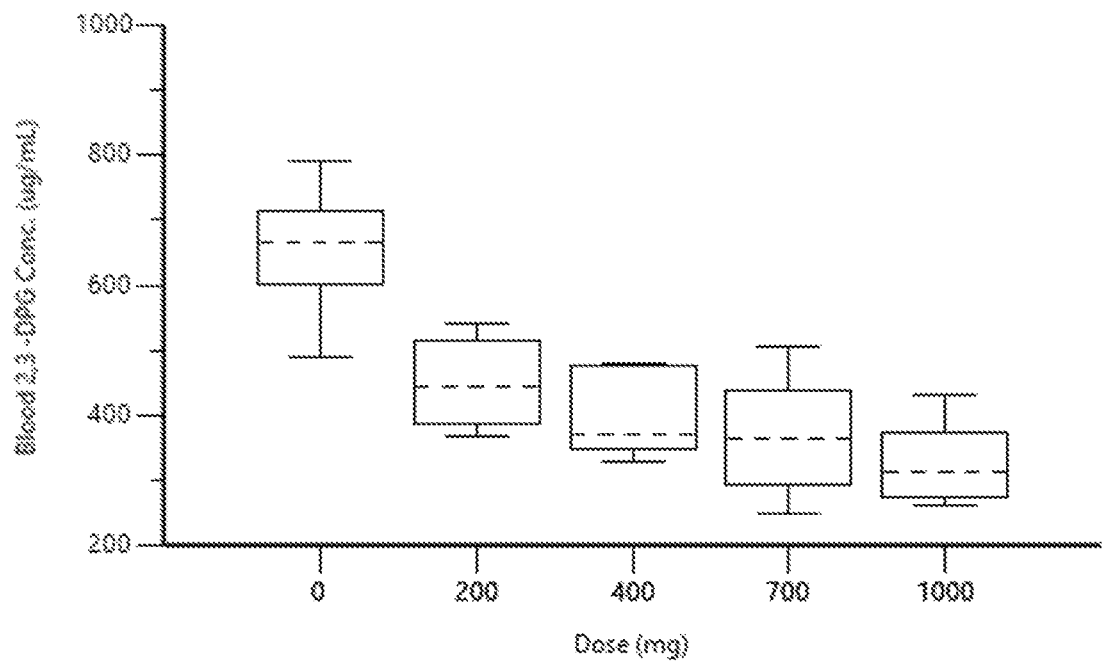
FIG. 19 is a graph of the blood 2,3-DPG levels measured 24 hours post-dose in healthy volunteers who received a single dose of Compound 1 or placebo.

FIG. 18 is a graph of the blood 2,3-DPG levels measured over time in healthy volunteers who received a single dose of Compound 1 (200 mg, 400 mg, 700 mg, or 1000 mg) or placebo. As shown in FIG. 18, healthy volunteers who received Compound 1 experienced a decrease in blood 2,3-DPG levels, relative subjects who received the placebo. FIG. 19 is a graph of the blood 2,3-DPG levels measured 24 hours post-dose in healthy volunteers who received a single dose of Compound 1 (200 mg, 400 mg, 700 mg, or 1000 mg) or placebo. As shown in FIG. 19, healthy volunteers who received Compound 1 experienced a decrease in blood 2,3-DPG levels at 24 hours post-dose, relative to subjects who received the placebo.

In the SAD cohorts, the subjects' P50 (PO$_2$ at 50% hemoglobin saturation) were determined 24-hours post-dose. P50 measured 24 hours after a single dose of Compound 1 were reduced at all dose levels tested (median reduction ranged from ~3-5 mmHg). Table 15 reports the mean absolute change in P50, relative to baseline, measured

TABLE 13

Summary of Mean Maximum Percent Change in Key PD Measures from Baseline

| PD Marker | Statistics | SAD | | MAD | |
|---|---|---|---|---|---|
| | | Placebo (N = 8) | Compound 1 (N = 24) | Placebo (N = 12) | Compound 1 (N = 36) |
| 2,3-DPG | Mean | −19.5 | −46.8 | −17.0 | −56.3 |
| | (95% CI) | (−25.0, −14.0) | (−50.3, −43.2) | (−22.9, −11.1) | (−58.9, −53.7) |
| | P-value | | <0.0001 | | <0.0001 |
| ATP | Mean | 9.2 | 24.4 | 7.2 | 68.5 |
| | (95% CI) | (0.5, 18.0) | (18.4, 30.3) | (−0.3, 14.7) | (63.6, 73.3) |
| | P-value | | 0.0094 | | <0.0001 |
| P$_{50}$ | Mean | 0.9 | −15.6 | −0.8 | −15.9 |
| | (95% CI) | (−1.2, 2.9) | (−17.5, −13.8) | (−3.0, 1.4) | (−17.2, −14.5) |
| | P-value | | <0.0001 | | <0.0001 |

24 hours after a single dose of Compound 1 (200 mg, 400 mg, 700 mg, or 1000 mg) or placebo in healthy volunteers.

TABLE 15

Mean Absolute Change in P50 (mmHg)

| Dose | Mean Absolute Change |
| --- | --- |
| Placebo | 0.20 |
| 200 mg | −2.91 |
| 400 mg | −3.41 |
| 700 mg | −4.85 |
| 1000 mg | −5.05 |

Figure 20:
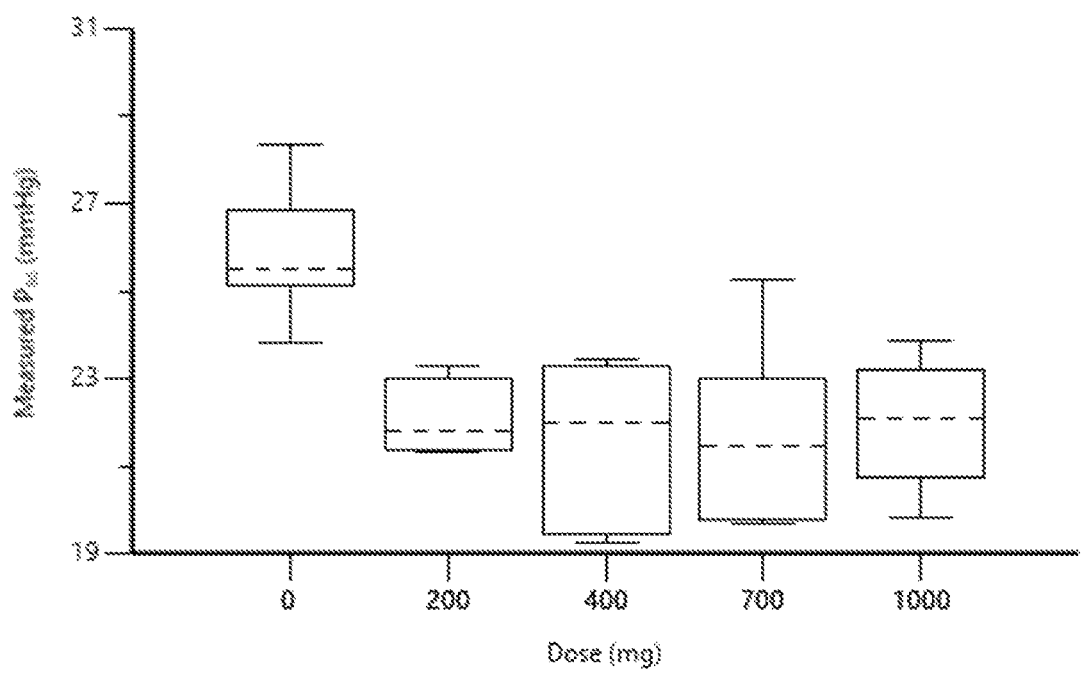
FIG. 20 is a graph of the P50 values measured 24 hours post-dose in healthy volunteers who received a single dose of Compound 1 or placebo.
Figure 21:
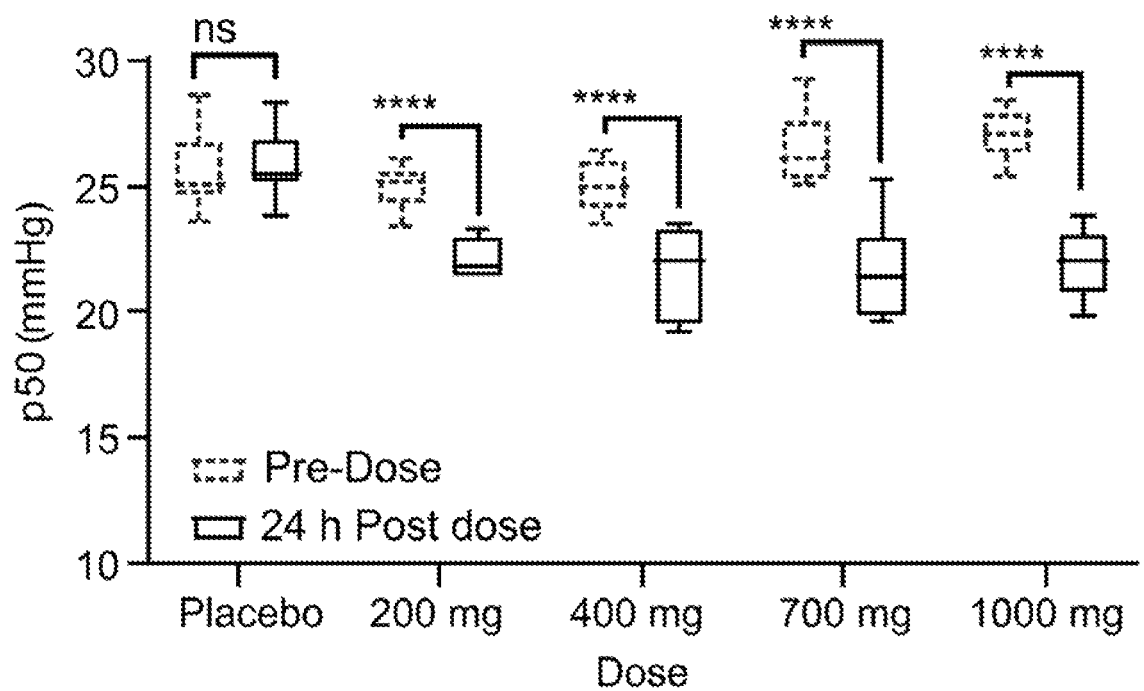
FIG. 21 is a graph of the P50 values measured pre-dose and 24-hours post-dose in healthy volunteers who received a single dose of Compound 1 or placebo.

FIG. 20 is a graph of the P50 values measured 24 hours post-dose in healthy volunteers who received a single dose of Compound 1 (200 mg, 400 mg, 700 mg, or 1000 mg) or placebo. As shown in FIG. 20, healthy volunteers who received Compound 1 experienced a decrease in P50, relative to subjects who received the placebo. FIG. 21 is a graph of the P50 values measured pre-dose and 24-hours post-dose in healthy volunteers who received a single dose of Compound 1 (200 mg, 400 mg, 700 mg, or 1000 mg) or placebo. As shown in FIG. 21, healthy volunteers who received Compound 1 experienced a decrease in P50 relative to baseline, while subjects who received the placebo did not.

In the MAD cohorts, the subjects' blood 2,3-DPG levels were measured periodically after dosing by a qualified LC-MS/MS method for the quantitation of 2,3-DPG in blood. The maximum decrease in 2,3-DPG on Day 14 was 55% from baseline (median). 2,3-DPG levels reached a nadir and plateaued on Day 1 and had not returned to baseline levels 72 hours after the final dose on Day 14. Table 16 reports the median percentage change in 2,3-DPG blood levels, relative to baseline, measured over time after the first dose on days 1 and 14 in healthy volunteers who received daily doses of Compound 1 (100 mg BID, 200 mg BID, or 300 mg BID) or placebo for 14 days. Accordingly, the median reduction in the concentration of 2,3-DPG, relative to baseline, was at least about 25% at all dose levels tested 24 hours after administration of the first dose on day 1 and at least about 40% at all dose levels tested 24 hours after administration of the first dose on day 14.

TABLE 16

Median Percentage Change in 2,3-DPG Levels (Days 1 and 14)

| | Dose | | | | | | | |
| --- | --- | --- | --- | --- | --- | --- | --- | --- |
| Time After First Daily Dose | 100 mg BID Day | | 200 mg BID Day | | 300 mg BID Day | | Placebo Day | |
| | 1 | 14 | 1 | 14 | 1 | 14 | 1 | 14 |
| 0 | 0.0 | −42.0 | 0.0 | −48.2 | 0.0 | −59.4 | 0.0 | −7.6 |
| 6 | −16.1 | −44.3 | −13.1 | −48.5 | −18.8 | −53.0 | −2.9 | −10.9 |
| 8 | −12.1 | −44.7 | −22.3 | −44.3 | −23.8 | −54.2 | −0.6 | −1.6 |
| 12 | −18.1 | −43.6 | −23.1 | −42.2 | −31.6 | −55.3 | −7.1 | −1.6 |
| 16 | −18.4 | −43.9 | −33.9 | −42.9 | −40.7 | −52.4 | −6.7 | −5.3 |
| 24 | −27.8 | −44.1 | −43.5 | −44.3 | −50.8 | −52.1 | 1.1 | −10.7 |
| 48 | | −34.7 | | −38.7 | | −44.5 | | −1.0 |
| 72 | | −20.2 | | −20.2 | | −32.9 | | −7.0 |

Figure 22:
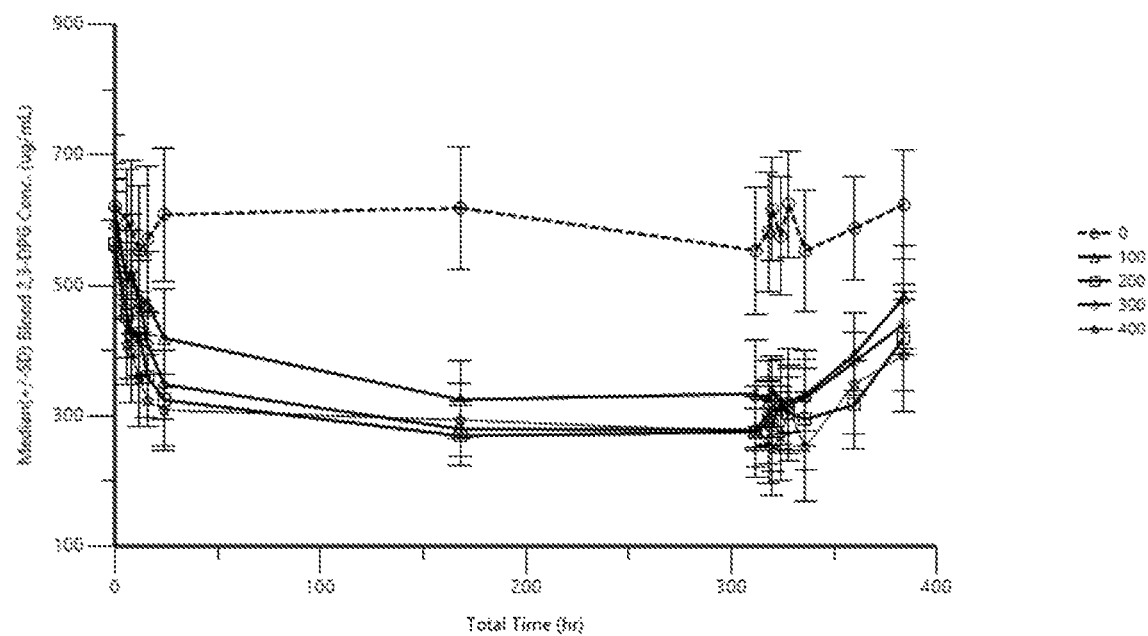
FIG. 22 is a graph of the blood 2,3-DPG levels measured over time in healthy volunteers who received daily doses of Compound 1 or placebo for 14 days.
Figure 23:
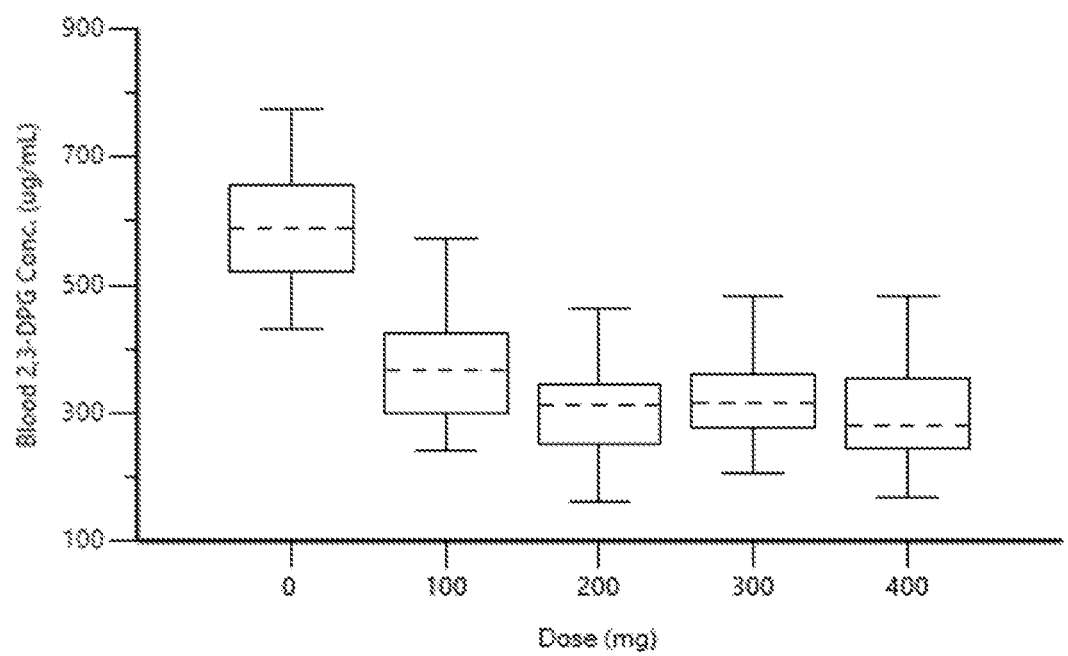
FIG. 23 is a graph of the blood 2,3-DPG levels measured on day 14 in healthy volunteers who received daily doses of Compound 1 or placebo for 14 days.

FIG. 22 is a graph of the blood 2,3-DPG levels measured over time in healthy volunteers who received daily doses of Compound 1 (100 mg BID, 200 mg BID, 300 mg BID, or 400 mg QD) or placebo for 14 days. As shown in FIG. 22, healthy volunteers who received Compound 1 experienced a decrease in blood 2,3-DPG levels, relative subjects who received the placebo. FIG. 23 is a graph of the blood 2,3-DPG levels measured on day 14 in healthy volunteers who received daily doses of Compound 1 (100 mg BID, 200 mg BID, 300 mg BID, or 400 mg QD) or placebo for 14 days. As shown in FIG. 23, healthy volunteers who received Compound 1 experienced a decrease in blood 2,3-DPG levels, relative to subjects who received the placebo.

In the MAD cohorts, the subjects' P50 (PO$_2$ at 50% hemoglobin saturation) were determined on day 14. P50 values measured after 14 days of twice daily dosing were reduced at all dose levels tested (median reduction ranged from −3-5 mmHg). Table 17 reports the mean absolute change in P50, relative to baseline, measured on day 14 in healthy volunteers who received daily doses of Compound 1 (100 mg BID, 200 mg BID, or 300 mg BID) or placebo for 14 days.

TABLE 17

Mean Absolute Change in P50 (mmHg) (Day 14)

| Dose | Mean Absolute Change |
| --- | --- |
| Placebo | −0.38 |
| 100 mg BID | −3.26 |
| 200 mg BID | −4.14 |
| 300 mg BID | −5.34 |

Figure 24:
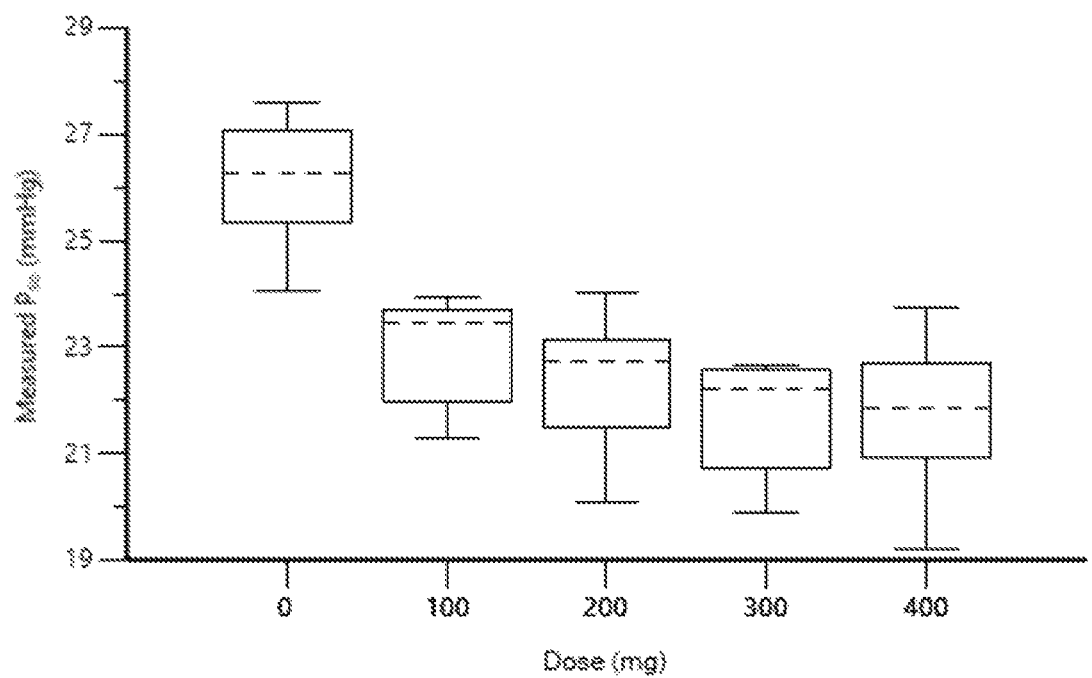
FIG. 24 is a graph of the P50 values measured on day 14 in healthy volunteers who received daily doses of Compound 1 or placebo for 14 days.
Figure 25:
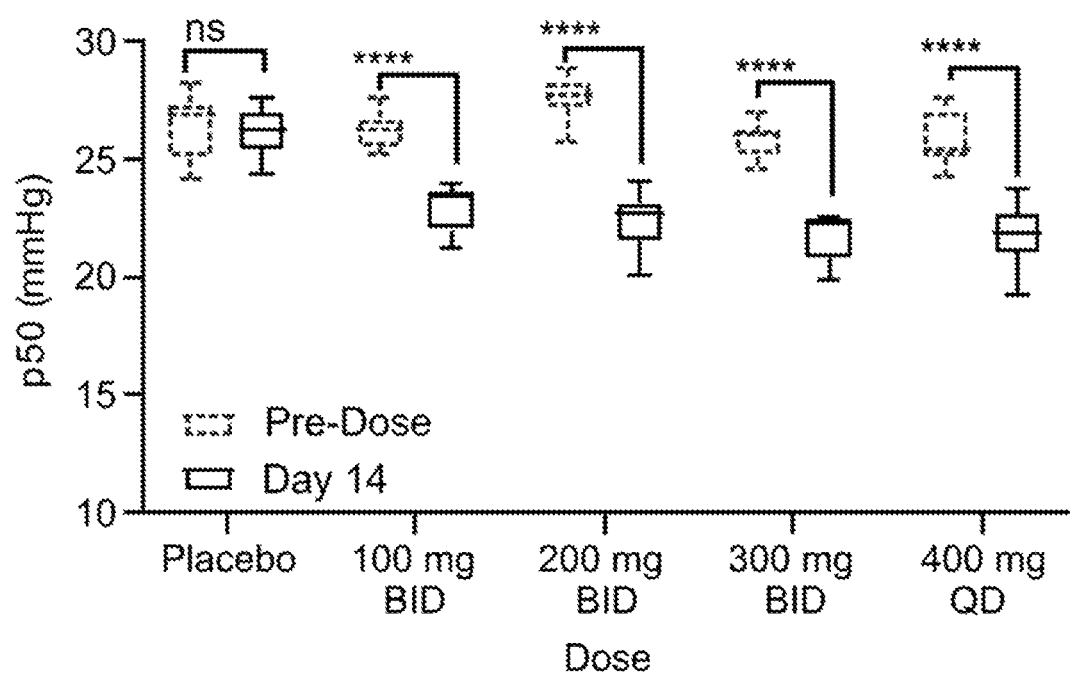
FIG. 25 is a graph of the P50 values measured pre-dose and on day 14 in healthy volunteers who received daily doses of Compound 1 or placebo for 14 days.

FIG. 24 is a graph of the P50 values measured on day 14 in healthy volunteers who received daily doses of Compound 1 (100 mg BID, 200 mg BID, 300 mg BID, or 400 mg QD) or placebo for 14 days. As shown in FIG. 24, healthy volunteers who received Compound 1 experienced a decrease in P50, relative to subjects who received the placebo. FIG. 25 is a graph of the P50 values measured pre-dose and on day 14 in healthy volunteers who received daily doses of Compound 1 (100 mg BID, 200 mg BID, 300 mg BID, or 400 mg QD) or placebo for 14 days. As shown in FIG. 25, healthy volunteers who received Compound 1 experienced a decrease in P50 relative to baseline, while subjects who received the placebo did not.

In the MAD cohorts, the subjects' blood ATP levels were measured on day 14 by a qualified LC-MS/MS method for the quantitation of ATP in blood. ATP levels were elevated, relative to baseline, on day 14, and remained elevated 60 hours after the last dose. Table 18 reports the median percentage change in blood ATP levels, relative to baseline, measured over time after the first dose on day 14 in healthy volunteers who received daily doses of Compound 1 (100 mg BID, or 200 mg BID) or placebo for 14 days.

TABLE 18

Median Percentage Change in ATP Levels (Day 14)

| Time After First Daily | Dose | | |
| --- | --- | --- | --- |
| Dose | 100 mg BID | 200 mg BID | Placebo |
| 0 | 41.5 | 55.3 | −0.5 |
| 6 | 43.8 | 48.1 | 2.8 |
| 8 | 47.8 | 58.4 | −4.1 |
| 12 | 45.4 | 56.2 | 2.3 |
| 16 | 44.8 | 57.0 | −6.8 |
| 24 | 55.0 | 64.0 | 2.9 |
| 48 | 52.2 | 58.9 | 4.7 |
| 72 | 49.2 | 54.0 | 2.2 |

Figure 26:
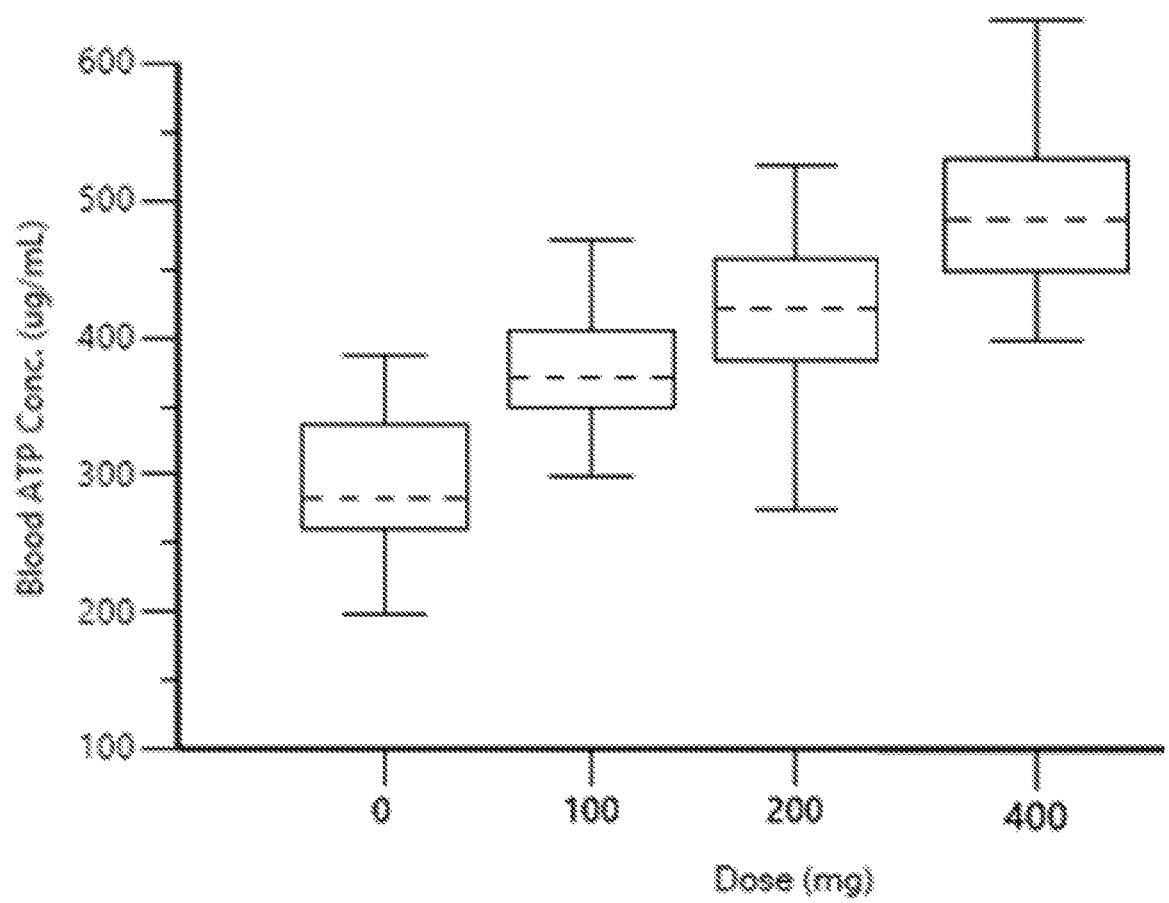
FIG. 26 is a graph of the blood ATP levels measured on day 14 in healthy volunteers who received daily doses of Compound 1 or placebo for 14 days.

FIG. 26 is a graph of the blood ATP levels measured on day 14 in healthy volunteers who received daily doses of Compound 1 (100 mg BID, 200 mg BID, 300 mg BID, or 400 mg QD) or placebo for 14 days. As shown in FIG. 26, healthy volunteers who received Compound 1 experienced an increase in blood ATP levels, relative to subjects who received the placebo.

Figure 27:
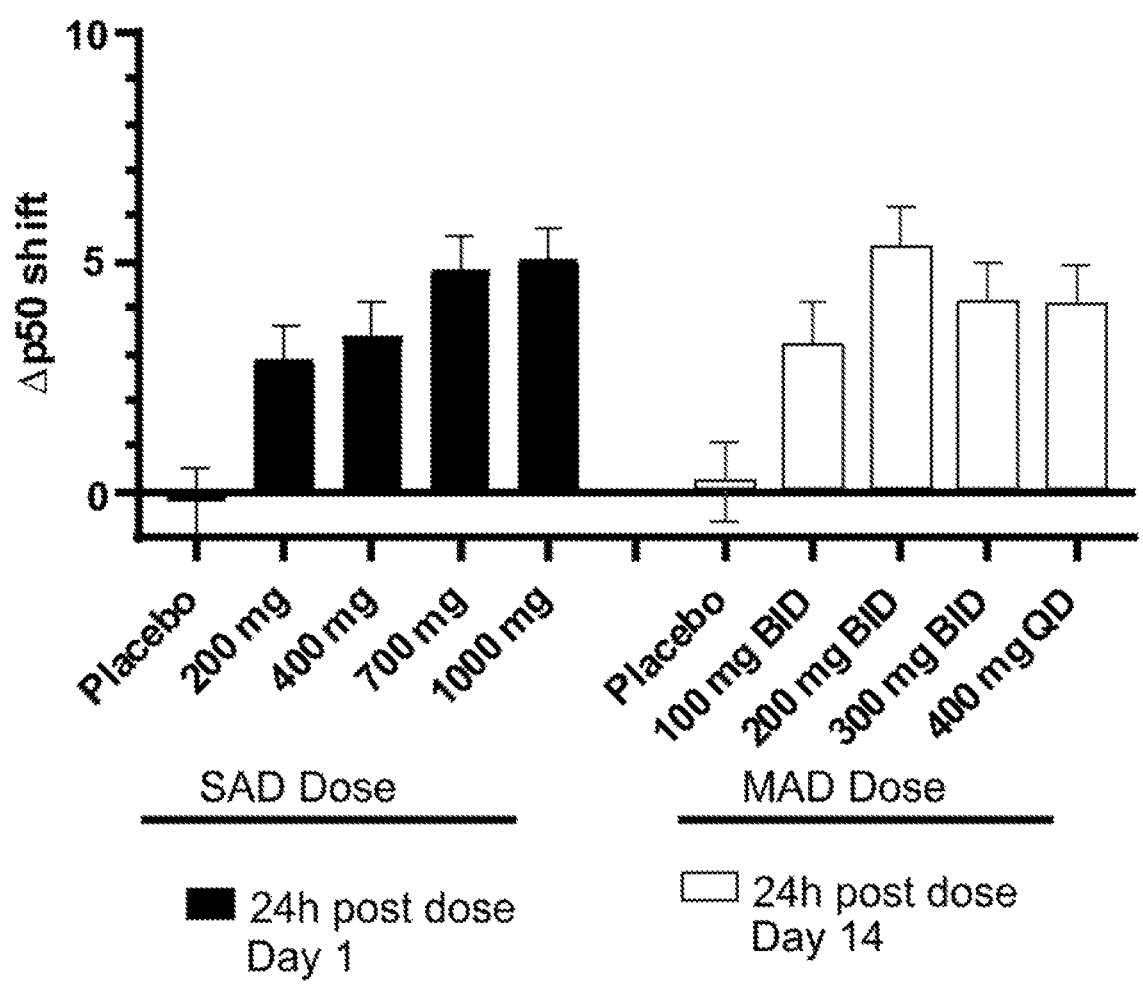
FIG. 27 is a graph showing the difference in the P50 values determined pre-dose and 24 hours post-dose (SAD cohorts) and 24 hours post-dose on day 14 (MAD cohorts) in healthy volunteers who received Compound 1 or placebo.

FIG. 27 is a graph showing the difference in the P50 values determined pre-dose and 24 hours post-dose (SAD cohorts) and 24 hours post-dose on day 14 (MAD cohorts) in healthy volunteers who received Compound 1 or placebo. As shown in FIG. 27, healthy volunteers who received Compound 1 experienced a change (decrease) in P50 relative to baseline, while subjects who received the placebo did not.

Figure 28:
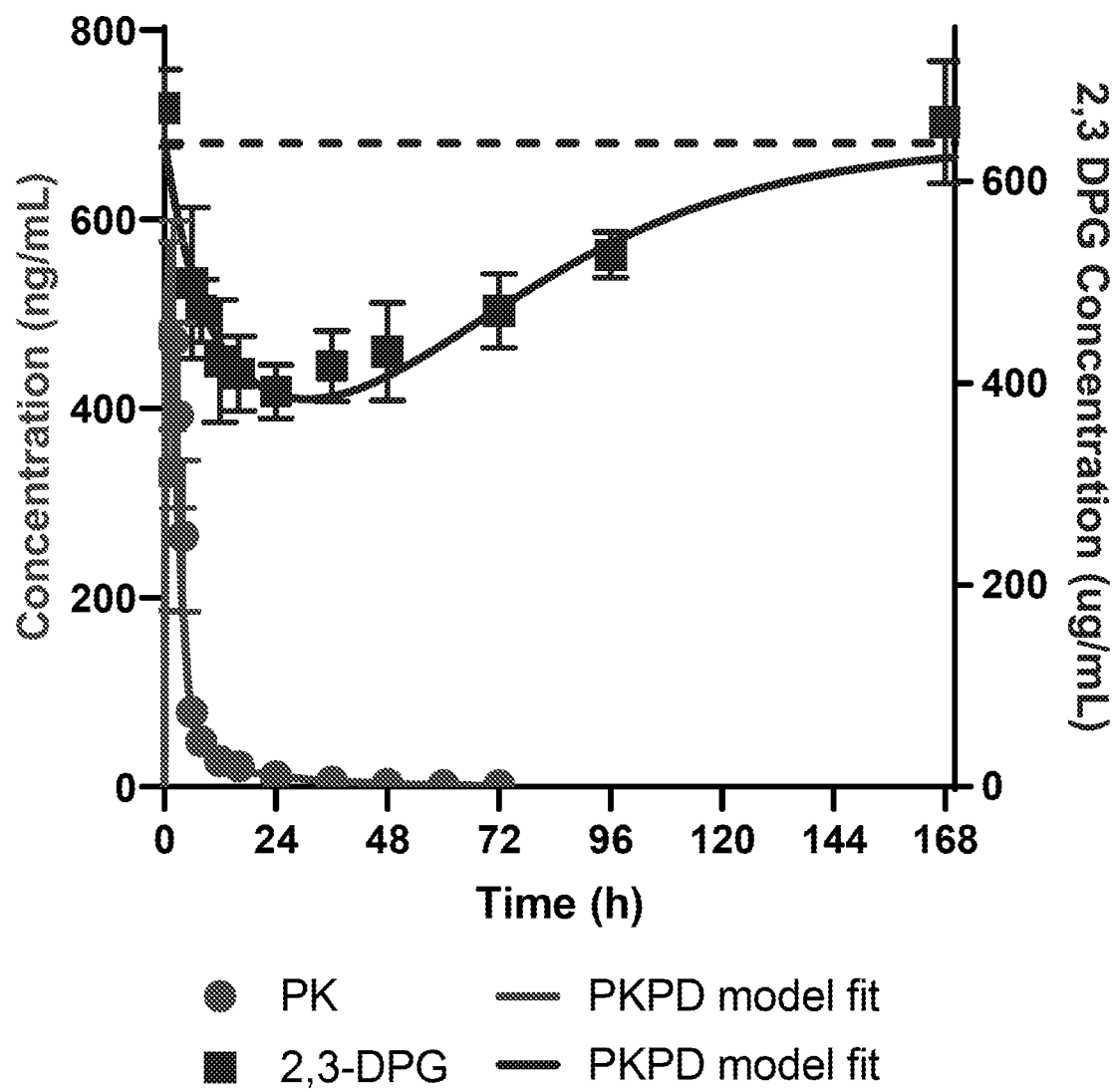
FIG. 28 is a graph plotting the blood concentration of Compound 1 (ng/mL) measured in healthy volunteer (HV) patients on a first (left) axis and the concentration of 2,3-DPG (micrograms/mL) measured in these HV patients on a second (right) axis after administration of a single dose of Compound 1 (400 mg).

FIG. 28 is a graph plotting the blood concentration of Compound 1 (ng/mL) measured in healthy volunteer (HV) patients on a first (left) axis and the concentration of 2,3-DPG (micrograms/mL) measured in these HV patients on a second (right) axis after administration of a single dose of Compound 1 (400 mg). Solid symbols represent geometric means and Standard errors of the observed Compound 1 plasma and 2,3 DPG concentrations. As shown in the figure, the observed 2,3 DPG modulation does not track directly plasma pharmacokinetics (blood concentration of Compound 1) where the pharmacodynamic maximum (i.e., the minimum of the 2,3-DPG concentration, at time ~24 h) occurred nearly 24 h after the pharmacokinetic maximum (i.e., maximum of the PK curve, at time ~1-2 h). The observed pharmacodynamic response in HVs was durable, with a calculated PD half-life of ~20 h, where 2,3-DPG depression was observed long after plasma levels were undetectable. Taken together, this suggests that identifying the pharmacologically active dose cannot be adequately performed using pharmacokinetic parameters ($C_{max}/C_{min}$/AUC) in isolation, but rather support an approach that includes integrating the temporal pharmacokinetic/pharmacodynamic relationship to provide the platform of evidence that QD dosing may be feasible in sickle cell disease patients.

Figure 29:
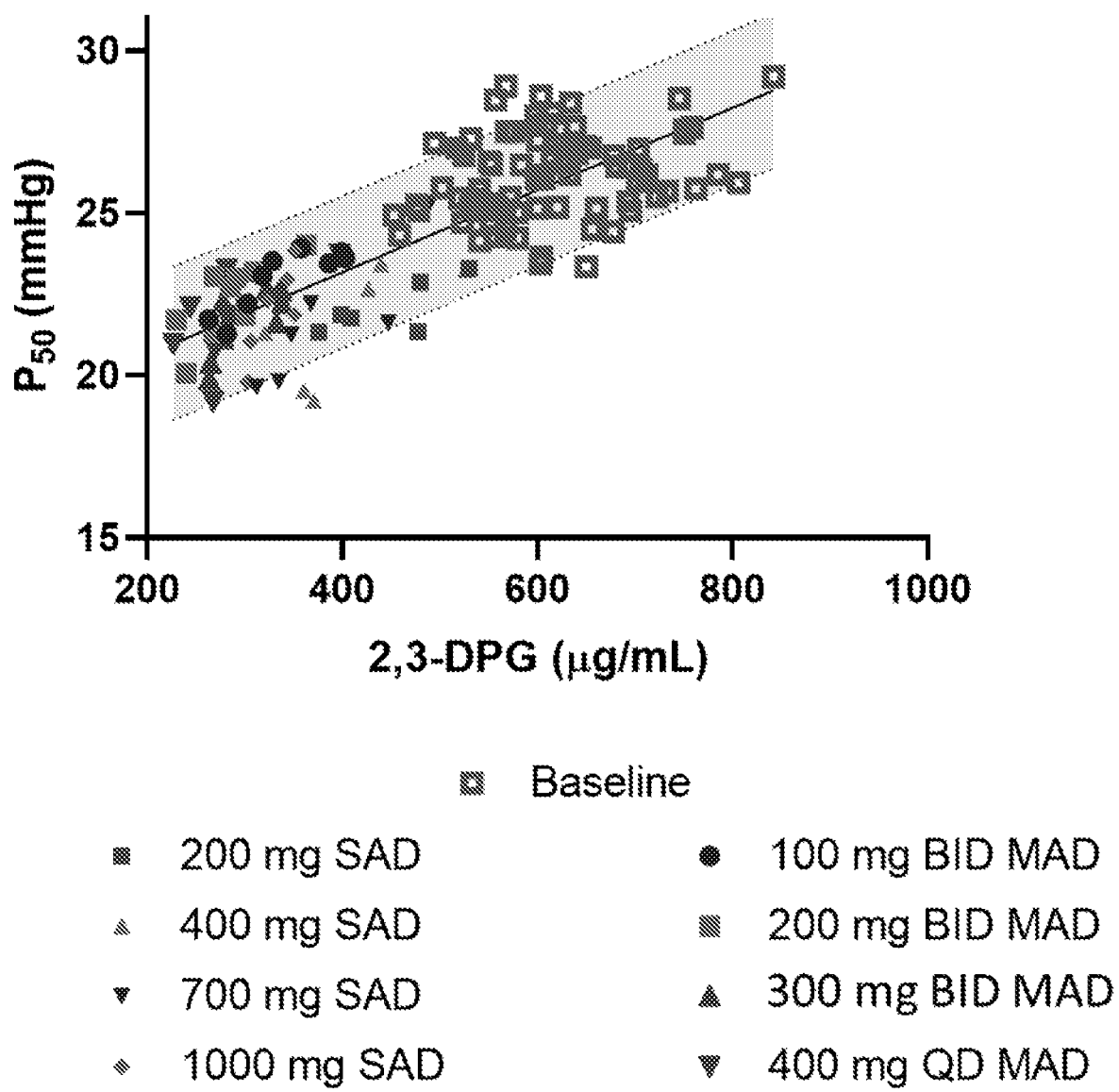
FIG. 29 is a scatter plot of 2,3-DPG levels and P50 values observed in healthy volunteers in the SAD and MAD cohorts.

FIG. 29 is a scatter plot of 2,3-DPG levels and P50 values observed in healthy volunteers in the SAD and MAD cohorts. Solid symbols represent the observed P50/2,3-DPG levels in healthy volunteers dosed with Compound 1 at 24 h following the last administered dose. Baseline data represents P50/2,3 DPB data obtained either prior to Compound 1 treatment and from healthy volunteers dosed with placebo. A positive correlative relationship between 2,3 DPG and p50 levels was observed for patients receiving various doses.

Example 9: Analysis of ATP and 2,3 DPG in K2EDTA Whole Blood by LC-MS/MS

The following procedures are employed for the analysis of ATP and 2,3-DPG in human whole blood K2EDTA using a protein precipitation extraction procedure and analysis by LC-MS/MS.

This bioanalytical method applies to the parameters described below:

| | |
|---|---|
| Assay Range | 25,000-1,500,000 ng/mL |
| Extraction Volume | 15.0 μL |
| Species/Matrix/Anticoagulant | Water as a surrogate for Human Whole Blood K2EDTA |
| Extraction type | Protein Precipitation |
| Sample Storage | 80° C. |
| Mass Spectrometer | API-5500 |
| Acquisition software | Analyst/Aria System |

The following precautions are followed:

1. Standard and QC samples are prepared on ice and stored in plastic containers.
2. Study samples and QC samples are thawed on ice.
3. Extraction is performed on ice.

The following definitions and abbreviations are employed:

| | |
|---|---|
| CRB | Carryover remediation blanks |
| FT | Freeze-thaw |
| MPA | Mobile phase A |
| MPB | Mobile phase B |
| NA | Not applicable |
| NR | Needle rinse |
| RT | Retention time |
| SIP | Stability in progress |
| TBD | To be determined |

The following chemicals, matrix, and reagents are used:

K₂EDTA Human Whole Blood, BioreclamationIVT or equivalent (Note: BioReclamationIVT and BioIVT are considered equivalent)
Acetonitrile (ACN), HPLC Grade or better
Ammonium Acetate (NH₄OAC), HPLC grade or equivalent
Ammonium Hydroxide (NH₄OH, 28-30%), ACS grade or better
Dimethylsulfoxide (DMSO), ACS grade or better
Formic Acid (FA), 88% ACS grade
Isopropanol (IPA), HPLC Grade or better
Methanol (MeOH), HPLC Grade or better
Water (H₂O), Milli-Q or HPLC Grade
ATP - Analyte, Sponsor or supplier
ATP-IS- IS, Sponsor or supplier
2,3-DPG - Analyte, Sponsor or supplier
2,3-DPG-IS- IS, Sponsor or supplier The following procedures are used for reagent preparation. Any applicable weights and volumes listed are nominal and may be proportionally adjusted as long as the targeted composition is achieved:

| Solution | Final Solution Composition | Nominal Volumes for Solution Preparation | Storage Conditions |
|---|---|---|---|
| Mobile Phase A (MPA) | 10 mM Ammoniumn Acetate in water pH 8.5 | Weigh approximately 770.8 mg of Ammonium Acetate; add to a bottle with 1000 mL of water. Adjust pH to 8.3-8.7 using Ammonium Hydroxide. | Ambient Temperature |

-continued

| Solution | Final Solution Composition | Nominal Volumes for Solution Preparation | Storage Conditions |
|---|---|---|---|
| Mobile Phase B (MPB) | 5:95 MPA:ACN | Add 50.0 mL of MPA to 950 mL of CAN. Mix. | Ambient Temperature |
| Needle Rinse 1 (NR1) | 25:25:25:25:0.1 (v:v:v:v:v) MeOH:ACN:H2O:IPA:NH$_4$OH | Add 500 mL of MeOH, 500 mL of ACN, 500 mL of H$_2$O, 500 mL of IPA, and 2 mL of NH$_4$OH. Mix. | Ambient Temperature |
| Needle Rings 2 (NR2) | 90:10:0.1 (v:v:v) H$_2$0:MeOH:FA | Add 2 mL of FA to 200 mL of MeOH and 1800 mL of H$_2$0. Mix. | Ambient Temperature |

Calibration standards are prepared using water as the matrix according to the table presented below. The indicated standard is prepared by diluting the indicated spiking volume of stock solution with the indicated matrix volume.

| Calibration Standard | Stock Solution | Stock Conc. (ng/mL) | Spiking Vol. (mL) | Matrix Vol. (mL) | Final Vol. (mL) | Final Conc. (ng/mL) |
|---|---|---|---|---|---|---|
| STD-6 | ATP Stock | 60,000,000 | 0.0100 | 0.380 | 0.400 | 1,500,000 |
|  | 2,3-DPG Stock | 60,000,000 | 0.0100 |  |  |  |
| STD-5 | STD-6 | 1,500,000 | 0.100 | 0.200 | 0.300 | 500,000 |
| STD-4 | STD-6 | 1,500,000 | 0.0500 | 0.325 | 0.375 | 200,000 |
| STD-3 | STD-6 | 1,500,000 | 0.0250 | 0.350 | 0.375 | 100,000 |
| STD-2 | STD-5 | 500,000 | 0.0500 | 0.450 | 0.500 | 50,000 |
| STD-1 | STD-5 | 500,000 | 0.0250 | 0.475 | 0.500 | 25,000 |
| Cond. | STD-5 | 500,000 | 0.0250 | 0.975 | 1.00 | 12,500 |

Quality control standards are prepared using water as the matrix according to the table presented below. The indicated quality control standard is prepared by diluting the indicated spiking volume of stock solution with the indicated matrix volume.

| Quality Control Standard | Stock Solution | Stock Conc. (ng/mL) | Spiking Vol. (mL) | Matrix Vol. (mL) | Final Vol. (mL) | Final Conc. (ng/mL) |
|---|---|---|---|---|---|---|
| QC-High | ATP Stock | 60,000,000 | 0.160 | 7.68 | 8.00 | 1,200,000 |
|  | 2,3-DPG Stock | 60,000,000 | 0.160 |  |  |  |
| QC-Mid | QC-High | 1,200,000 | 1.50 | 4.50 | 6.00 | 300,000 |
| QC-Low | QC-Mid | 300,000 | 1.50 | 4.50 | 6.00 | 75,000 |

An internal standard spiking solution is prepared with a final concentration of 12,500 ng/mL ATP and 2,3-DPG by diluting stock solutions of ATP and 2,3-DPG at concentrations of 1,000,000 ng/mL with water. 0.200 mL each of the ATP and 2,3-DPG stock solutions are diluted with 15.6 mL of water to produce a final volume of 16.0 mL at a final concentration of 12,500 ng/mL of ATP and 2,3-DPG.

The following procedures are used for sample extraction prior to analysis via LC-MS/MS. 15.0 µL of the calibration standards, quality controls, matrix blanks, and samples are aliquoted into a 96-well plate. 50.0 µL of the internal standard spiking solution is added to all samples on the plate, with the exception of the matrix blank samples; 50.0 µL of water is added to the matrix blank samples. Subsequently, 150 µL of water is added to all samples on the plate. The plate is then covered and agitated by vortex at high speed for ten minutes, after which 750 µL of methanol is added to all samples on the plate. The plate is covered and agitated by vortex for approximately 1 minute. The plate is then centrifuged at approximately 3500 RPM at approximately 4° C. for five minutes. After centrifugation, a liquid handler is used to transfer 50 µL of each sample to a new 96-well plate, and 200 µL of acetonitrile is added to all samples on the plate. The newly prepared plate is covered and agitated by vortex for approximately 1 minute. The plate is then centrifuged at approximately 3500 RPM at approximately 4° C. for 2 minutes.

The following LC parameters and gradient conditions are used for analysis of the extracted samples:

| LC Parameters | | |
|---|---|---|
| Analytical Column | Vendor: | SeQuant |
|  | Description: | ZIC-pHILIC |
|  | Dimensions: | 50 mm × 2.1 mm |
|  | Column Heater Temperature: | 40° C. |
| Plate Rack | Position: | Cold Stack |
|  | Cold Stack Set Point: | 5° C. |
| Mobile Phase | Mobile Phase A (MPA) | 10 mM Ammoniumn Acetate in water pH 8.5 |
|  | Mobile Phase B (MPB) | 5:95 MPA:ACN |
| Injection Volume |  | 5 µL |

| LC Gradient | | | | |
|---|---|---|---|---|
| Step | Time (s) | Flow (mL/min) | Gradient Setting | % MPB |
| 1 | 50 | 0.400 | Step | 5 |
| 2 | 30 | 0.400 | Ramp | 95 |
| 3 | 70 | 0.400 | Step | 5 |

Data is collected starting at 0.08 min and is collected over a data window length of 0.70 min.

The following MS parameters are used for analysis of the extracted samples using an API-5500 Mass Spectrometer:

| Interface: | Turbo Ion Spray Ionization, positive-ion mode | |
|---|---|---|
| Scan Mode: | Multiple Reaction Monitoring (MRM) | |
| | Parent/Product: | Dwell Time (ms): |
| Scan Parameters: | 506.0/159.0 | 50 |
| | 521.0/159.0 | 25 |
| | 265.0/166.8 | 50 |
| | 268.0/169.8 | 25 |
| Source Temperature: | 400° C. | |

The collected MS data is analyzed and sample concentrations are quantified using peak area ratios with a linear $1/x^2$ regression type.

We claim:

1. A compound of formula

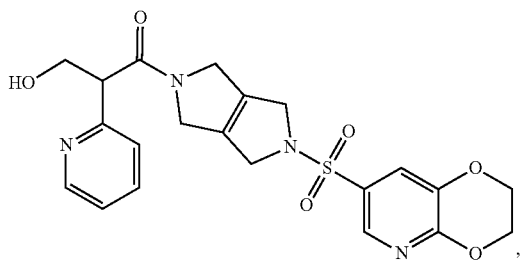

or a pharmaceutically acceptable salt thereof.

2. The compound of claim 1, or a pharmaceutically acceptable salt thereof, wherein the compound is Compound 3:

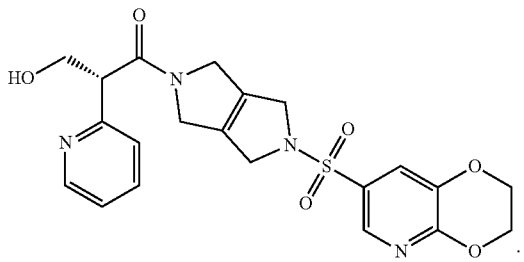 [SMILES: O=C([C@@H](CO)c1ccccn1)N1CC2=C(C1)CN(S(=O)(=O)c1cnc3c(c1)OCCO3)C2]

3. The compound of claim 1, or a pharmaceutically acceptable salt thereof, wherein the compound is Compound 4:

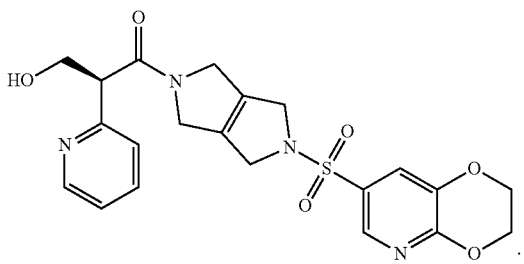 [SMILES: O=C([C@H](CO)c1ccccn1)N1CC2=C(C1)CN(S(=O)(=O)c1cnc3c(c1)OCCO3)C2]

4. A compound of formula

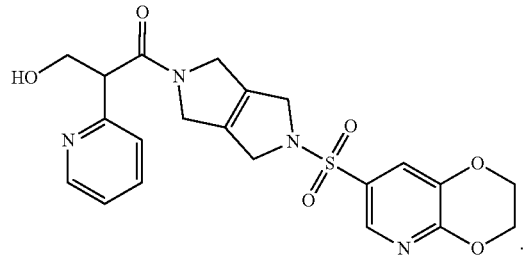

5. The compound of claim 4, wherein the compound is Compound 3:

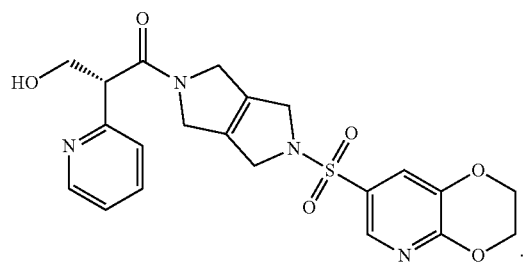 [SMILES: O=C(C(CO)c1ccccn1)N1CC2=C(C1)CN(S(=O)(=O)c1cnc3c(c1)OCCO3)C2]

6. The compound of claim 4, wherein the compound is Compound 4:

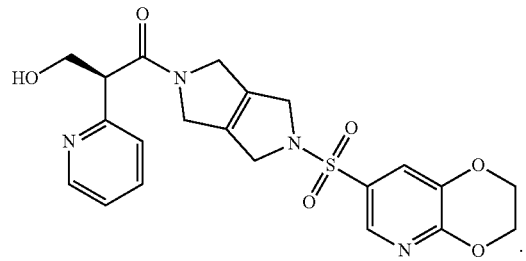 [SMILES: O=C([C@H](CO)c1ccccn1)N1CC2=C(C1)CN(S(=O)(=O)c1cnc3c(c1)OCCO3)C2]

7. A pharmaceutical composition comprising the compound of claim 1, or a pharmaceutically acceptable salt thereof, and a pharmaceutically acceptable carrier.

8. A pharmaceutical composition comprising the compound of claim 2, or a pharmaceutically acceptable salt thereof, and a pharmaceutically acceptable carrier.

9. A pharmaceutical composition comprising the compound of claim 3, or a pharmaceutically acceptable salt thereof, and a pharmaceutically acceptable carrier.

10. A pharmaceutical composition comprising the compound of claim 4 and a pharmaceutically acceptable carrier.

11. A pharmaceutical composition comprising the compound of claim 5 and a pharmaceutically acceptable carrier.

12. A pharmaceutical composition comprising the compound of claim 6 and a pharmaceutically acceptable carrier.

* * * * *